(12) United States Patent
Leppanen et al.

(10) Patent No.: US 10,328,149 B2
(45) Date of Patent: Jun. 25, 2019

(54) CONJUGATES COMPRISING AN ANTI-EGFR1 ANTIBODY

(71) Applicant: Tenboron Oy, Helsinki (FI)

(72) Inventors: Anne Leppanen, Vantaa (FI); Filip S. Ekholm, Porvoo (FI); Jari Helin, Rajamaki (FI); Hanna Salo, Helsinki (FI); Anne Kanerva, Helsinki (FI)

(73) Assignee: TENBORON OY, Helsinki (FI)

( * ) Notice: Subject to any disclaimer, the term of this patent is extended or adjusted under 35 U.S.C. 154(b) by 0 days.

(21) Appl. No.: 15/318,030

(22) PCT Filed: Jun. 12, 2015

(86) PCT No.: PCT/FI2015/050422
§ 371 (c)(1),
(2) Date: Dec. 12, 2016

(87) PCT Pub. No.: WO2015/189477
PCT Pub. Date: Dec. 17, 2015

(65) Prior Publication Data
US 2017/0112931 A1 Apr. 27, 2017

(30) Foreign Application Priority Data

Jun. 13, 2014 (FI) ..... 20145552
Feb. 20, 2015 (FI) ..... 20155114

(51) Int. Cl.
| | | |
|---|---|---|
| A61K 39/00 | (2006.01) |
| A61K 41/00 | (2006.01) |
| A61K 47/68 | (2017.01) |
| A61K 31/721 | (2006.01) |
| C07K 16/28 | (2006.01) |
| C07K 16/30 | (2006.01) |
| C07K 14/245 | (2006.01) |

(52) U.S. Cl.
CPC ........ *A61K 41/0095* (2013.01); *A61K 31/721* (2013.01); *A61K 47/6849* (2017.08); *A61K 47/6883* (2017.08); *C07K 14/245* (2013.01); *C07K 16/2863* (2013.01); *C07K 16/30* (2013.01); *A61K 2039/505* (2013.01); *C07K 2317/14* (2013.01); *C07K 2317/24* (2013.01); *C07K 2317/51* (2013.01); *C07K 2317/515* (2013.01); *C07K 2317/55* (2013.01); *C07K 2317/56* (2013.01); *C07K 2317/622* (2013.01); *C07K 2317/77* (2013.01); *C07K 2317/94* (2013.01)

(58) Field of Classification Search
None
See application file for complete search history.

(56) References Cited

U.S. PATENT DOCUMENTS

| | | |
|---|---|---|
| 4,046,722 A | 9/1977 | Rowland |
| 4,699,784 A | 10/1987 | Shih et al. |
| 5,057,313 A | 10/1991 | Shih et al. |
| 5,264,365 A | 11/1993 | Georgiou et al. |
| 5,508,192 A | 4/1996 | Georgiou et al. |
| 5,558,864 A | 9/1996 | Bendig et al. |
| 5,635,483 A | 6/1997 | Pettit et al. |
| 5,639,635 A | 6/1997 | Joly et al. |
| 5,714,166 A | 2/1998 | Tomalia et al. |
| 5,844,093 A | 12/1998 | Kettleborough et al. |
| 5,846,741 A | 12/1998 | Griffiths et al. |
| 5,851,527 A | 12/1998 | Hansen |
| 5,958,408 A | 9/1999 | Griffiths et al. |
| 5,965,131 A | 10/1999 | Griffiths et al. |
| 6,027,888 A | 2/2000 | Georgiou et al. |
| 6,083,715 A | 7/2000 | Georgiou et al. |
| 6,228,362 B1 | 5/2001 | Griffiths et al. |
| 6,235,883 B1 | 5/2001 | Jakobovits et al. |
| 6,319,500 B1 | 11/2001 | Goldenberg |
| 6,409,990 B1 | 6/2002 | Vera |
| 6,632,939 B2 | 10/2003 | Machida et al. |
| 6,905,689 B2 | 6/2005 | Schneidinger et al. |

(Continued)

FOREIGN PATENT DOCUMENTS

| | | |
|---|---|---|
| WO | WO 1987/005031 A1 | 8/1987 |
| WO | WO 1988/007378 A1 | 10/1988 |

(Continued)

OTHER PUBLICATIONS

Rivera, F., "Current situation of Panitumumab, Matuzumab, Nimotuzumab and Zalutumumab," Acta Oncol. 2008;47(1):9-19.*
Afar De et al. (2004) Preclinical validation of anti-TMEFF2-auristatin E-conjugated antibodies in the treatment of prostate cancer. Mol Cancer Ther. 3(8):921-32.
Alam F et al. (1987) Boronation of antibodies with mercaptoundecahydro-closo-dodecaborate(2-) anion for potential use in boron neutron capture therapy. Int J Rad Appl Instrum A. 38(7):503-6.
Alam F et al. (1989) Boron neutron capture therapy: linkage of a boronated macromolecule to monoclonal antibodies directed against tumor-associated antigens. J Med Chem. Oct. 1989;32(10):2326-30.
Andersson et al. (1991) Binding of epidermal growth factor-dextran conjugates to cultured glioma cells. Int J Cancer. 47(3):439-444.

(Continued)

*Primary Examiner* — Thomas S Heard
(74) *Attorney, Agent, or Firm* — Patrick J. Halloran

(57) ABSTRACT

The present invention relates to a conjugate comprising an anti-EGFR1 antibody or an EGFR binding fragment thereof and at least one dextran derivative, wherein the dextran derivative comprises at least one D-glucopyranosyl unit, wherein at least one carbon selected from carbon 2, 3 or 4 of the at least one D-glucopyranosyl unit is substituted by a substituent of the formula $-O-(CH_2)_n-S-B_{12}H_{11}^{2-}$ wherein n is in the range of 3 to 10; and the dextran derivative is bound to the anti-EGFR antibody or an EGFR1 binding fragment thereof via a bond formed by a reaction between at least one aldehyde group formed by oxidative cleavage of a D-glucopyranosyl unit of the dextran derivative and an amino group of the anti-EGFR1 antibody or an EGFR1 binding fragment thereof.

14 Claims, 13 Drawing Sheets

Specification includes a Sequence Listing.

(56) References Cited

U.S. PATENT DOCUMENTS

| | | |
|---|---|---|
| 7,405,183 B2 | 7/2008 | Hanes, Jr. |
| 9,345,782 B2 | 5/2016 | Strand et al. |
| 9,439,985 B2 | 9/2016 | Magneson et al. |
| 2003/0068322 A1 | 4/2003 | Hansen |
| 2005/0152906 A1* | 7/2005 | Levanon ............ C07K 16/2896 424/155.1 |
| 2006/0024317 A1 | 2/2006 | Boyd et al. |
| 2006/0074008 A1 | 4/2006 | Senter et al. |
| 2006/0140858 A1 | 6/2006 | Goldenberg et al. |
| 2008/0241102 A1 | 10/2008 | Hersel et al. |
| 2009/0291885 A1 | 11/2009 | Sullivan et al. |
| 2010/0272639 A1 | 10/2010 | Dutcher |
| 2011/0053848 A1 | 3/2011 | Cleemann et al. |
| 2011/0104052 A1 | 5/2011 | Barnett et al. |
| 2014/0179877 A1 | 6/2014 | Nilsson et al. |
| 2014/0286862 A1 | 9/2014 | Strand et al. |
| 2015/0017246 A1 | 1/2015 | Huang |
| 2015/0031832 A1 | 1/2015 | Davis et al. |
| 2015/0057221 A1 | 2/2015 | Cleemann et al. |
| 2015/0166659 A1 | 6/2015 | Goldenberg et al. |
| 2015/0238625 A1 | 8/2015 | Hersel et al. |

FOREIGN PATENT DOCUMENTS

| | | |
|---|---|---|
| WO | WO 1989/010140 A1 | 11/1989 |
| WO | WO 1992/019273 A1 | 11/1992 |
| WO | WO 1996/014073 A1 | 5/1996 |
| WO | WO 1996/040245 A1 | 12/1996 |
| WO | WO 1997/029114 A1 | 8/1997 |
| WO | WO 1997/041898 A1 | 11/1997 |
| WO | WO 1998/004917 A1 | 2/1998 |
| WO | WO 2002/026262 A2 | 4/2002 |
| WO | WO 2003/068144 A2 | 8/2003 |
| WO | WO 2003/086312 A2 | 10/2003 |
| WO | WO 2007/011968 A2 | 1/2007 |
| WO | WO 2012/153193 A2 | 11/2012 |
| WO | WO 2013/012961 A2 | 1/2013 |
| WO | WO 2013/061083 A2 | 5/2013 |
| WO | WO 2014/096551 A1 | 6/2014 |
| WO | WO 2014/177771 * | 11/2014 |

OTHER PUBLICATIONS

Andersson et al. (1992) Effects of EGF-dextran-tyrosine-131I conjugates on the clonogenic survival of cultured glioma cells. J Neurooncol. 14(3):213-223.
Arie JP et al. (2001) Chaperone function of FkpA, a heat shock prolyl isomerase, in the periplasm of *Escherichia coli*. Mol Microbiol. 39(1):199-210.
Bachmann BJ (1987). Derivations and genotypes of some mutant derivatives of *Escherichia coli* K-12. p. 1191-1219, In: J. L. Ingraham, K. B. Low, B. Magasanik, M. Schaechter, and H. E. Umbarger (eds.), *Escherichia coli* and *Salmonella typhimurium*: cellular and molecular biology. American Society for Microbiology, Washington, D.C.
Backer MV et al. (2005) Vascular endothelial growth factor selectively targets boronated dendrimers to tumor vasculature. Mol Cancer Ther. 4(9):1423-9.
Bai R et al. (2009) Intracellular activation and deactivation of tasidotin, an analog of dolastatin 15: correlation with cytotoxicity. Mol Pharmacol. 75(1):218-26.
Barth RF et al. (1989) Conjugation, purification and characterization of boronated monoclonal antibodies for use in neutron capture therapy. Strahlenther Onkol. 165(2-3):142-5.
Barth RF et al. (1990) Boron neutron capture therapy of cancer. Cancer Res. 50(4):1061-70.
Barth RF et al. (2002) Molecular targeting of the epidermal growth factor receptor for neutron capture therapy of gliomas. Cancer Res. 62(11):3159-66.
Barth RF et al. (2004) Neutron capture therapy of epidermal growth factor (+) gliomas using boronated cetuximab (IMC-C225) as a delivery agent. Appl Radiat Isot. 61(5):899-903.

Barth RF et al. (2005) Boron neutron capture therapy of cancer: current status and future prospects. Clin Cancer Res. 11(11):3987-4002.
Barth RF et al. (2012) Current status of boron neutron capture therapy of high grade gliomas and recurrent head and neck cancer. Radiat Oncol. 7:146.
Bothmann H and Pluckthun A. (2000) The periplasmic *Escherichia coli* peptidylprolyl cis,trans-isomerase FkpA. I. Increased functional expression of antibody fragments with and without cis-prolines. J Biol Chem. 275(22):17100-5.
Brich Z et al. (1992) Preparation and characterization of a water soluble dextran immunoconjugate of doxorubicin and the monoclonal antibody (ABL 364) J Controlled Release 19(1-3):245-257.
Capala J et al. (1996) Boronated epidermal growth factor as a potential targeting agent for boron neutron capture therapy of brain tumors. Bioconjug Chem. 7(1):7-15.
Carlsson et al. (1994) Strategy for boron neutron capture therapy against tumor cells with over-expression of the epidermal growth factor-receptor. Int J Radiat Oncol Biol Phys. 30(1):105-115.
Carlsson et al. (1999) Conjugate Chemistry and Cellular Processing of EGF-Dextran. Acta Oncologica 38(3):313-321.
Chau Y et al. (2004) Synthesis and characterization of dextran-peptide-methotrexate conjugates for tumor targeting via mediation by matrix metalloproteinase II and matrix metalloproteinase IX. Bioconjug Chem, 15:931-41.
Chauhan SS et al. (2003) Reduced endocytosis and altered lysosome function in cisplatin-resistant cell lines. Br J Cancer. 88(8):1327-34.
Chen J et al. (1999) Chaperone activity of DsbC. J Biol Chem. 274(28):19601-5.
Chester MA. (1998) IUPAC-IUB Joint Commission on Biochemical Nomenclature (JCBN). Nomenclature of glycolipids—recommendations 1997. Eur J Biochem. 257(2):293-8.
Dosio F et al. (2011) Immunotoxins and anticancer drug conjugate assemblies: the role of the linkage between components. Toxins (Basel). 3(7):848-83.
Dubowchik GM et al. (2002) Cathepsin B-labile dipeptide linkers for lysosomal release of doxorubicin from internalizing immunoconjugates: model studies of enzymatic drug release and antigen-specific in vitro anticancer activity, Bioconjug Chem, 13:855-869.
Finnish Search Report for Finnish Patent Application No. FI 20135451 dated Feb. 28, 2014.
Finnish Search Report for Finnish Patent Application No. FI 20145552 dated Feb. 13, 2015.
Friedlander E et al. (2007) ErbB-directed immunotherapy: Antibodies in current practice and promising new agents, Immunol Letters, 116(2):126-140.
Gabel and Walczyna (1982) B-Decachloro-o-carborane Derivatives suitable for the preparation of boron-labeled biological macromolecules. Z Naturforsch C. 37(10):1038-1039.
Gedda L et al. (1996) Development and in vitro studies of epidermal growth factor-dextran conjugates for boron neutron capture therapy. Bioconjug Chem. 7(5):584-91.
Goldenberg DM et al. (1984) Neutron-capture therapy of human cancer: in vivo results on tumor localization of boron-10-labeled antibodies to carcinoembryonic antigen in the GW-39 tumor model system. 28. Proc Natl Acad Sci U S A. 81(2):560-3.
Guan L et al. (1998) Homogeneous immunoconjugates for boron neutron-capture therapy: design, synthesis, and preliminary characterization. Proc Natl Acad Sci U S A. 95(22):13206-10.
Hara H et al. (1996) Overproduction of penicillin-binding protein 7 suppresses thermosensitive growth defect at low osmolarity due to an spr mutation of *Escherichia coli*. Microb Drug Resist. Spring;2(1):63-72.
Hartman T and Carlsson J. (1994) Radiation dose heterogeneity in receptor and antigen mediated boron neutron capture therapy. Radiother Oncol. 31(1):61-75.
Hawthorne MF et al. (1972) Preparation of tumor-specific boron compounds. 1. In vitro studies using boron-labeled antibodies and elemental boron as neutron targets. J Med Chem. 15(5):449-52.
Hawthorne MF and Lee MW. (2003) A critical assessment of boron target compounds for boron neutron capture therapy. J Neurooncol. 62(1-2):33-45.

(56) References Cited

OTHER PUBLICATIONS

Holmberg A and Meurling L. (1993) Preparation of sulfhydrylborane-dextran conjugates for boron neutron capture therapy. Bioconjug Chem. 4(6):570-3.
International Search Report for International Patent Application No. PCT/FI2015/050422 dated Nov. 30, 2015.
International Preliminary Report on Patentability for International Patent Application No. PCT/FI2015/050422 dated Dec. 15, 2016.
International Search Report for International Patent Application No. PCT/FI2015/050423 dated Sep. 30, 2015.
International Preliminary Report on Patentability for International Patent Application No. PCT/FI2015/050423 dated Dec. 15, 2016.
IUPAC (1998) Nomenclature of glycolipids. Carbohydrate Res. 312(4):167-175.
Kim EM et a. (2012) Dextran-conjugated vascular endothelial growth factor receptor antibody for in vivo melanoma xenografted mouse imaging. Cancer Biother Radiopharm. 27(2):141-8.
Kim et al. (2013) New strategy for selective and sensitive assay of cathepsin B using a dityrosine-based material, Anal Biochem, 435:166-173.
Laakso J et al. (2001) Atomic emission method for total boron in blood during neutron-capture therapy. Clin Chem. 47(10):1796-803.
Larsson B et al. (1984) Boron-loaded macromolecules in experimental physiology: tracing by neutron capture radiography. Phys Med Biol. 29(4):361-70.
Lohmuller et al. (2003) Toward Computer-Based Cleavage Site Prediction of Cysteine Endopeptidases, Biol. Chem., 384:899-909.
Marepally SR et al. (2013) Boronated carbohydrate derivatives as potential boron neutron capture therapy reagents. Future Med Chem. 5(6):693-704.
Masarova J et al. (2001) Optimization of Dextran and Mannan Dialdehydes Preparation and Examination of their Biospecific Interaction with Concanavalin. Chem. Pap. 55(2):130-135.
Byrne et al., "A tale of two specificities: bispecific antibodies for therapeutic and diagnostic applications," Trends in Biotechnology Nov. 2013, vol. 31, No. 11.
Delord et al., "Open-label, multicentre expansion cohort to evaluate imgatuzumab in pre-treated patients with KRAS-mutant advanced colorectal carcinoma," European Journal of Cancer, vol. 50, Issue 3, Feb. 2014, pp. 496-505.
International Nonproprietary Names for Pharmaceutical Substances (INN), WHO Drug Information vol. 23, No. 3, 2009.
International Nonproprietary Names for Pharmaceutical Substances (INN), WHO Drug Information, vol. 26, No. 2, 2012.
Kettleborough et al. "Humanization of a mouse monoclonal antibody by CDR-grafting: the importance of framework residues on loop conformation," Protein Engineering, Design and Selection, vol. 4, Issue 7, Oct. 1, 1991, pp. 773-783.
Kontermann et al., "Dual targeting strategies with bispecific antibodies," mAbs, 4:2, 182-197.
Leach, "First-Line Necitumumab Improves Survival in Metastatic SquamousNSCLC," http://www.onclive.com/web-exclusives/first-line-necitumumab-improves-survival-in-metastatic-squamous-nsclc, Published Online: Tuesday, Aug. 13, 2013.
Mateo et al., "Humanization of a mouse monoclonal antibody that blocks the epidermal growth factor receptor: recovery of antagonistic activity," Immunotechnology, vol. 3, Issue 1, Mar. 1997, pp. 71-81.
PubChem SID: 135626739, External ID: D10018, Source: KEGG, Drug: Necitumumab, Available Date: Apr. 5, 2012.
PubChem SID: 135626751, External ID: D10031, Source: KEGG, Drug: Zalutumumab, Available Date: Apr. 5, 2012.
PubChem SID: 172232532, External ID: D10439, Source: KEGG, Drug: Imgatuzumab, Available Date: Feb. 14, 2014.
Ramakrishnan et al., "Nimotuzumab, a promising therapeutic monoclonal for treatment of tumors of epithelial origin," mAbs, 1:1, 41-48 (2009).

Rodeck et al. "Tumor Growth Modulation by a Monoclonal Antibody to the Epidermal Growth Factor Receptor: Immunologically Mediated and Effector Cell-independent Effects," Cancer Research 47, 3692-3696, Jul. 15, 1987.
Rowinsky et al., "Safety, Pharmacokinetics, and Activity of ABX-EGF, a Fully Human Anti-Epidermal Growth Factor Receptor Monoclonal Antibody in Patients With Metastatic Renal Cell Cancer," Journal of Clinical Oncology, vol. 22, No. 15, 2004.
Schick et al. "Zalutumumab in head and neck cancer," Expert Opin. Biol. Ther. (2012) 12(1):119-125.
Vanhoefer et al., "Phase I Study of the Humanized Antiepidermal Growth Factor Receptor Monoclonal Antibody EMD72000 in Patients With Advanced Solid Tumors That Express the Epidermal Growth Factor Receptor," Journal of Clinical Oncology, vol. 22, No. 1, 2004.
Yang et al., "Development of ABX-EGF, a fully human anti-EGF receptor monoclonal antibody, for cancer therapy," Critical Reviews in Oncology:Hematology 38 (2001) 17-23.
Yang et al., Eradication of Established Tumors by a Fully Human Monoclonal Antibody to the Epidermal Growth Factor Receptor without Concomitant Chemotherapy, Cancer Research 59, 1236-1243, Mar. 15, 1999.
Yang et al., Single Chain Epidermal Growth Factor Receptor Antibody Conjugated Nanoparticles for in vivo Tumor Targeting and Imaging, NIH Public Access Author Manuscript, Feb. 2009; 5(2): 235-243.
Matsunaga K et al. (2005) Technetium labeling of dextran incorporating cysteamine as a ligand. Nucl Med Biol. 32(3):279-85.
McNaught AD. (1997) International Union of Pure and Applied Chemistry and International Union of Biochemistry and Molecular Biology. Joint Commission on Biochemical Nomenclature. Nomenclature of carbohydrates. Carbohydr Res. 297(1):1-92.
Mehta and Lu (1996) Targeted drug delivery for boron neutron capture therapy. Pharm Res. 13(3):344-51.
Mehvar R. (2000) Dextrans for targeted and sustained delivery of therapeutic and imaging agents. J Control Release. 69(1):1-25.
Mehvar R. (2003) Recent trends in the use of polysaccharides for improved delivery of therapeutic agents: pharmacokinetic and pharmacodynamic perspectives. Curr Pharm Biotechnol. 4(5):283-302.
Melton RG et al. (1987) Covalent linkage of carboxypeptidase G2 to soluble dextrans—I. Properties of conjugates and effects on plasma persistence in mice. Biochem Pharmacol. 36(1):105-12.
Meo CD et al. (2007) Hyaluronan as carrier of carboranes for tumor targeting in boron neutron capture therapy. Biomacromolecules. 8(2):552-9.
Mizusawa E et al. (1982) Neutron-capture therapy of human cancer: in vitro results on the preparation of boron-labeled antibodies to carcinoembryonic antigen. Proc Natl Acad Sci U S A. 79(9):3011-4.
Mohammad RM et al. (1999) A new tubulin polymerization inhibitor, auristatin PE, induces tumor regression in a human Waldenstrom's macroglobulinemia xenograft model. Int J Oncol. 15(2):367-72.
Nodake Y et al. (2010) Reduction of the immunogenicity of beta-lactoglobulin from cow's milk by conjugation with a dextran derivative. Biosci Biotechnol Biochem. 74(4):721-6.
Novick S et al. (2002) Linkage of boronated polylysine to glycoside moieties of polyclonal antibody; boronated antibodies as potential delivery agents for neutron capture therapy. Nucl Med Biol. 29(2):159-67.
Nwe K et al. (2012) Preparation of cystamine core dendrimer and antibody-dendrimer conjugates for MRI angiography. Mol Pharm. 9(3):374-81.
Olsson P et al. (1994) Internalization and excretion of epidermal growth factor-dextran-associated radioactivity in cultured human squamous-carcinoma cells. Int J Cancer. 56(4):529-37.
Olsson P et al. (1998) Uptake of a boronated epidermal growth factor-dextran conjugate in CHO xenografts with and without human EGF-receptor expression. Anticancer Drug Des. 13(4):279-89.
Pak RH et al. (1995) Preparation and properties of nido-carborane-specific monoclonal antibodies for potential use in boron neutron capture therapy for cancer. Proc Natl Acad Sci U S A. 92(15):6986-90.

(56) References Cited

OTHER PUBLICATIONS

Pettersson ML et al. (1989) In vitro immunological activity of a dextran-boronated monoclonal antibody. Strahlenther Onkol. 165(2-3):151-2.

Pettersson ML et al. (1990) Immunoreactivity of boronated antibodies. J Immunol Methods. 126(1):95-102.

Pettit GR et al. (2011) Antineoplastic agents. 592. Highly effective cancer cell growth inhibitory structural modifications of dolastatin 10. J Nat Prod. 74(5):962-8.

Ramm K and Pluckthun A. (2000) The periplasmic *Escherichia coli* peptidylprolyl cis,trans-isomerase FkpA. II. Isomerase-independent chaperone activity in vitro. J Biol Chem. 275(22):17106-13.

Rillahan CD et al. (2012) Click and pick: identification of sialoside analogues for siglec-based cell targeting. Angew Chem Int Ed Engl. 51(44):11014-8.

Sammet B et al. (2012) Antibody-drug conjugates in tumor therapy. Pharm Pat Anal. 1(1):65-73.

Sjöström A et al. (1997) Binding, internalization and degradation of EGF-dextran conjugates in two human bladder-cancer cell lines. Int J Cancer. 70(4):383-9.

Shukla S et al. (2003) Synthesis and biological evaluation of folate receptor-targeted boronated PAMAM dendrimers as potential agents for neutron capture therapy. Bioconjug Chem. 14(1):158-67.

Siebenlist U et al. (1980) *E. coli* RNA polymerase interacts homologously with two different promoters. Cell. 20(2):269-81.

Smith RA (2009) A wortmannin-cetuximab as a double drug. Bioconjug Chem. 20(11):2185-9.

Stachowiak K et al. (2004) Fluorogenic peptide substrates for carboxypeptidase acticity of cathepsin B, Acta Biochimica Polonica, 51:81-92.

Takashina K et al. (1991) Comparative pharmacokinetic properties of murine monoclonal antibody A7 modified with neocarzinostatin, dextran and polyethylene glycol. Jpn J Cancer Res. 82(10):1145-50.

Tolmachev V et al. (1999) Closo-dodecaborate(2-) as a linker for iodination of macromolecules. Aspects on conjugation chemistry and biodistribution. Bioconjug Chem. 10(3):338-45.

Tolmachev V et al. (2004) Preparation, radioiodination and in vitro evaluation of a nido-carborane-dextran conjugate, a potential residualizing label for tumor targeting proteins and peptides. Journal of Radioanalytical and Nuclear Chemistry 261(1):107-112.

Ujeno Y et al. (1989) The enhancement of thermal-neutron induced cell death by 10-boron dextran. Strahlenther Onkol. 165(2-3):201-3.

Written Opinion of the International Searching Authority for International Patent Application No. PCT/FI2015/050422 dated Nov. 30, 2015.

Written Opinion of the International Searching Authority for International Patent Application No. PCT/FI2015/050423 dated Sep. 30, 2015.

Wu G et al. (2004) Site-specific conjugation of boron-containing dendrimers to anti-EGF receptor monoclonal antibody cetuximab (IMC-C225) and its evaluation as a potential delivery agent for neutron capture therapy. Bioconjug Chem. 15(1):185-94.

Wu G et al. (2006) Boron containing macromolecules and nanovehicles as delivery agents for neutron capture therapy. Anticancer Agents Med Chem. 6(2):167-84.

Wu G et al. (2007) Molecular targeting and treatment of an epidermal growth factor receptor-positive glioma using boronated cetuximab. Clin Cancer Res. 13(4):1260-8.

Yang W et al. (1997) Intratumoral delivery of boronated epidermal growth factor for neutron capture therapy of brain tumors. Cancer Res. 57(19):4333-9.

Yang W et al. (2002) Convection-enhanced delivery of boronated epidermal growth factor for molecular targeting of EGF receptor-positive gliomas. Cancer Res. 62(22):6552-8.

Yang W et al. (2004) Boronated epidermal growth factor as a delivery agent for neutron capture therapy of EGF receptor positive gliomas. Appl Radiat Isot. 61(5):981-5.

Yang W et al. (2006) Molecular targeting and treatment of EGFRvIII-positive gliomas using boronated monoclonal antibody L8A4. Clin Cancer Res. 12(12):3792-802.

Yang W et al. (2008) Molecular targeting and treatment of composite EGFR and EGFRvIII-positive gliomas using boronated monoclonal antibodies. Clin Cancer Res. 14(3):883-91.

Yang W et al. (2009a) Convection enhanced delivery of boronated EGF as a molecular targeting agent for neutron capture therapy of brain tumors. J Neurooncol. 95(3):355-65.

Yang W et al. (2009b) Boron neutron capture therapy of EGFR or EGFRvIII positive gliomas using either boronated monoclonal antibodies or epidermal growth factor as molecular targeting agents. Appl Radiat Isot. 67(7-8 Suppl): S328-31.

Zhao Q et al. (1997) Preparation and purification of an end to end coupled mEGF-dextran conjugate. Bioconjug Chem. 8(6):927-34.

Zhao Q et al. (1999) Effects of dextranation on the pharmacokinetics of short peptides. A PET study on mEGF. Bioconjug Chem. 10(6):938-46.

Zhang X and Mehvar R. (2001) Dextran-methylprednisolone succinate as a prodrug of methylprednisolone: plasma and tissue disposition, J Pharm Sci, 90:2078-87.

Zhou Q et al. (2014) Site-specific antibody-drug conjugation through glycoengineering. Bioconjug Chem. 25(3):510-20.

Zimmerman ES et al. (2014) Production of Site-Specific Antibody-Drug Conjugates Using Optimized Non-Natural Amino Acids in a Cell-Free Expression System Bioconjugate Chemistry 25(2):351-361.

\* cited by examiner

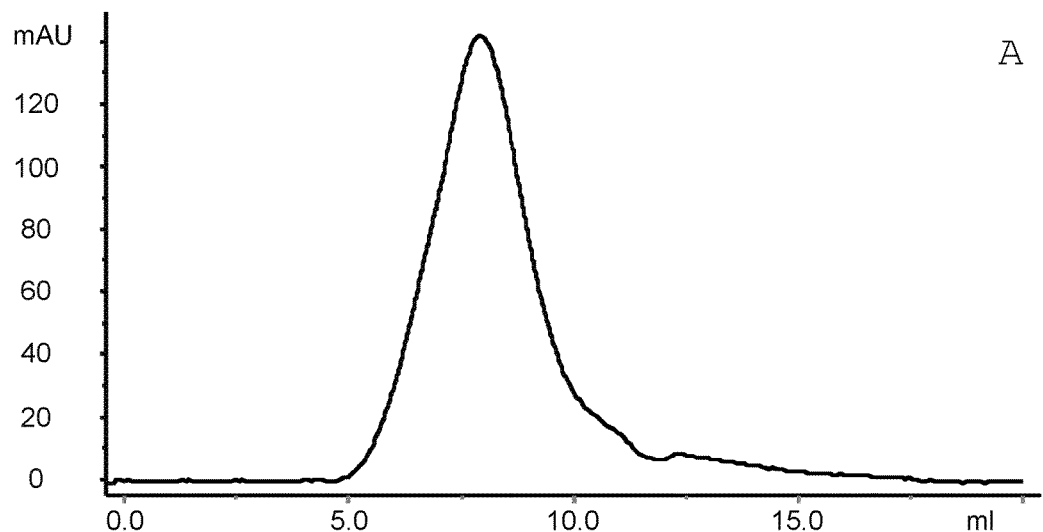
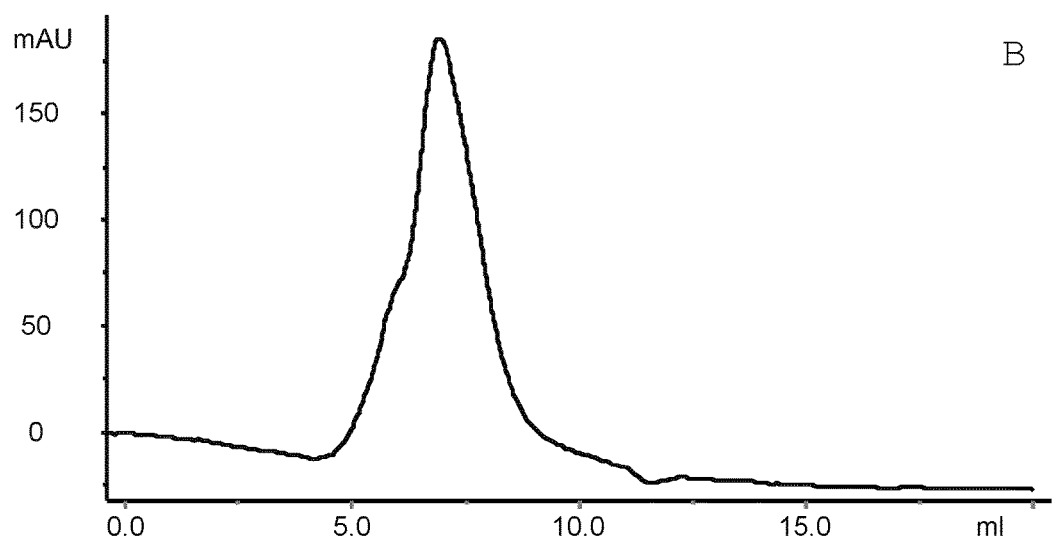
Fig. 2

CGAAAAATAATAAAGGGAAAATCAGTTTTTGATATCAAAATTATACATGTCAACGATAATACAAAAATATAATAC

AAACTATAAGATGTTATCAGTATTTATTATGCATTTAGAATAAATTTGTGTCGCCCTTAATTGTGAGCGGAT <u>T5 promoter</u>

AACAATTACGAGCTTCATGCACAGTGAAATCATGAAAAATTTATTTGCTTTGTGAGCGGATAACAATTATAAT <u>RBS</u>

ATGTGGAATTGTGAGCGGCTCACAATTCCACACAACGGTTTCCCCTCTAGAAATAATTTTGTTTAACTTTTAAGGAG <u>signal peptide</u> <u>CetFab HC</u>
ATAAAAATGAAAAAAACTGCTGTTCGGATTCCGGATTCCGGTGGTTCGCCGTTCTATAGCCATAGCCAGGTGCAGCTG AAACAGAGCGG...TAAAACCCATTAAGGATCCGAATTCAAGGAGATAAAAAATGAAAAAGACAGCTATCGCG <u>stop</u> <u>BamHI</u> <u>EcoRI</u> <u>RBS</u> <u>signal peptide</u>
<u>CetFab LC</u>
*ATTGCAGTGGGCACTGGCTGGTTTCGCTAGCGGCCAGGCCGATATTCGCTGACCCAG*...

Fig. 5

CONJUGATES COMPRISING AN ANTI-EGFR1 ANTIBODY

This application is filed under 35 U.S.C. § 371 and claims priority to International Application No. PCT/FI2015/050422 filed Jun. 12, 2015 and claims the benefit of FI 20145552 filed Jun. 13, 2014 and FI 20155114 filed Feb. 20, 2015; all of which are hereby incorporated by reference in their entirety.

FIELD OF THE INVENTION

The invention relates to a conjugate, a pharmaceutical composition and a method of treating or modulating the growth of EGFR1 expressing tumor cells in a human.

BACKGROUND OF THE INVENTION

Boron neutron capture therapy (BNCT) is a form of noninvasive therapy of malignant tumors such as primary brain tumors and head and neck cancer. In BNCT, a patient is injected with a drug which has the ability to localize in the tumor and which carries nonradioactive boron-10 atoms. When the drug is irradiated with low energy thermal neutrons, biologically destructive alpha particles and lithium-7 nuclei are emitted.

Drugs such as conjugates having a high content of boron-10 and capable of localizing specifically in the tumor are required for BNCT. Such conjugates should be easily produced, stable, soluble and safe. However, provision of such conjugates is complicated e.g. by that some types of chemistries do not appear to work with boron-10 containing compounds.

The purpose of the present invention is to provide conjugates that have improved properties as compared to known conjugates and that contain a high content of boron-10.

SUMMARY OF THE INVENTION

The conjugate according to the present invention can be characterized as a conjugate comprising an anti-EGFR1 antibody or an FGFR1 binding fragment thereof and at least one dextran derivative, wherein the dextran derivative comprises at least one D-glucopyranosyl unit, wherein at least one carbon selected from carbon 2, 3 or 4 of the at least one D-glucopyranosyl unit is substituted by a substituent of the formula $-O-(CH_2)_n-S-B_{12}H_{11}^{2-}$ wherein n is in the range of 3 to 10, and the dextran derivative is bound to the anti-EGFR1 antibody or an EGFR1 binding fragment thereof via a bond formed by a reaction between at least one aldehyde group formed by oxidative cleavage of a D-glucopyranosyl unit of the dextran derivative and an amino group of the anti-EGFR1 antibody or an EGFR1 binding fragment thereof.

The pharmaceutical composition according to the present invention can be characterized as a pharmaceutical composition comprising the conjugate used as a medicament.

The conjugate or pharmaceutical composition can be for use in the treatment of cancer.

The method of treating or modulating the growth of EGFR1 expressing tumor cells in a human can be characterized as administering the conjugate or the pharmaceutical composition to the human in an effective amount.

The prokaryotic host cell according to the present invention can be characterized as a prokaryotic host cell comprising one or more polynucleotides encoding i) a light chain variable region and ii) a heavy chain variable region of an anti-EGFR1 antibody or an EGFR1 binding fragment thereof.

The method for treating or modulating the growth of EGFR1 expressing tumor cells in a human can be characterized as a method for treating or modulating the growth of EGFR1 expressing tumor cells in a human, wherein the conjugate or the pharmaceutical composition is administered to a human in an effective amount.

The polynucleotide according to the present invention can be characterized as a polynucleotide encoding i) a light chain variable region and ii) a heavy chain variable region of an anti-EGFR1 antibody or an EGFR1 binding fragment thereof wherein the polynucleotide encoding a light chain variable region comprises or consists of the sequence set forth in SEQ ID NO: 8, or a sequence that is at least 90%, at least 91%, at least 92%, at least 93%, at least 94%, at least 95%, at least 96%, at least 97%, at least 98%, or at least 99% identical to SEQ ID NO: 8, and the polynucleotide encoding a heavy chain variable region comprises or consists of the sequence set forth in SEQ ID NO: 9, or a sequence that is at least 90%, at least 91%, at least 92%, at least 93%, at least 94%, at least 95%, at least 96%, at least 97%, at least 98%, or at least 99% identical to SEQ ID NO: 9; a polynucleotide encoding i) a light chain variable region and ii) a heavy chain variable region of an anti-EGFR1 antibody or an EGFR1 binding fragment thereof wherein the polynucleotide comprises or consists of the light chain sequence set forth in SEQ ID NO: 10, or a sequence that is at least 90%, at least 91%, at least 92%, at least 93%, at least 94%, at least 95%, at least 96%, at least 97%, at least 98%, or at least 99% identical to SEQ ID NO: 10, and the heavy chain sequence set forth in SEQ ID NO: 11, or a sequence that is at least 90%, at least 91%, at least 92%, at least 93%, at least 94%, at least 95%, at least 96%, at least 97%, at least 98%, or at least 99% identical to SEQ ID NO: 11, a polynucleotide encoding i) a light chain variable region and ii) a heavy chain variable region of an anti-EGFR1 antibody or an EGFR1 binding fragment thereof wherein the polynucleotide comprises or consists of the sequence set forth in SEQ ID NO: 12, or a sequence that is at least 90%, at least 91%, at least 92%, at least 93%, at least 94%, at least 95%, at least 96%, at least 97%, at least 98%, or at least 99% identical to SEQ ID NO: 12; or a polynucleotide encoding i) a light chain variable region and ii) a heavy chain variable region of an anti-EGFR1 antibody or an EGFR1 binding fragment thereof wherein the polynucleotide comprises or consists of the sequence set forth in SEQ ID NO: 13, or a sequence that is at least 90%, at least 91%, at least 92%, at least 93%, at least 94%, at least 95%, at least 96%, at least 97%, at least 98%, or at least 99% identical to SEQ ID NO: 13.

BRIEF DESCRIPTION OF THE DRAWINGS

The accompanying drawings, which are included to provide a further understanding of the invention and constitute a part of this specification, illustrate embodiments of the invention and together with the description help to explain the principles of the invention. In the drawings:

FIG. 2. Gel filtration analysis of BSH-Dex-conjugates. A. Anti-EGFR1-Fab-BSH(800B)-Dex. Conjugate elutes at 7.8 ml when analysed with Yarra SEC-3000 gel filtration column. By comparison anti-EGFR1-Fab elutes at 9.1 ml. B. Anti-EGFR1-Fab2-BSH(800B)-Dex. Conjugate elutes at 6.9 ml when analysed with Yarra SEC-3000 gel filtration column. By comparison anti-EGFR1-Fab2 elutes at 8.4 ml.

FIG. 5. An example of the vector setup for signal peptide optimization. T5 promoter, ribosome binding sites (RBS), signal peptides and anti-EGFR1 Fab heavy- and light chain sequences identified.

DETAILED DESCRIPTION

Figure 1:
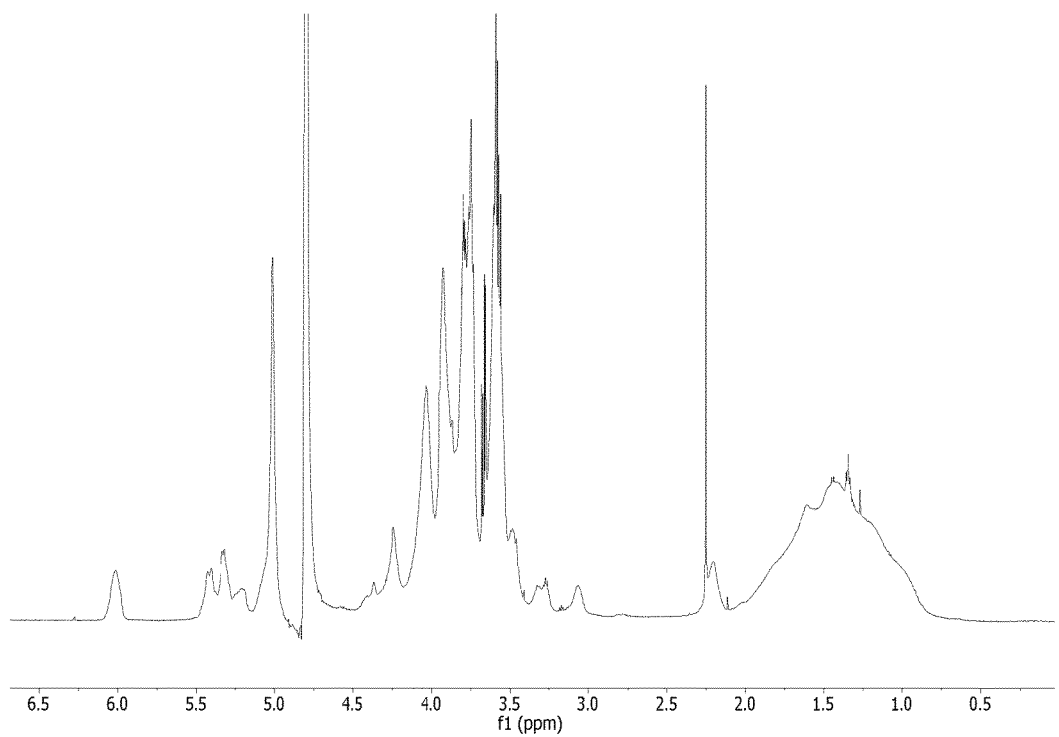
FIG. 1. Proton-NMR spectrum of BSH-dextran. The boron linked protons resonate between 0.8-2.0 ppm, and the boron load of BSH-dextran can be estimated by comparing the integral of boron-protons to the integral of dextran protons. Unreacted allyl groups yield signals at 4.22, 5.29, 5.39 and 5.99 ppm. Sharp signal at 2.225 ppm is acetone (internal standard).

The present invention relates to a conjugate comprising an anti-EGFR1 antibody or an EGFR1 binding fragment thereof and at least one dextran derivative, wherein
the dextran derivative comprises at least one D-glucopyranosyl unit, wherein at least one carbon selected from carbon 2, 3 or 4 of the at least one D-glucopyranosyl unit is substituted by a substituent of the formula

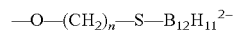
—O—(CH$_2$)$_n$—S—B$_{12}$H$_{11}$$^{2-}$ wherein n is in the range of 3 to 10; and
the dextran derivative is bound to the anti-EGFR1 antibody or an EGFR1 binding fragment thereof via a bond formed by a reaction between at least one aldehyde group formed by oxidative cleavage of a D-glucopyranosyl unit of the dextran derivative and an amino group of the anti-EGFR1 antibody or an EGFR1 binding fragment thereof.

The conjugate is suitable for use in boron neutron capture therapy. "Boron neutron capture therapy" (BNCT) should be understood as referring to targeted radiotherapy, wherein nonradioactive boron-10 is irradiated with low energy thermal neutrons to yield biologically destructive alpha particles and lithium-7 nuclei. The nonradioactive boron-10 may be targeted by incorporating it in a tumor localizing drug such as a tumor localizing conjugate.

"EGFR1" herein should be understood as referring to human epidermal growth factor receptor 1 (EGFR1) having a sequence set forth in SEQ ID NO: 1.

"Anti-EGFR1 antibody" should be understood as referring to an antibody that specifically binds EGFR1. The term "specifically binding" refers to the ability of the antibody to discriminate between EGFR1 and any other protein to the extent that, from a pool of a plurality of different proteins as potential binding partners, only EGFR1 is bound or significantly bound. As examples only, specific binding and/or kinetic measurements may be assayed by e.g. by utilizing surface plasmon resonance-based methods on a Biacore apparatus, by immunological methods such as ELISA or by e.g. protein microarrays.

"An EGFR1 binding fragment thereof" should be understood as referring to any fragment of an anti-EGFR1 antibody that is capable of specifically binding EGFR1.

In an embodiment, anti-EGFR1 antibody is cetuximab, imgatuzumab, matuzumab, nimotuzumab, necitumumab, panitumumab, or zalutumumab.

In an embodiment, the anti-EGFR1 antibody is cetuximab.

In an embodiment, cetuximab has a sequence set forth in SEQ ID NOs: 2 and 3.

In an embodiment, cetuximab comprises or consists of the sequences set forth in SEQ ID NOs: 2 and 3.

In an embodiment, the anti-EGFR1 antibody is nimotuzumab.

In an embodiment, nimotuzumab has a sequence set forth in SEQ ID NOs: 4 and 5.

In an embodiment, nimotuzumab comprises or consists of the sequences set forth in SEQ ID NOs: 4 and 5.

An anti-EGFR1 antibody may be e.g. an scFv, a single domain antibody, an Fv, a VHH antibody, a diabody, a tandem diabody, a Fab, a Fab', a F(ab')$_2$, a Db, a dAb-Fc, a taFv, a scDb, a dAb$_2$, a DVD-Ig, a Bs(scFv)$_4$-IgG, a taFv-Fc, a scFv-Fc-scFv, a Db-Fc, a scDb-Fc, a scDb-C$_H$3, or a dAb-Fc-dAb. Furthermore, the anti-EGFR1 antibody or an EGFR1 binding fragment thereof may be present in monovalent monospecific, multivalent monospecific, bivalent monospecific, or multivalent multispecific forms.

In an embodiment, the anti-EGFR1 antibody is a human antibody or a humanized antibody. In this context, the term "human antibody", as it is commonly used in the art, is to be understood as meaning antibodies having variable regions in which both the framework and complementary determining regions (CDRs) are derived from sequences of human origin. In this context, the term "humanized antibody", as it is commonly used in the art, is to be understood as meaning antibodies wherein residues from a CDR of an antibody of human origin are replaced by residues from a CDR of a nonhuman species (such as mouse, rat or rabbit) having the desired specificity, affinity and capacity.

In an embodiment, the anti-EGFR1 antibody fragment comprises a Fab fragment of cetuximab. In an embodiment, the anti-EGFR1 Fab fragment has a sequence set forth in SEQ ID NOs: 6 and 3. In an embodiment, the anti-EGFR1 Fab fragment comprises or consists of a sequence set forth in SEQ ID NOs: 6 and 3.

In an embodiment, the anti-EGFR1 antibody comprises a F(ab')2 fragment of cetuximab. In an embodiment, the anti-EGFR1 F(ab')2 fragment has a sequence set forth in SEQ ID NOs: 7 and 3. In an embodiment, the anti-EGFR1 F(ab')2 fragment comprises or consists of a sequence set forth in SEQ ID NOs: 7 and 3.

"Dextran" should be understood as referring to a branched glucan composed of chains of varying lengths, wherein the straight chain consists of a α-1,6 glycosidic linkages between D-glucopyranosyl units. Branches are bound via α-1,3 glycosidic linkages and, to a lesser extent, via α-1,2 and/or α-1,4 glycosidic linkages. A portion of a straight chain of a dextran molecule is depicted in the schematic representation below.

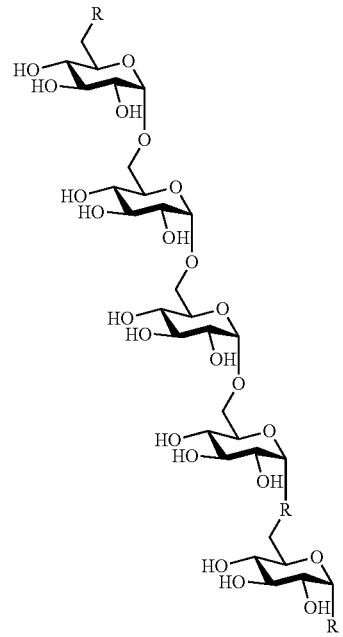

"D-glucopyranosyl unit" should be understood as referring to a single D-glucopyranosyl molecule. Dextran thus comprises a plurality of D-glucopyranosyl units. In dextran, each D-glucopyranosyl unit is bound to at least one other D-glucopyranosyl unit via a α-1,6 glycosidic linkage, via a α-1,3 glycosidic linkage or via both.

Each D-glucopyranosyl unit of dextran comprises 6 carbon atoms, which are numbered 1 to 6 in the schematic representation below. The schematic representation shows a single D-glucopyranosyl unit bound to two other D-glucopyranosyl units (not shown) via α-1,6 glycosidic linkages.

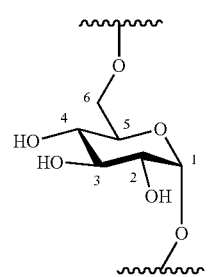

Carbons 2, 3 and 4 may contain free hydroxyl groups. In D-glucopyranosyl units bound to a second D-glucopyranosyl unit via a α-1,3 glycosidic linkage, wherein carbon 3 of the D-glucopyranosyl unit is bound via an ether bond to carbon 1 of the second D-glucopyranosyl unit, carbons 2 and 4 may be substituted by free hydroxyl groups. In D-glucopyranosyl units bound to a second D-glucopyranosyl unit via a α-1,2 or α-1,4 glycosidic linkage, wherein carbon 2 or 4 of the D-glucopyranosyl unit is bound via an ether bond to carbon 1 of the second D-glucopyranosyl unit, carbons 3 and 4 or 2 and 3, respectively, may be substituted by free hydroxyl groups.

Carbohydrate nomenclature is essentially according to recommendations by the IUPAC-IUB Commission on Biochemical Nomenclature (e.g. Carbohydrate Res. 1998, 312, 167; Carbohydrate Res. 1997, 297, 1; Eur. J. Biochem. 1998, 257, 293).

The term "dextran derivative" should be understood as referring to dextran, wherein at least one carbon selected from carbon 2, 3 or 4 of the at least one D-glucopyranosyl unit is substituted by a substituent of the formula $$-O-(CH_2)_n-S-B_{12}H_{11}{}^{2-}$$

wherein n is in the range of 3 to 10; and
the dextran derivative is bound to the anti-EGFR1 antibody or an EGFR1 binding fragment thereof via a bond formed by a reaction between at least one aldehyde group formed by oxidative cleavage of a D-glucopyranosyl unit of the dextran derivative and an amino group of the anti-EGFR1 antibody or an EGFR1 binding fragment thereof. The dextran derivative may further contain other modifications to the basic dextran structure, e.g. as described below.

"BSH", "$B_{12}H_{11}$—SH" and "$Na_2B_{12}H_{11}SH$" should be understood as referring to sodium borocaptate, also known as sodium mercaptododecaborate and sulfhydryl boron hydride. "$B_{12}H_{11}{}^{2-}$" thus refers to the boron hydride moiety of BSH.

One or more, i.e. one, two or three carbons selected from carbons 2, 3 and 4 of the at least one D-glucopyranosyl unit may be substituted by a substituent of the formula —O—$(CH_2)_n$—S—$B_{12}H_{11}{}^{2-}$.

In an embodiment, n is 3, 4, 5, 6, 7, 8, 9 or 10. In an embodiment, n is in the range of 3 to 4, or in the range of 3 to 5, or in the range of 3 to 6, or in the range of 3 to 7, or in the range of 3 to 8, or in the range of 3 to 9.

D-glucopyranosyl units of dextran may be cleaved by oxidative cleavage of a bond between two adjacent carbons substituted by a hydroxyl group. The oxidative cleavage cleaves vicinal diols, i.e. D-glucopyranosyl units in which two (free) hydroxyl groups occupy vicinal positions. D-glucopyranosyl units in which carbons 2, 3 and 4 contain free hydroxyl groups may thus be oxidatively cleaved between carbons 2 and 3 or carbons 3 and 4. Thus a bond selected from the bond between carbons 2 and 3 and the bond between carbons 3 and 4 may be oxidatively cleaved. D-glucopyranosyl units of dextran may be cleaved by oxidative cleavage using an oxidizing agent such as sodium periodate, periodic acid and lead(IV) acetate, or any other oxidizing agent capable of oxidatively cleaving vicinal diols.

Oxidative cleavage of a D-glucopyranosyl unit forms two aldehyde groups, one aldehyde group at each end of the chain formed by the oxidative cleavage. In the conjugate, the aldehyde groups may in principle be free aldehyde groups. However, the presence of free aldehyde groups in the conjugate is typically undesirable. Therefore the free aldehyde groups may be capped or reacted with an amino group of the anti-EGFR1 antibody or an EGFR1 binding fragment thereof, or e.g. with a tracking molecule.

The dextran derivative is bound to the anti-EGFR1 antibody or an EGFR1 binding fragment thereof via a bond formed by a reaction between at least one aldehyde group formed by oxidative cleavage of a D-glucopyranosyl unit of the dextran derivative and an amino group of the anti-EGFR1 antibody or an EGFR1 binding fragment thereof.

The dextran derivative may also be bound to the anti-EGFR1 antibody or an EGFR1 binding fragment thereof via a group formed by a reaction between at least one aldehyde group formed by oxidative cleavage of a D-glucopyranosyl unit of the dextran derivative and an amino group of the anti-EGFR1 antibody or an EGFR1 binding fragment thereof.

The aldehyde group formed by oxidative cleavage readily reacts with an amino group in solution, such as an aqueous solution. The resulting group or bond formed may, however, vary and is not always easily predicted and/or characterised. The reaction between at least one aldehyde group formed by oxidative cleavage of a D-glucopyranosyl unit of the dextran derivative and an amino group of the anti-EGFR1 antibody or an EGFR1 binding fragment thereof may result e.g. in the formation of a Schiff base. Thus the group via which the dextran derivative is bound to the anti-EGFR1 antibody or an EGFR1 binding fragment thereof may be e.g. a Schiff base (imine) or a reduced Schiff base (secondary amine).

In an embodiment, the dextran derivative has a molecular mass in the range of about 3 to about 2000 kDa. In this context, the molecular mass of the dextran derivative should be understood as including the molecular mass of the dextran derivative containing the dextran and its substituents, but not the molecular mass of the anti-EGFR1 antibody or an EGFR1 binding fragment thereof. In an embodiment, the dextran derivative has a molecular mass in the range of about 30 to about 300 kDa.

In an embodiment, the conjugate comprises about 10 to about 300 or about 20 to about 150 substituents of the formula —O—$(CH_2)_n$—S—$B_{12}H_{11}{}^{2-}$.

In an embodiment, the conjugate comprises about 300 boron atoms (300B), about 800 boron atoms (800B), about 900 boron atoms (900B), or about 1200 boron atoms. E.g "900B" refers to a conjugate carrying per one mole of protein one mole of dextran, that carries ca. 900 moles of boron atoms in BSH molecules.

The anti-EGFR1 antibody or an EGFR1 binding fragment thereof typically contains at least one amino group, such as an N-terminal amine group and/or the amino group of a lysine residue.

In an embodiment, the amino group of the anti-EGFR1 antibody or an EGFR1 binding fragment thereof is the amino group of a lysine residue of the anti-EGFR1 antibody or an EGFR1 binding fragment thereof.

In an embodiment, the conjugate further comprises at least one tracking molecule bound to the dextran derivative or to the anti-EGFR1 antibody or an EGFR1 binding fragment thereof.

"Tracking molecule" refers to a detectable molecule. Such a detectable molecule may be e.g. a radioisotope, such as $^{14}C$, a compound comprising a radioisotope, a radionuclide, a compound comprising a radionuclide, a fluorescent label molecule (such as FITC, TRITC, the Alexa and Cy dyes, etc.), a chelator, such as DOTA (1,4,7,10-tetraazacyclododecane-1,4,7,10-tetraacetic acid), or an MRI active molecule, such as gadolinium-DTPA (gadolinium-diethylenetriaminepentacetate). Procedures for accomplishing the binding of the tracking molecule to the dextran derivative or to the anti-EGFR1 antibody or an EGFR1 binding fragment thereof are well known to the art. A tracking molecule may allow for locating the conjugate after it has been administered to a patient and targeted to specific cells; in this way, it is possible to direct the low energy thermal neutron irradiation to the location of the targeted conjugate.

In an embodiment, the tracking molecule is bound to the dextran derivative via a bond or a group formed by a reaction between at least one aldehyde group formed by oxidative cleavage of a D-glucopyranosyl unit of the dextran derivative and a group of the tracking molecule. A suitable group of the tracking molecule may be e.g. an amino group.

It is possible that one or more aldehyde groups formed by oxidative cleavage of a D-glucopyranosyl unit of the dextran derivative is not reacted with an amino group of the anti-EGFR1 antibody or an EGFR1 binding fragment thereof or with a tracking molecule.

In an embodiment, the dextran derivative comprises at least one aldehyde group formed by oxidative cleavage of a D-glucopyranosyl unit of the dextran derivative which is capped.

The at least one aldehyde group may be capped by a suitable group, such as a reduced Schiff base.

The at least one aldehyde group may also be capped by a group formed by a reaction between the at least one aldehyde group and a hydrophilic capping agent, such as ethanolamine, lysine, glycine or Tris.

In an embodiment, ethanolamine comprises $^{14}C$.

The capping may be stabilized using a reducing agent, such as $NaCNBH_3$. A capping group such as a reduced Schiff base may thus be formed.

In an embodiment, the dextran derivative comprises at least one aldehyde group formed by oxidative cleavage of a D-glucopyranosyl unit of the dextran derivative that is not reacted with an amino group of the anti-EGFR1 antibody or an EGFR1 binding fragment thereof or with a tracking molecule and which is capped.

In an embodiment, essentially all aldehyde groups formed by oxidative cleavage of one or more D-glucopyranosyl units of the dextran derivative are capped.

In an embodiment, the dextran derivative comprises a plurality of aldehyde groups formed by oxidative cleavage of a D-glucopyranosyl unit of the dextran derivative, wherein essentially all of the aldehyde groups formed by oxidative cleavage of one or more D-glucopyranosyl units of the dextran derivative are capped.

In an embodiment, at least one carbon selected from carbon 2, 3 or 4 of at least one D-glucopyranosyl unit of the dextran derivative is substituted by a substituent of the formula $$—O—(CH_2)_m CH=CH_2$$

wherein m is in the range of 1 to 8. While such an embodiment is typically not desirable, it may occur as a side product, when said substituent has not reacted with BSH.

In an embodiment, the conjugate is obtainable by a method comprising the steps of:

a) alkenylating at least one hydroxyl group of dextran to obtain alkenylated dextran;

b) reacting sodium borocaptate (BSH) with the alkenylated dextran obtainable from step a) to obtain BSH-dextran;

c) oxidatively cleaving at least one D-glucopyranosyl residue of the BSH-dextran so that aldehyde groups are formed;

d) reacting the oxidatively cleaved BSH-dextran obtainable from step c) with an anti-EGFR1 antibody or an EGFR1 binding fragment thereof to obtain a conjugate.

The present invention also relates to a conjugate obtainable by a method comprising the steps of:

a) alkenylating at least one hydroxyl group of dextran to obtain alkenylated dextran;

b) reacting sodium borocaptate (BSH) with the alkenylated dextran obtainable from step a) to obtain BSH-dextran;

c) oxidatively cleaving at least one D-glucopyranosyl residue of the BSH-dextran so that aldehyde groups are formed;

d) reacting the oxidatively cleaved BSH-dextran obtainable from step c) with an anti-EGFR1 antibody or an EGFR1 binding fragment thereof to obtain a conjugate.

In an embodiment, the dextran has a molecular mass in the range of about 3 to about 2000 kDa, or about 10 to about 100 kDa, or about 5 to about 200 kDa, or about 10 to about 250 kDa. The dextran having a molecular mass in said range should be understood as referring to dextran that has not been subjected to steps a)-d).

In this context, the term "alkenylation" or "alkenylating" should be understood as referring to the transfer of an alkenyl group to a D-glucopyranosyl unit of dextran to give an alkenyl ether. In other words, at least one hydroxyl group of the D-glucopyranosyl unit of dextran becomes an alkenyloxy group.

In step a), one or more of hydroxyl groups bound to carbons 2, 3 or 4 of at least one D-glucopyranosyl unit of dextran may react in the alkenylation reaction. One or more, or a plurality of, D-glucopyranosyl units of dextran may be alkenylated.

In an embodiment, dextran is alkenylated in step a) using an alkenylating agent, wherein the alkenylating agent has a structure according to the formula $$X—(CH_2)_m CH=CH_2$$

wherein m is in the range from 1 to 8, and X is Br, Cl, or I.

In an embodiment, m is 1, 2, 3, 4, 5, 6, 7 or 8. In an embodiment, m is in the range of 1 to 2, or in the range of 1 to 3, or in the range of 1 to 4, or in the range of 1 to 5, or in the range of 1 to 6, or in the range of 1 to 7.

In an embodiment, the alkenylating agent is allyl bromide.

In an embodiment, at least one carbon selected from carbon 2, 3 or 4 of at least one D-glucopyranosyl unit of the alkenylated dextran obtainable from step a) is substituted by a substituent of the formula $$—O—(CH_2)_m CH=CH_2,$$

wherein m is in the range of 1 to 8.

In an embodiment, m is 1, 2, 3, 4, 5, 6, 7 or 8. In an embodiment, m is in the range of 1 to 2, or in the range of 1 to 3, or in the range of 1 to 4, or in the range of 1 to 5, or in the range of 1 to 6, or in the range of 1 to 7.

In step b), the sulfhydryl group of BSH may react with an alkenyl group of the alkenylated dextran to form BSH-dextran to give a thioether. One or more BSH molecules may react with the alkenylated dextran. Therefore, BSH-dextran obtainable from step b) may contain a plurality of BSH moieties (i.e. groups of the formula $—S—B_{12}H_{11}^{2-}$). The sulfhydryl groups of BSH may react with alkenyl groups of a single alkenylated D-glucopyranosyl unit containing more than one alkenyl group or with alkenyl groups of two or more alkenylated D-glucopyranosyl units.

Thus the BSH-dextran obtainable from step b) may be a dextran derivative in which at least one carbon selected from carbon 2, 3 or 4 of the at least one D-glucopyranosyl unit is substituted by a substituent of the formula $$—O—(CH_2)_n—S—B_{12}H_{11}^{2-}$$

wherein n is in the range of 3 to 10.

In an embodiment, BSH-dextran obtainable from step b) comprises about 10 to about 100 or about 20 to 100 substituents or about 10 to about 300 or about 20 to about 150 of the formula $—O—(CH_2)_n—S—B_{12}H_{11}^{2-}$, wherein n is in the range of 3 to 10.

In an embodiment, BSH is reacted with the alkenylated dextran obtainable from step a) in the presence of a radical initiator in step b). The radical initiator is capable of catalyzing the reaction between the sulfhydryl group(s) of BSH and with the alkenyl group(s) of alkenylated dextran.

In this context, "radical initiator" should be understood as referring to an agent capable of producing radical species under mild conditions and promote radical reactions. The term "radical initiator" may also refer to UV (ultraviolet) light. UV light irradiation is capable of generating radicals, e.g. in the presence of a suitable photoinitiator. Suitable radical initiators include, but are not limited to, inorganic peroxides such as ammonium persulfate or potassium persulfate, organic peroxides, and UV light.

In an embodiment, BSH is reacted with the alkenylated dextran obtainable from step a) in the presence of a radical initiator selected from the group consisting of ammonium persulfate, potassium persulfate and UV light in step b).

In step b), the weight ratio or the molar ratio of BSH to alkenylated dextran obtainable from step a) may be suitably selected in order to obtain conjugates in which the number of BSH moieties (i.e. the number of substituents of the formula $—O—(CH_2)_n—S—B_{12}H_{11}^{2-}$) per dextran moiety (of the dextran derivative) varies. The number of BSH moieties per dextran moiety of the BSH-dextran may be measured e.g. by nuclear magnetic resonance as described in Example 2 or by inductively coupled plasma mass spectrometry (ICP-MS) as described in Example 9.

In an embodiment, the ratio of BSH to alkenylated dextran present in step b) is in the range of 1:5 to 2:1, or in the range of 1:4 to 1:1 by weight, or in the range of 1:2 to 3:4 by weight. Typically, the higher the ratio of BSH to alkenylated dextran, the higher the number of BSH moieties per dextran moiety of the BSH-dextran.

The ratio of the radical initiator, such as ammonium persulfate or potassium persulfate, may also be varied in step b). In an embodiment, the ratio of the radical initiator to BSH and/or to dextran present in step b) is in the range of 1:5 to 2:1, or in the range of 1:4 to 1:1 by weight, or in the range of 1:2 to 3:4 by weight.

In an embodiment, the ratio of the radical initiator to alkenylated dextran in step b) is in the range of 1:5 to 2:1, or in the range of 1:4 to 1:1 by weight, or in the range of 1:2 to 3:4 by weight.

As described above, a bond selected from the bond between carbons 2 and 3 and the bond between carbons 3 and 4 may be oxidatively cleaved in step c). In the oxidative cleavage, the D-glucopyranosyl ring is opened between vicinal diols, leaving two aldehyde groups. Aldehyde groups of the oxidatively cleaved BSH-dextran obtainable from step c) may react with an anti-EGFR1 antibody or an EGFR1 binding fragment thereof to obtain a conjugate. The aldehyde groups may react with a suitable group such as an amino group.

The at least one D-glucopyranosyl residue of the BSH-dextran may, in principle, be oxidatively cleaved using any oxidizing agent capable of oxidatively cleaving the D-glucopyranosyl unit between two vicinal carbons substituted by free hydroxyl groups. The oxidizing agent may also be selected so that it essentially specifically oxidatively cleaves the at least one D-glucopyranosyl residue of the BSH-dextran. Such an oxidizing agent may not oxidize other groups or moieties of the BSH-dextran.

In an embodiment, the at least one D-glucopyranosyl residue of the BSH-dextran is oxidatively cleaved in step c) using an oxidizing agent selected from the group consisting of sodium periodate, periodic acid and lead(IV) acetate.

In an embodiment, the at least one D-glucopyranosyl residue of the BSH-dextran is oxidatively cleaved in step c) in an aqueous solution.

In an embodiment, the method further comprises the step of reacting the oxidatively cleaved BSH-dextran obtainable from step c) or the conjugate obtainable from step d) with a tracking molecule.

In this context, the tracking molecule may be any tracking molecule described in this document.

The tracking molecule may react with at least one aldehyde group of the oxidatively cleaved BSH-dextran obtainable from step c). A suitable group of the tracking molecule that may react with the at least one aldehyde group may be e.g. an amino group.

In an embodiment, the method further comprises the step e) of capping unreacted aldehyde groups of the oxidatively cleaved BSH-dextran obtainable from step c) or the conjugate obtainable from step d).

In an embodiment, the unreacted aldehyde groups are capped using a hydrophilic capping agent, such as ethanolamine, lysine, glycine or Tris.

In an embodiment, the hydrophilic capping agent is selected from the group consisting of ethanolamine, lysine, glycine and Tris.

In an embodiment, ethanolamine comprising $^{14}C$ is a tracking molecule.

In an embodiment, one or more steps selected from steps a), b), c) and d) are performed in an aqueous solution. A suitable aqueous solution may be e.g. an aqueous phosphate buffer having a pH of about 6 to 8.

In an embodiment, all of the steps a)-d) are performed in an aqueous solution.

The anti-EGFR1 antibody or an EGFR1 binding fragment thereof typically contains at least one amino group, such as the N-terminal amine group and/or the amino group of a lysine residue. In step d), the aldehyde groups of the oxidatively cleaved BSH-dextran obtainable from step c) may thus react with the at least one amino group of the anti-EGFR1 antibody or an EGFR1 binding fragment thereof.

In an embodiment, the amino group of the anti-EGFR1 antibody or an EGFR1 binding fragment thereof is the amino group of a lysine residue of the anti-EGFR1 antibody or an EGFR1 binding fragment thereof.

In an embodiment, the oxidatively cleaved BSH-dextran is reacted with the anti-EGFR1 antibody or an EGFR1 binding fragment thereof by incubating the oxidatively cleaved BSH-dextran and the anti-EGFR1 antibody or an EGFR1 binding fragment thereof in room temperature in an aqueous phosphate buffer having a pH of about 6 to 8 in step d).

The conjugate may be purified e.g. by gel filtration, for instance as described in Example 4.

The present invention further relates to the production of anti-EGFR1 antibodies or EGFR1 binding fragments thereof in prokaryotic host cells. Compared to other polypeptide production systems, bacteria, particularly E. coli, provides many unique advantages. The raw materials used (i.e. bacterial cells) are inexpensive and easy to grow, therefore reducing the cost of products. Prokaryotic hosts grow much faster than, e.g., mammalian cells, allowing quicker analysis of genetic manipulations. Shorter generation time and ease of scaling up also make bacterial fermentation a more attractive means for large quantity protein production. The genomic structure and biological activity of many bacterial species including E. coli have been well-studied and a wide range of suitable vectors are available, making expression of a desirable antibody more convenient. Antibody or antibody fragment expression in prokaryotic systems can be carried out in different scales. The shake-flask cultures (in the 2-5 liter-range) typically generate less than 5 mg/liter of the products (e.g. antibody fragment) whereas 50-300 mg/liter scale may be obtained in fermentation systems.

Furthermore, prokaryotic host cells may allow the production of aglycosylated anti-EGFR antibodies or EGFR1 binding fragments thereof.

In an embodiment, the prokaryotic host cell comprises one or more polynucleotides encoding
i) a light chain variable region and
ii) a heavy chain variable region
of an anti-EGFR1 antibody or an EGFR1 binding fragment thereof. The term "one or more polynucleotides" may refer to two or more polynucleotides or polynucleotide molecules that may or may not be covalently linked, directly or indirectly via one or more sequences. For instance, the two or more polynucleotides may be comprised in an expression cassette or a vector. The two or more polynucleotides may, as an example, be fused, directly or indirectly, so as to encode a fusion protein comprising both the light chain variable region and the heavy chain variable region. They may also be comprised in two separate expression cassettes or vectors. The term "one or more polynucleotides" may also refer to a single, continuous polynucleotide molecule comprising the one or more polynucleotides or polynucleotide stretches encoding the light chain variable region and the heavy chain variable region of an anti-EGFR1 antibody or an EGFR1 binding fragment thereof.

In an embodiment, the host cell comprises a polynucleotide according to one or more embodiments described in this specification encoding an anti-EGFR1 antibody or an EGFR1 binding fragment thereof. The host cell may comprise one or more polynucleotides collectively encoding the anti-EGFR1 antibody or an EGFR1 binding fragment. A vector can be of any type, for example, a recombinant vector such as an expression vector.

Any of a variety of prokaryotic host cells can be used.

In an embodiment, the prokaryotic host cell is an E. coli cell.

In an embodiment, the one or more polynucleotides encoding the light chain variable region and the heavy chain variable region are codon optimized for the host cell, such as an E. coli cell.

In an embodiment, the prokaryotic host cell comprises a single continuous polynucleotide encoding both the light chain variable region and the heavy chain variable region of an anti-EGFR1 antibody or an EGFR1 binding fragment thereof. Such a continuous polynucleotide may be dicistronic or polycistronic.

In an embodiment, the prokaryotic host cell comprises a polynucleotide encoding a light chain variable region of an anti-EGFR1 antibody or an EGFR1 binding fragment thereof and another polynucleotide encoding a heavy chain variable region of an anti-EGFR1 antibody or an EGFR1 binding fragment thereof.

In an embodiment, the light chain variable region is preceded by a signal peptide. The polynucleotide thus encodes both the signal peptide preceding the light chain variable region and the light chain variable region. The signal peptide may immediately precede the light chain variable region, or there may be a sequence stretch between the signal peptide and the light chain variable region. The signal peptide may be selected from the group consisting of gIII, malE, phoA, ompA, pelB, stII, and stII. The signal peptide may also be selected from the group consisting of ompA, pelB, stII, and stII. These signal peptides may allow particularly high yields in the production of the antibody or fragment in a prokaryotic host cell, such as E. coli.

In an embodiment, the heavy chain variable region is preceded by a signal peptide. The signal peptide may be selected from the group consisting of gIII, malE, phoA, ompA, pelB, stII, and stII. The signal peptide may also be selected from the group consisting of ompA, pelB, stII, and stII.

In an embodiment, the light chain variable region and the heavy chain variable region are preceded by a signal peptide.

In an embodiment, the signal peptide preceding the light chain variable region is other than the signal peptide preceding the heavy chain variable region.

In an embodiment, the signal peptide preceding the light chain variable region and the heavy chain variable region are independently selected from the group consisting of gIII, malE, phoA, ompA, pelB, stII, and stII.

In an embodiment, the signal peptide preceding the light chain variable region and the heavy chain variable region are independently selected from the group consisting of ompA, pelB, stII, and stII.

In an embodiment, the signal peptide preceding the light chain variable region is the same as the signal peptide preceding the heavy chain variable region, and wherein the signal peptide is selected from the group consisting of gIII, malE, phoA, ompA, pelB, stII, and stII.

In an embodiment, the signal peptide preceding the light chain variable region is the same as the signal peptide preceding the heavy chain variable region, and wherein the signal peptide is selected from the group consisting of ompA, pelB, stII, and stII.

In an embodiment, the light chain variable region is preceded by the pelB signal peptide and the heavy chain variable region is preceded by the ompA signal peptide.

In an embodiment, both the light chain variable region and the heavy chain variable region are preceded by the stII signal peptide.

In an embodiment, the polynucleotide comprises or consists of the sequence set forth in SEQ ID NO: 8 and the sequence set forth in SEQ ID NO: 9.

In an embodiment, the polynucleotide comprises or consists of the sequence set forth in SEQ ID NO: 8 or a sequence that is at least 90%, at least 91%, at least 92%, at least 93%, at least 94%, at least 95%, at least 96%, at least 97%, at least 98%, or at least 99% identical to SEQ ID NO: 8, and the sequence set forth in SEQ ID NO: 9 or a sequence that is at least 90%, at least 91%, at least 92%, at least 93%, at least 94%, at least 95%, at least 96%, at least 97%, at least 98%, or at least 99% identical to SEQ ID NO: 9.

In an embodiment, the polynucleotide encoding a light chain variable region comprises or consists of the sequence set forth in SEQ ID NO: 8 and the polynucleotide encoding a heavy chain variable region comprises or consists of the sequence set forth in SEQ ID NO: 9.

In an embodiment, the polynucleotide encoding a light chain variable region comprises or consists of the sequence set forth in SEQ ID NO: 8, or a sequence that is at least 90%, at least 91%, at least 92%, at least 93%, at least 94%, at least 95%, at least 96%, at least 97%, at least 98%, or at least 99% identical to SEQ ID NO: 8, and the polynucleotide encoding a heavy chain variable region comprises or consists of the sequence set forth in SEQ ID NO: 9, or a sequence that is at least 90%, at least 91%, at least 92%, at least 93%, at least 94%, at least 95%, at least 96%, at least 97%, at least 98%, or at least 99% identical to SEQ ID NO: 9.

In an embodiment, the prokaryotic host cell comprises one or more polynucleotides encoding
i) a light chain and
ii) a heavy chain
of an anti-EGFR1 binding fragment of an antibody.

In an embodiment, the one or more polynucleotides encode an anti-EGFR1 binding fragment that is a Fab or a scFv.

In an embodiment, the polynucleotide encoding the light chain comprises or consists of the sequence set forth in SEQ ID NO: 10, and the polynucleotide encoding the heavy chain sequence comprises or consists of the sequence set forth in SEQ ID NO: 11.

In an embodiment, the polynucleotide encoding the light chain comprises or consists of the sequence set forth in SEQ ID NO: 10, or a sequence that is at least 90%, at least 91%, at least 92%, at least 93%, at least 94%, at least 95%, at least 96%, at least 97%, at least 98%, or at least 99% identical to SEQ ID NO: 10, and the polynucleotide encoding the heavy chain sequence comprises or consists of the sequence set forth in SEQ ID NO: 11 or a sequence that is at least 90%, at least 91%, at least 92%, at least 93%, at least 94%, at least 95%, at least 96%, at least 97%, at least 98%, or at least 99% identical to SEQ ID NO: 11.

In an embodiment, the one or more polynucleotides comprise or consist of the light chain sequence set forth in SEQ ID NO: 10 and the heavy chain sequence set forth in SEQ ID NO: 11.

In an embodiment, the one or more polynucleotides comprise or consist of the light chain sequence set forth in SEQ ID NO: 10 or a sequence that is at least 90%, at least 91%, at least 92%, at least 93%, at least 94%, at least 95%, at least 96%, at least 97%, at least 98%, or at least 99% identical to SEQ ID NO: 10, and the heavy chain sequence set forth in SEQ ID NO: 11 or a sequence that is at least 90%, at least 91%, at least 92%, at least 93%, at least 94%, at least 95%, at least 96%, at least 97%, at least 98%, or at least 99% identical to SEQ ID NO: 11.

In an embodiment, the host cell comprises a polynucleotide comprising or consisting of the sequence set forth in SEQ ID NO: 12 or a sequence that is at least 90%, at least 91%, at least 92%, at least 93%, at least 94%, at least 95%, at least 96%, at least 97%, at least 98%, or at least 99% identical to SEQ ID NO: 12.

In an embodiment, the host cell comprises a polynucleotide comprising or consisting of the sequence set forth in SEQ ID NO: 13 or a sequence that is at least 90%, at least 91%, at least 92%, at least 93%, at least 94%, at least 95%, at least 96%, at least 97%, at least 98%, or at least 99% identical to SEQ ID NO: 13.

In an embodiment, the host cell comprises a chaperone protein and/or one or more polynucleotides encoding a chaperone protein. The chaperone protein may be a prokaryotic chaperone protein, such as Dsb proteins (DsbA, DsbB, DsbC, DsbD, FkpA and/or DsbG. In an embodiment, the chaperone protein is overexpressed in the host cell.

In an embodiment, the chaperone protein is DsbA and/or DsbC.

In an embodiment, the chaperone protein is selected from the group consisting of DnaK, DnaJ, GrpE, Skp, FkpA, GroEL, and GroES.

In an embodiment, the chaperone protein is Skp.

The term "prokaryotic host cell" as used herein, is intended to refer to a prokaryotic cell that has been genetically altered, or is capable of being genetically altered by introduction of an exogenous polynucleotide, such as a recombinant plasmid or vector. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "prokaryotic host cell" as used herein.

Prokaryotic host cells are transfected and preferably transformed with the above-described polynucleotides encoding anti-EGFR1 antibody or EGFR1 binding fragments thereof, for example, in expression or cloning vectors and cultured in conventional nutrient media modified as appropriate for inducing promoters, selecting transformants, or amplifying the genes encoding the desired antibody or antibody fragment sequences. Promoters suitable for use with prokaryotic hosts include the PhoA promoter, the β-lactamase and lactose promoter systems, a tryptophan (trp) promoter system and hybrid promoters such as the tac or the trc promoter. However, other promoters that are functional in bacteria (such as other known bacterial) are suitable as well. Their nucleotide sequences have been published, thereby enabling a skilled worker operably to ligate them to cistrons encoding the target light and heavy chains (Siebenlist et al., (1980) Cell 20: 269) using linkers or adaptors to supply any required restriction sites.

In an embodiment, the one or more polynucleotides are driven by, i.e. operably linked to, a promoter independently selected from the group consisting of T7, T5, and Rham.

In an embodiment, the one or more polynucleotides are driven by the promoter T7. Prokaryotic host cells used to produce the anti-EGFR1 antibodies or EGFR1 binding fragments thereof can be cultured as described generally in "Molecular Cloning" laboratory manual (Michael Green and Joseph Sambrook; fourth edition; Cold Spring Harbour Laboratory Press; 2012). Prokaryotic host cells suitable for expressing antibodies of the invention include Archaebacteria and Eubacteria, such as Gram-negative or Gram-positive organisms. Examples of useful bacteria include *Escherichia* (e.g., *E. coli*), Bacilli (e.g., *B. subtilis*), Enterobacteria, *Pseudomonas* species (e.g., *P. aeruginosa*), *Salmonella typhimurium*, *Serratia marcescans*, *Klebsiella*, *Proteus*, *Shigella*, *Rhizobia*, *Vitreoscilla*, or *Paracoccus*. In one embodiment, gram-negative cells are used. In one embodiment, *E. coli* cells are used as hosts for the invention. Examples of *E. coli* strains include strain W3110 (Bachmann, Cellular and Molecular Biology, vol. 2 (Washington, D.C.: American Society for Microbiology, 1987), pp. 1190-1219; ATCC Deposit No. 27, 325) and derivatives thereof, including strain 33D3 having genotype W3110ΔfhuA (ΔtonA) ptr3 lac Iq lacL8 Δomp TΔ (nmpc-fepE) degP41 kanR (U.S. Pat. No. 5,639,635) and strains 63C1 and 64B4. Other strains and derivatives thereof, such as *E. coli* 294 (ATCC 31,446), *E. coli* B, *E. coli*, 1776 (ATCC 31,537) and *E. coli* RV308 (ATCC 31,608) are also suitable. These examples are illustrative rather than limiting. It may generally be necessary to select the appropriate bacteria taking into consideration replicability of the replicon in the cells of a bacterium. For example, *E. coli* species can be suitably used as the host when well-known plasmids such as pBR322, pBR325, pACYC 177, or pKN410 are used to supply the replicon. Typically the host cell may secrete minimal amounts of proteolytic enzymes, and additional protease inhibitors may desirably be incorporated in the cell culture.

In an embodiment, the host cell is deficient for one or more proteolytic enzymes.

In an embodiment, the proteolytic enzyme is selected from the group consisting of Protease III, OmpT, DegP, Tsp, Protease I, Protease Mi, Protease V, Protease VI, and Lon.

After transformation, prokaryotic cells used to produce the anti-EGFR1 antibodies or EGFR1 binding fragments thereof are grown in media known in the art and suitable for culture of the selected host cells. Examples of suitable media include Luria broth (LB), Terrific broth (TB) and Minimal synthetic media plus nutrient supplements such as yeast extract, soybean hydrolysate and other vegetable hydrolysates. In some embodiments, the media also contains a selection agent, chosen based on the construction of the expression vector, to selectively permit growth of prokaryotic cells containing the expression vector. For example, ampicillin is added to media for growth of cells expressing ampicillin resistant gene. Any necessary supplements besides carbon, nitrogen, and inorganic phosphate sources may also be included at appropriate concentrations introduced alone or as a mixture with another supplement or medium such as a complex nitrogen source. Optionally the culture medium may contain one or more reducing agents selected from the group consisting of glutathione, cysteine, cystamine, thioglycollate, dithioerythritol and dithiothreitol.

The prokaryotic host cells are cultured at suitable temperatures. For *E. coli* growth, for example, the preferred temperature ranges from about 20° C. to about 39° C. The pH of the medium may be any pH ranging from about 5 to about 9, depending mainly on the host organism. For *E. coli*, the pH is preferably from about 6.8 to about 7.4, and more preferably about 7.0. If an inducible promoter is used in the expression vector, anti-EGFR1 antibody or EGFR1 binding fragment protein expression is induced under conditions suitable for the activation of the promoter.

In an embodiment, the anti-EGFR1 antibody or EGFR1 binding fragment thereof are secreted into and recovered from the periplasm of the prokaryotic host cells. Protein recovery typically involves disrupting the microorganism, generally by such means as osmotic shock, sonication or lysis. Once cells are disrupted, cell debris or whole cells may be removed by centrifugation or filtration. The proteins may be further purified, for example, by affinity resin chromatography or Protein L columns suitable for purification of Fab fragments. Alternatively, proteins can be transported into the culture media and isolated therein. Cells may be removed from the culture and the culture supernatant being filtered and concentrated for further purification of the proteins produced. The expressed polypeptides can be further isolated and identified using commonly known methods such as polyacrylamide gel electrophoresis (PAGE) and Western blot assay.

In one aspect of the invention, anti-EGFR1 antibody or EGFR1 binding fragment production is conducted in large quantity by a fermentation process. Various large-scale fed-batch fermentation procedures are available for production of recombinant proteins. Large-scale fermentations have at least 500 liters of capacity. These fermentors use agitator impellers to distribute oxygen and nutrients, especially glucose (the preferred carbon/energy source). Small scale fermentation refers generally to fermentation in a fermentor that is no more than approximately 100 liters in volumetric capacity, and can range from about 1 liter to about 100 liters.

In a fermentation process, induction of protein expression is typically initiated after the cells have been grown under suitable conditions to a desired density, e.g., an $OD_{550}$ of about 180-220, at which stage the cells are in the early stationary phase. A variety of inducers may be used, according to the vector construct employed, as is known in the art and described above. Cells may be grown for shorter periods prior to induction. Cells are usually induced for about 12-50 hours, although longer or shorter induction time may be used.

To improve the production yield and quality of the anti-EGFR1 antibody or EGFR1 binding fragments, various fermentation conditions can be modified. For example, to improve the proper assembly and folding of the secreted antibody polypeptides, additional vectors overexpressing chaperone proteins, such as Dsb proteins (DsbA, DsbB, DsbC, DsbD, and/or DsbG), Skp or FkpA (a peptidylprolyl cis,trans-isomerase with chaperone activity) can be used to co-transform the host prokaryotic cells. The chaperone proteins have been demonstrated to facilitate the proper folding and solubility of heterologous proteins produced in bacterial host cells. Chen et al., (1999) J. Biol. Chem. 274:19601-19605; Georgiou et al., U.S. Pat. No. 6,083,715; Georgiou et al., U.S. Pat. No. 6,027,888; Bothmann and Pluckthun (2000) J. Biol. Chem. 275:17100-17105; Ramm and Pluckthun, (2000) J. Biol. Chem. 275:17106-17113; Arie et al., (2001) Mol. Microbiol. 39:199-210.

In an embodiment, chaperones such as DnaK/DnaJ/GrpE, Skp, Skp/FkpA, GroEL/GroES are expressed in the bacterial host cell such as *E. coli*.

To minimize proteolysis of expressed anti-EGFR1 antibody or EGFR1 binding fragments thereof (especially those that are proteolytically sensitive), certain host strains deficient for proteolytic enzymes can be used. For example, host cell strains may be modified to effect genetic mutation(s) in the genes encoding known bacterial proteases such as Protease III, OmpT, DegP, Tsp, Protease I, Protease Mi, Protease V, Protease VI, and combinations thereof. Some *E. coli* protease-deficient strains are available and described in, for example, Joly et al., (1998), supra; Georgiou et al., U.S. Pat. No. 5,264,365; Georgiou et al., U.S. Pat. No. 5,508,192; Hara et al., Microbial Drug Resistance, 2:63-72 (1996).

In an embodiment, *E. coli* strains deficient for proteolytic enzymes and transformed with plasmids overexpressing one or more chaperone proteins are used as host cells in the expression system of the invention.

Purification of anti-EGFR1 antibodies or EGFR1 binding fragments thereof may be accomplished using art-recognized methods. The following procedures are exemplary of suitable purification procedures: fractionation on immuno-affinity or ion-exchange columns, ethanol precipitation, reverse phase HPLC, chromatography on silica or on a cation-exchange resin such as DEAE, chromatofocusing, SDS-PAGE, ammonium sulfate precipitation, and gel filtration using, for example, Sephadex G-75.

In an embodiment, Protein A immobilized on a solid phase is used for immunoaffinity purification of the anti-EGFR1 antibodies.

In an embodiment, Protein L immobilized on a solid phase is used for immunoaffinity purification of the anti-EGFR1 antibody fragments of the invention.

As the first step of purification, the preparation derived from the cell culture as described above is applied onto the Protein A or Protein L immobilized solid phase to allow specific binding of the anti-EGFR1 antibody to Protein A, or anti-EGFR1 antibody fragment, such as Fab fragment, to Protein L. The solid phase is then washed to remove contaminants non-specifically bound to the solid phase. Finally the antibody or antibody fragment is recovered from the solid phase by elution.

In an embodiment, the light chain variable region is preceded by the pelB signal peptide and the heavy chain variable region is preceded by the ompA signal peptide; the host cell comprises the chaperone protein Skp and/or a polynucleotide encoding the chaperone protein Skp; and the host cell is deficient for the proteolytic enzymes Lon and OmpT.

In an embodiment, the light chain variable region and the heavy chain variable region are preceded by the stII signal peptide; the host cell comprises the chaperone protein Skp and/or a polynucleotide encoding the chaperone protein Skp; and the host cell is deficient for the proteolytic enzymes Lon and OmpT.

A polynucleotide encoding
i) a light chain variable region and
ii) a heavy chain variable region
of an anti-EGFR1 antibody or an EGFR1 binding fragment thereof is also disclosed.

The term "a polynucleotide" may in this context refer to one, two or more polynucleotides or polynucleotide molecules that may or may not be covalently linked, directly or indirectly via one or more sequences. For instance, the two or more polynucleotides may be comprised in an expression cassette or a vector. The two or more polynucleotides may, as an example, be fused, directly or indirectly, so as to encode a fusion protein comprising both the light chain variable region and the heavy chain variable region. They may also be comprised in two separate expression cassettes or vectors. The term "a polynucleotide" may also refer to a single, continuous polynucleotide molecule comprising the one or more polynucleotides or polynucleotide stretches encoding the light chain variable region and the heavy chain variable region of an anti-EGFR1 antibody or an EGFR1 binding fragment thereof.

The polynucleotide may be dicistronic or polycistronic.

In an embodiment, the polynucleotide encoding the light chain variable region and the heavy chain variable region is codon optimized for a host cell. The host cell may be a prokaryotic cell, such as an *E. coli* cell.

In an embodiment, the polynucleotide encoding a light chain variable region comprises or consists of the sequence set forth in SEQ ID NO: 8 or a sequence that is at least 90%, at least 91%, at least 92%, at least 93%, at least 94%, at least 95%, at least 96%, at least 97%, at least 98%, or at least 99% identical to SEQ ID NO: 8. In an embodiment, the polynucleotide encoding a heavy chain variable region comprises or consists of the sequence set forth in SEQ ID NO: 9 or a sequence that is at least 90%, at least 91%, at least 92%, at least 93%, at least 94%, at least 95%, at least 96%, at least 97%, at least 98%, or at least 99% identical to SEQ ID NO: 9.

In an embodiment, the polynucleotide encoding a light chain variable region comprises or consists of the sequence set forth in SEQ ID NO: 8 and the polynucleotide encoding a heavy chain variable region comprises or consists of the sequence set forth in SEQ ID NO: 9.

In an embodiment, the polynucleotide encoding a light chain variable region comprises or consists of the sequence set forth in SEQ ID NO: 8, or a sequence that is at least 90%, at least 91%, at least 92%, at least 93%, at least 94%, at least 95%, at least 96%, at least 97%, at least 98%, or at least 99% identical to SEQ ID NO: 8, and the polynucleotide encoding a heavy chain variable region comprises or consists of the sequence set forth in SEQ ID NO: 9, or a sequence that is at least 90%, at least 91%, at least 92%, at least 93%, at least 94%, at least 95%, at least 96%, at least 97%, at least 98%, or at least 99% identical to SEQ ID NO: 9.

In an embodiment, the polynucleotide encodes
i) a light chain and
ii) a heavy chain
of an anti-EGFR1 binding fragment of an antibody.

In an embodiment, the polynucleotide encodes an anti-EGFR1 binding fragment that is a Fab or a scFv.

In an embodiment, the polynucleotide comprises or consists of the light chain sequence set forth in SEQ ID NO: 10, or a sequence that is at least 90%, at least 91%, at least 92%, at least 93%, at least 94%, at least 95%, at least 96%, at least 97%, at least 98%, or at least 99% identical to SEQ ID NO: 10.

In an embodiment, the polynucleotide comprises or consists of the heavy chain sequence set forth in SEQ ID NO: 11, or a sequence that is at least 90%, at least 91%, at least 92%, at least 93%, at least 94%, at least 95%, at least 96%, at least 97%, at least 98%, or at least 99% identical to SEQ ID NO: 11.

In an embodiment, the polynucleotide comprises or consists of the light chain sequence set forth in SEQ ID NO: 10 and the heavy chain sequence set forth in SEQ ID NO: 11.

In an embodiment, the polynucleotide comprises or consists of the light chain sequence set forth in SEQ ID NO: 10, or a sequence that is at least 90%, at least 91%, at least 92%, at least 93%, at least 94%, at least 95%, at least 96%, at least 97%, at least 98%, or at least 99% identical to SEQ ID NO: 10, and the heavy chain sequence set forth in SEQ ID NO: 11, or a sequence that is at least 90%, at least 91%, at least 92%, at least 93%, at least 94%, at least 95%, at least 96%, at least 97%, at least 98%, or at least 99% identical to SEQ ID NO: 11.

In an embodiment, the polynucleotide comprises or consists of the sequence set forth in SEQ ID NO: 12, or a sequence that is at least 90%, at least 91%, at least 92%, at least 93%, at least 94%, at least 95%, at least 96%, at least 97%, at least 98%, or at least 99% identical to SEQ ID NO: 12.

In an embodiment, the polynucleotide comprises or consists of the sequence set forth in SEQ ID NO: 13, or a sequence that is at least 90%, at least 91%, at least 92%, at least 93%, at least 94%, at least 95%, at least 96%, at least 97%, at least 98%, or at least 99% identical to SEQ ID NO: 13.

In an embodiment, the light chain variable region and the heavy chain variable region are preceded by a signal peptide. The polynucleotide thus encodes both a signal peptide and the light chain variable region, and a signal peptide and the heavy chain variable region. The two signal peptides may be selected independently from each other, or they may be the same signal peptide.

In an embodiment, the signal peptide preceding the light chain variable region is other than the signal peptide preceding the heavy chain variable region.

In an embodiment, the signal peptide preceding the light chain variable region and the heavy chain variable region are independently selected from the group consisting of gIII, malE, phoA, ompA, pelB, stII, and stII.

In an embodiment, the signal peptide preceding the light chain variable region and the heavy chain variable region are independently selected from the group consisting of ompA, pelB, stII, and stII.

In an embodiment, the signal peptide preceding the light chain variable region is the same as the signal peptide preceding the heavy chain variable region, and wherein the signal peptide is selected from the group consisting of gIII, malE, phoA, ompA, pelB, stII, and stII.

In an embodiment, the signal peptide preceding the light chain variable region is the same as the signal peptide preceding the heavy chain variable region, and wherein the signal peptide is selected from the group consisting of ompA, pelB, stII, and stII.

In an embodiment, the light chain variable region is preceded by the pelB signal peptide and the heavy chain variable region is preceded by the ompA signal peptide.

In an embodiment, both the light chain variable region and the heavy chain variable region are preceded by the stII signal peptide.

The polynucleotide may also be operatively linked to, i.e. be driven by, or comprise a promoter. The promoter may allow efficient expression of the polynucleotide. The promoter may also be an inducible promoter, thereby allowing inducible expression of the polynucleotide.

In an embodiment, the polynucleotide is driven by, i.e. operably linked to, or comprises, a promoter selected from the group consisting of T7, T5, and Rham.

In an embodiment, the polynucleotide is driven by or comprises the promoter T7. In an embodiment, a prokaryotic host cell produces at least 20, mg/L, at least 30 mg/L, at least 50 mg/L, at least 100 mg/L, at least 200 mg/L, or at least 500 mg/L of an anti-EGFR1 antibody or an EGFR1 binding fragment of an anti-EGFR1 antibody. In an embodiment, an E. coli cell produces at least 20, mg/L, at least 30 mg/L, at least 50 mg/L, at least 100 mg/L, at least 200 mg/L, or at least 500 mg/L of an anti-EGFR1 antibody or an EGFR1 binding fragment of an anti-EGFR1 antibody.

In an embodiment, an E. coli cell produces at least at least 20, mg/L, at least 30 mg/L, at least 50 mg/L, at least 100 mg/L, at least 200 mg/L, or at least 500 mg/L of an anti-EGFR1 Fab.

In an embodiment, an E. coli cell produces at least 20, mg/L, at least 30 mg/L, at least 50 mg/L, at least 100 mg/L, at least 200 mg/L, or at least 500 mg/L of an anti-EGFR1 scFv.

In an embodiment, an E. coli cell comprises or consists of the polynucleotide set forth in SEQ ID NO: 8 or a sequence that is at least 90%, at least 91%, at least 92%, at least 93%, at least 94%, at least 95%, at least 96%, at least 97%, at least 98%, or at least 99% identical to SEQ ID NO: 8, and the sequence set forth in SEQ ID NO: 9 or a sequence that is at least 90%, at least 91%, at least 92%, at least 93%, at least 94%, at least 95%, at least 96%, at least 97%, at least 98%, or at least 99% identical to SEQ ID NO: 9, and the E. coli cell produces at least 20, mg/L, at least 30 mg/L, at least 50 mg/L, at least 100 mg/L, at least 200 mg/L, or at least 500 mg/L of an anti-EGFR1 antibody or an EGFR1 binding fragment of an anti-EGFR1 antibody.

In an embodiment, an E. coli cell comprises or consists of the polynucleotide set forth in SEQ ID NO: 8 or a sequence that is at least 90%, at least 91%, at least 92%, at least 93%, at least 94%, at least 95%, at least 96%, at least 97%, at least 98%, or at least 99% identical to SEQ ID NO: 8, and the sequence set forth in SEQ ID NO: 9 or a sequence that is at least 90%, at least 91%, at least 92%, at least 93%, at least 94%, at least 95%, at least 96%, at least 97%, at least 98%, or at least 99% identical to SEQ ID NO: 9, and the E. coli cell produces at least 20, mg/L, at least 30 mg/L, at least 50 mg/L, at least 100 mg/L, at least 200 mg/L, or at least 500 mg/L of an anti-EGFR1 Fab or an anti-EGFR1 scFv.

In an embodiment, an E. coli cell comprises or consists of the polynucleotide set forth in SEQ ID NO: 8 and the sequence set forth in SEQ ID NO: 9 and the E. coli cell produces at least 20, mg/L, at least 30 mg/L, at least 50 mg/L, at least 100 mg/L, at least 200 mg/L, or at least 500 mg/L of an anti-EGFR1 Fab or an anti-EGFR1 scFv.

In an embodiment, an E. coli cell comprises or consists of the polynucleotide set forth in SEQ ID NO: 10, or a sequence that is at least 90%, at least 91%, at least 92%, at least 93%, at least 94%, at least 95%, at least 96%, at least 97%, at least 98%, or at least 99% identical to SEQ ID NO: 10, and the heavy chain sequence set forth in SEQ ID NO: 11, or a sequence that is at least 90%, at least 91%, at least 92%, at least 93%, at least 94%, at least 95%, at least 96%, at least 97%, at least 98%, or at least 99% identical to SEQ ID NO: 11, and the E. coli cell produces at least 20, mg/L, at least 30 mg/L, at least 50 mg/L, at least 100 mg/L, at least 200 mg/L, or at least 500 mg/L of an anti-EGFR1 antibody or an EGFR1 binding fragment of an anti-EGFR1 antibody.

In an embodiment, an E. coli cell comprises or consists of the polynucleotide set forth in SEQ ID NO: 10, or a sequence that is at least 90%, at least 91%, at least 92%, at least 93%, at least 94%, at least 95%, at least 96%, at least 97%, at least 98%, or at least 99% identical to SEQ ID NO: 10, and the heavy chain sequence set forth in SEQ ID NO: 11, or a sequence that is at least 90%, at least 91%, at least 92%, at least 93%, at least 94%, at least 95%, at least 96%, at least 97%, at least 98%, or at least 99% identical to SEQ ID NO: 11, and the E. coli cell produces at least 20, mg/L, at least 30 mg/L, at least 50 mg/L, at least 100 mg/L, at least 200 mg/L, or at least 500 mg/L of an anti-EGFR1 Fab.

In an embodiment, an E. coli cell comprises or consists of the polynucleotide set forth in SEQ ID NO: 12, or a sequence that is at least 90%, at least 91%, at least 92%, at least 93%, at least 94%, at least 95%, at least 96%, at least 97%, at least 98%, or at least 99% identical to SEQ ID NO: 12, and the E. coli cell produces at least 20, mg/L, at least 30 mg/L, at least 50 mg/L, at least 100 mg/L, at least 200 mg/L, or at least 500 mg/L of an anti-EGFR1 scFv.

In an embodiment, an E. coli cell comprises or consists of the polynucleotide set forth in SEQ ID NO: 13, or a sequence that is at least 90%, at least 91%, at least 92%, at least 93%, at least 94%, at least 95%, at least 96%, at least 97%, at least 98%, or at least 99% identical to SEQ ID NO: 13, and the E. coli cell produces at least 20, mg/L, at least 30 mg/L, at least 50 mg/L, at least 100 mg/L, at least 200 mg/L, or at least 500 mg/L of an anti-EGFR1 scFv.

The present invention further relates to a pharmaceutical composition comprising the conjugate according to one or more embodiments of the present invention.

The pharmaceutical composition of the present invention may further comprise a pharmaceutically acceptable carrier. Examples of suitable pharmaceutically acceptable carriers are well known in the art and may include e.g. phosphate buffered saline solutions, water, oil/water emulsions, wetting agents, and liposomes. Compositions comprising such carriers may be formulated by methods well known in the art. The pharmaceutical composition may further comprise other components such as vehicles, additives, preservatives, other pharmaceutical compositions administrated concurrently, and the like.

In an embodiment, the pharmaceutical composition comprises an effective amount of the conjugate according to one or more embodiments of the invention.

In an embodiment, the pharmaceutical composition comprises a therapeutically effective amount of the conjugate according to one or more embodiments of the invention.

The term "therapeutically effective amount" or "effective amount" of the conjugate should be understood as referring to the dosage regimen for modulating the growth of cancer cells and/or treating a patient's disease when cancer cells are bombarded with neutron radiation or exposed to BNCT. The therapeutically effective amount may be selected in accordance with a variety of factors, including the age, weight, sex, diet and medical condition of the patient, the severity of the disease, and pharmacological considerations, such as the activity, efficacy, pharmacokinetic and toxicology profiles of the particular conjugate used. The therapeutically effective amount can also be determined by reference to standard medical texts, such as the Physicians Desk Reference 2004. The patient may be male or female, and may be an infant, child or adult.

The term "treatment" or "treat" is used in the conventional sense and means attending to, caring for and nursing a patient with the aim of combating, reducing, attenuating or alleviating an illness or health abnormality and improving the living conditions impaired by this illness, such as, for example, with a cancer disease.

In an embodiment, the pharmaceutical composition comprises a composition for e.g. oral, parenteral, transdermal, intraluminal, intraarterial, intrathecal, intra-tumoral (i.t.), and/or intranasal administration or for direct injection into tissue. Administration of the pharmaceutical composition may be effected in different ways, e.g. by intravenous, intraperitoneal, subcutaneous, intramuscular, intra-tumoral, topical or intradermal administration.

The present invention further relates to the conjugate according to one or more embodiments of the present invention or the pharmaceutical composition comprising the conjugate according to one or more embodiments of the present invention for use as a medicament.

The present invention further relates to the conjugate according to one or more embodiments of the present invention or the pharmaceutical composition comprising the conjugate according to one or more embodiments of the present invention for use as a medicament for boron neutron capture therapy.

"Boron neutron capture therapy" (BNCT) should be understood as referring to targeted radiotherapy, wherein nonradioactive boron-10 is irradiated with low energy thermal neutrons to yield alpha particles and lithium-7 nuclei. The nonradioactive boron-10 may be targeted by incorporating it in a tumor localizing drug such as a tumor localizing conjugate.

The present invention further relates to the conjugate according to one or more embodiments of the present invention or the pharmaceutical composition comprising the conjugate according to one or more embodiments of the present invention for use in boron neutron capture therapy.

The present invention further relates to the conjugate according to one or more embodiments of the present invention or the pharmaceutical composition comprising the conjugate according to one or more embodiments of the present invention for use in the treatment of cancer.

In an embodiment, the cancer is a head-and-neck cancer.

In an embodiment, the cancer is selected from the group consisting of head-and-neck cancer, leukemia, lymphoma, breast cancer, prostate cancer, ovarian cancer, colorectal cancer, gastric cancer, squamous cancer, small-cell lung cancer, multidrug resistant cancer and testicular cancer.

The present invention further relates to the conjugate according to one or more embodiments of the present invention or the pharmaceutical composition comprising the conjugate according to one or more embodiments of the present invention for use in the treatment of cancer by boron neutron capture therapy.

The present invention further relates to the use of the conjugate or the pharmaceutical composition according to one or more embodiments of the present invention in the manufacture of a medicament.

The present invention further relates to the use of the conjugate or the pharmaceutical composition according to one or more embodiments of the present invention in the manufacture of a medicament for boron neutron capture therapy.

The present invention further relates to the use of the conjugate or the pharmaceutical composition according to one or more embodiments of the present invention in the manufacture of a medicament for the treatment of cancer.

In an embodiment, the cancer is a head-and-neck cancer.

In an embodiment, the cancer is selected from the group consisting of head-and-neck cancer, leukemia, lymphoma, breast cancer, prostate cancer, ovarian cancer, colorectal cancer, gastric cancer, squamous cancer, small-cell lung cancer, multidrug resistant cancer and testicular cancer.

The present invention further relates to the use of the conjugate or the pharmaceutical composition according to one or more embodiments of the present invention in the manufacture of a medicament for the treatment of cancer by boron neutron capture therapy.

In an embodiment, the medicament is for the intra-tumor treatment of head-and-neck cancer by boron neutron capture therapy.

In an embodiment, the medicament is for the intravenous treatment of head-and-neck cancer by boron neutron capture therapy.

In an embodiment, the medicament is for the intra-tumor and intravenous treatment of head-and-neck cancer by boron neutron capture therapy.

The present invention also relates to a method of treating or modulating the growth of EGFR1 expressing tumor cells in a human, wherein the conjugate or the pharmaceutical composition according to one or more embodiments of the invention is administered to a human in an effective amount.

In an embodiment, the conjugate or the pharmaceutical composition according to one or more embodiments of the invention is administered to a human in an effective amount in boron neutron capture therapy.

In an embodiment, the concentration of boron is analysed in tumor cells after administering the conjugate or the pharmaceutical composition.

In an embodiment, the concentration of boron is analysed in blood after administering the conjugate or the pharmaceutical composition.

In an embodiment, the concentration of boron is analysed in muscle, or in other non-tumor tissue, after administering the conjugate or the pharmaceutical composition.

The concentration of boron in tumor cells, in blood or in both may be analysed or measured e.g. by inductively coupled plasma mass spectrometry (ICP-MS) or inductively coupled plasma atomic emission spectroscopy (ICP-AES) (e.g. Example 9). These methods measure the amount (in moles) or concentration of boron atoms in the sample.

The concentration of boron in tumor cells, in blood or in both may also be analysed or measured indirectly, e.g. by using an embodiment of the conjugate comprising a tracking molecule and analysing or measuring the concentration of the tracking molecule. For instance, if the tracking molecule is fluorescent or radioactive, the fluorescence or radioactivity of the tracking molecule may be measured or visualised.

In an embodiment, the concentration of boron is analysed in tumor cells and in blood after administering the conjugate or the pharmaceutical composition, and the ratio of the concentration of boron in tumor cells to the concentration of boron in blood is higher than 1:1, 2:1, 3:1, 4:1, 5:1, 6:1, 7:1, 8:1, 9:1, 10:1, 11:1, 12:1, 13:1, 15:1, 20:1, 30:1, 40:1, 50:1, 60:1, 70:1, 80:1, 90:1, 100:1, 110:1, 120:1, 130:1, 140:1, 150:1, 200:1, 210:1, 220:1, 230:1, 240:1, or 250:1.

In an embodiment, the concentration of boron is analysed in tumor cells and in a muscle, or in other non-tumor tissue, after administering the conjugate or the pharmaceutical composition, and the ratio of the concentration of boron in tumor cells to the concentration of boron in a muscle, or other non-tumor tissue, is higher than 1:1, 2:1, 3:1, 4:1, 5:1, 6:1, 7:1, 8:1, 9:1, 10:1, 11:1, 12:1, 13:1, 15:1, 20:1, 30:1, 40:1, 50:1, 60:1, 70:1, 80:1, 90:1, 100:1, 110:1, 120:1, 130:1, 140:1, 150:1, 200:1, 210:1, 220:1, 230:1, 240:1, or 250:1.

In an embodiment, the ratio of the concentration of boron in tumor cells to the concentration of boron in blood, in a muscle, or in other non-tumor tissue is the molar ratio of boron atoms in tumor cells to the boron atoms in blood, in a muscle, or in other non-tumor tissue.

The present invention also relates to a method for modulating the growth of a cell population expressing EGFR1 protein, wherein the method comprises the step of
contacting the conjugate according to one or more embodiments of the invention or the pharmaceutical composition according to one or more embodiments of the invention with the cell population expressing EGFR1 protein.

In an embodiment, the cell population expressing EGFR1 protein is a cancer cell population or a tumor cell population.

In this context, the term "a cancer cell population" should be understood as referring to one or more cancer cell populations.

The conjugate may be contacted in vitro, in vivo and/or ex vivo to with the cell population, for example, cancer cells, including, for example, cancer of the blood, plasma, lung, breast, colon, prostate, kidney, pancreas, brain, bones, ovary, testes, and lymphatic organs; more preferably lung, colon prostrate, plasma, blood or colon cancer; "Modulating the growth of cancer cell populations" includes inhibiting the proliferation of cell populations from dividing to produce more cells; reducing the rate of increase in cell division as compared, for example, to untreated cells; killing cell populations; and/or preventing cell populations (such as cancer cells) from metastasizing. The growth of cell populations may be modulated in vitro, in vivo or ex vivo.

In an embodiment, the cancer is selected from the group consisting of head-and-neck cancer, leukemia, lymphoma, breast cancer, prostate cancer, ovarian cancer, colorectal cancer, gastric cancer, squamous cancer, small-cell lung cancer, multidrug resistant cancer and testicular cancer.

The present invention further relates to a method of treating and/or modulating the growth of and/or prophylaxis of tumor cells in humans, wherein the conjugate or the pharmaceutical composition according to one or more embodiments of the invention is administered to a human in an effective amount.

In an embodiment, the effective amount is a therapeutically effective amount.

In an embodiment, the conjugate or the pharmaceutical composition according to one or more embodiments of the invention is administered to a human in an effective amount in boron neutron capture therapy.

In an embodiment, the tumor cells are selected from the group consisting of leukemia cells, lymphoma cells, breast cancer cells, prostate cancer cells, ovarian cancer cells, colorectal cancer cells, gastric cancer cells, squamous cancer cells, small-cell lung cancer cells, head-and-neck cancer cells, multidrug resistant cancer cells, and testicular cancer cells, metastatic, advanced, drug- or hormone-resistant, multidrug resistant cancer cells, and versions thereof.

The present invention further relates to a method of treating cancer in humans, wherein the conjugate or the pharmaceutical composition according to one or more embodiments of the invention is administered to a human in an effective amount.

In an embodiment, the conjugate or the pharmaceutical composition according to one or more embodiments of the invention is administered to a human in an effective amount in boron neutron capture therapy.

In an embodiment, the effective amount is a therapeutically effective amount.

In an embodiment, the conjugate or the pharmaceutical composition according to one or more embodiments of the invention is administered intravenously to a human in a therapeutically effective amount in boron neutron capture therapy.

In an embodiment, the conjugate or the pharmaceutical composition according to one or more embodiments of the invention is administered intra-tumorally to a human in a therapeutically effective amount in boron neutron capture therapy.

In an embodiment, the conjugate or the pharmaceutical composition according to one or more embodiments of the invention is administered intra-tumorally and intravenously to a human in a therapeutically effective amount in boron neutron capture therapy.

In an embodiment, the conjugate or the pharmaceutical composition according to one or more embodiments of the invention is administered intra-tumorally into head-and-neck tumor in a therapeutically effective amount in boron neutron capture therapy.

In an embodiment, the cancer is selected from the group consisting of head-and-neck cancer, leukemia, lymphoma, breast cancer, prostate cancer, ovarian cancer, colorectal cancer, gastric cancer, squamous cancer, small-cell lung cancer, multidrug resistant cancer and testicular cancer.

In an embodiment, the conjugate or the pharmaceutical composition according to one or more embodiments comprises an anti-EGFR1 antibody or EGFR1 binding fragment thereof that is obtainable by a method comprising
culturing the prokaryotic host cell according to one or more embodiments; and
isolating and/or purifying the anti-EGFR1 antibody or an EGFR1 binding fragment thereof.

In an embodiment, the anti-EGFR1 antibody or an EGFR1 binding fragment thereof of the conjugate or the pharmaceutical composition according to one or more embodiments comprises or consists of the amino acid sequence set forth in SEQ ID NO: 14 or SEQ ID NO: 15.

The invention also relates to a method for treating or modulating the growth of EGFR1 expressing tumor cells in a human, wherein the conjugate according to one or more embodiments or the pharmaceutical composition according to one or more embodiments is administered to a human in an effective amount. The embodiments of the invention described hereinbefore may be used in any combination with each other. Several of the embodiments may be combined together to form a further embodiment of the invention. A product, a use or a method to which the invention is related may comprise at least one of the embodiments of the invention described hereinbefore.

The conjugate according to one or more embodiments of the invention has a number of advantageous properties.

The conjugate according to one or more embodiments of the invention is relatively non-toxic in the absence of low energy neutron irradiation and has low antigenicity.

It contains a high number of boron-10 atoms per conjugate molecule. Further, it exhibits relatively good aqueous solubility.

The conjugate according to one or more embodiments of the invention also exhibits good pharmacokinetics. It has suitable retention in blood, high uptake in cells to which it is targeted and low uptake in cells and organs to which it is not targeted.

Its production process is relatively simple and can be performed in aqueous solutions.

The conjugate according to one or more embodiments of the invention is sufficiently stable towards chemical or biochemical degradation during manufacturing or in physiological conditions, e.g. in blood, serum, plasma or tissues.

EXAMPLES

In the following, the present invention will be described in more detail. Reference will now be made in detail to the embodiments of the present invention, examples of which are illustrated in the accompanying drawings. The description below discloses some embodiments of the invention in such detail that a person skilled in the art is able to utilize the invention based on the disclosure. Not all steps of the embodiments are discussed in detail, as many of the steps will be obvious for the person skilled in the art based on this specification.

Example 1. Allylation of Dextran 200 mg Dextran 70 kD (Sigma) was dissolved in 2 ml of 0.6 M NaOH. 250 µl of allyl bromide (Sigma) was added, and the reaction was allowed to proceed for 3 h at 60° C. The reaction mixture was then neutralized with 1M acetic acid and the product was isolated by precipitation with 10 volumes of cold acetone (−20° C.). Precipitate was collected by centrifugation and washed twice with acetone. The allylated dextran (Scheme 1) was subjected to $^1$H-NMR analysis, which showed that the level of allylation was ca. 36%.

Scheme 1. Dextran allylation by use of allyl bromide.

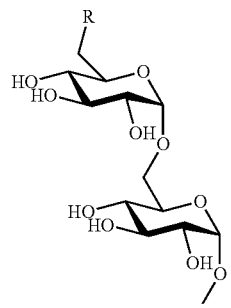

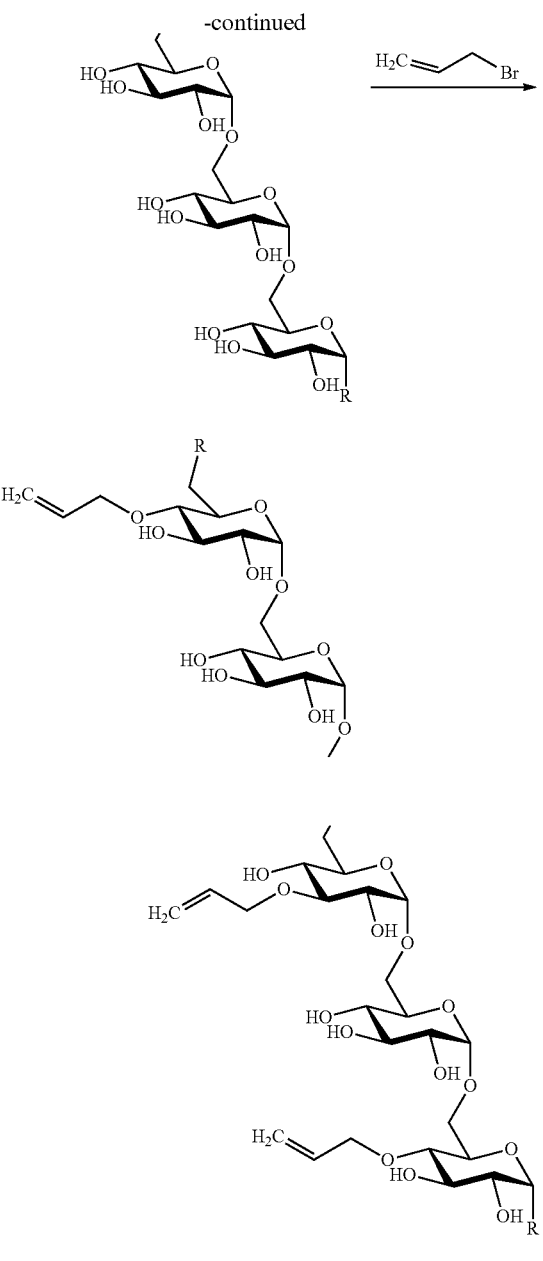

Example 2. Addition of BSH to Allyl Dextran 50 mg allyl dextran 70 kD prepared as described in Example 1, 50 mg ammonium persulfate and 50 mg sodium borocaptate (BSH; Katchem Ltd, Czech Republic) were dissolved in 0.5 ml H$_2$O.

The reaction was allowed to proceed for 2 h at 50° C. The reaction product, BSH-dextran (Scheme 2), was isolated with ultrafiltration using centrifugal filter (Amicon, 10K cut-off). $^1$H-NMR analysis showed that on average 100 BSH units were linked to allyl dextran, corresponding to 1200 boron atoms per dextran chain (FIG. 1). With minor modifications, e.g. by use of lower allylation level in dextran, BSH dextran with ca. 900 borons or 800 borons per dextran chain were obtained.

Scheme 2. Addition of sodium borocaptate to allyl dextran in a persulfate catalyzed reaction.

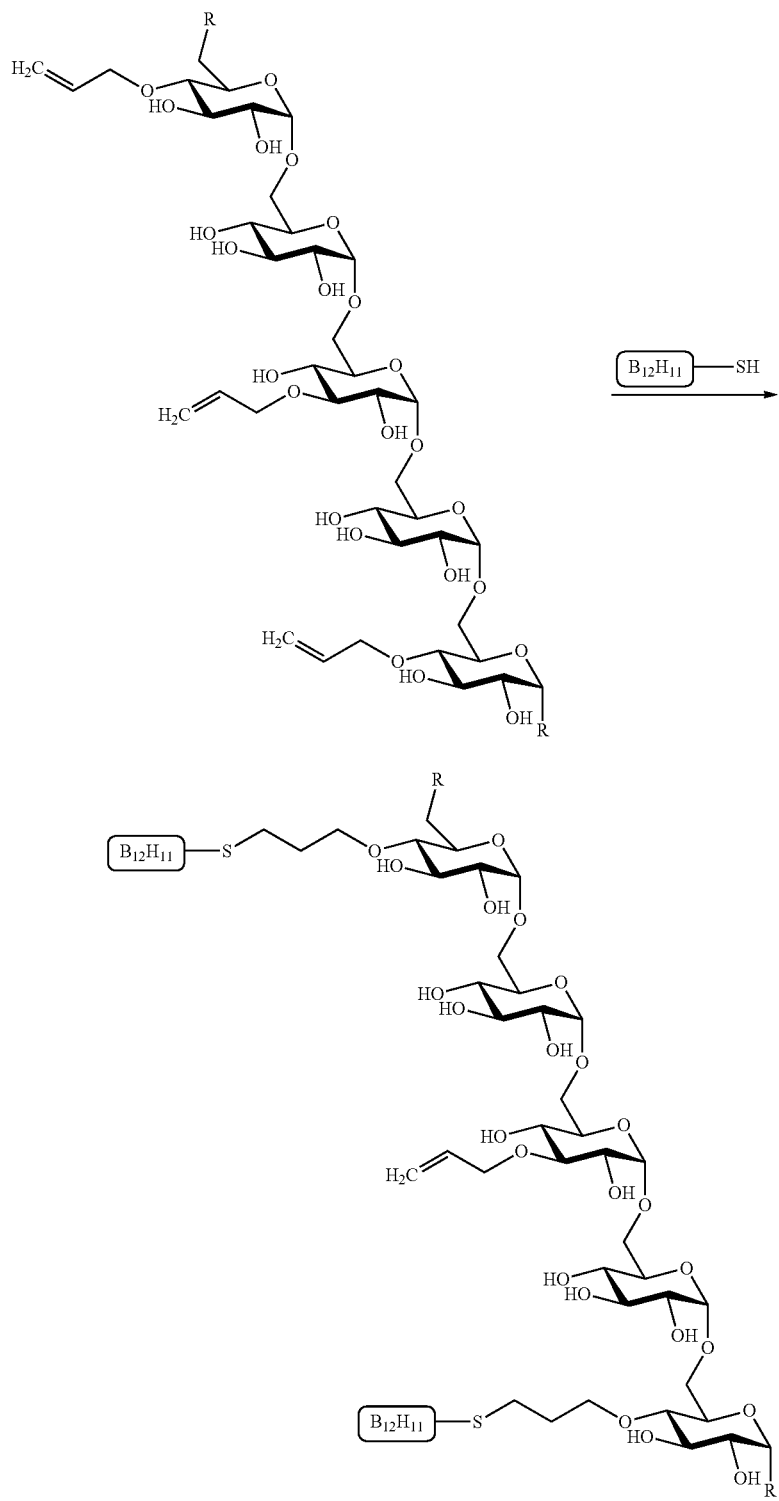

By varying the amount of BSH and persulfate in the reaction described above, it was possible to prepare BSH-dextrans with a clearly lower BSH level: 1) In a reaction containing 20 mg allyl dextran, 15 mg ammonium persulfate and 15 mg BSH, the isolated BSH-dextran was found to contain ca. 700 boron atoms per dextran chain. 2) In a reaction containing 20 mg allyl dextran, 10 mg ammonium persulfate and 10 mg BSH, the isolated BSH-dextran was found to contain ca. 560 boron atoms per dextran chain. 3) In a reaction containing 20 mg allyl dextran, 5 mg ammonium persulfate and 5 mg BSH, the isolated BSH-dextran was found to contain ca. 360 boron atoms per dextran chain.

Example 3. Oxidation of BSH-Dextran 50 mg of BSH-dextran prepared as described in Example 2 was dissolved in 3 ml of 25 mM NaIO$_4$ in 0.1 M sodium acetate, pH 5.5. The reaction tube was covered with aluminium foil and incubated at RT overnight. The reaction product, oxidized BSH-dextran (Scheme 3), was isolated with ultrafiltration using a centrifugal filter (Amicon, 10K cut-off).

Scheme 3. Oxidation of BSH-dextran by use of sodium periodate.

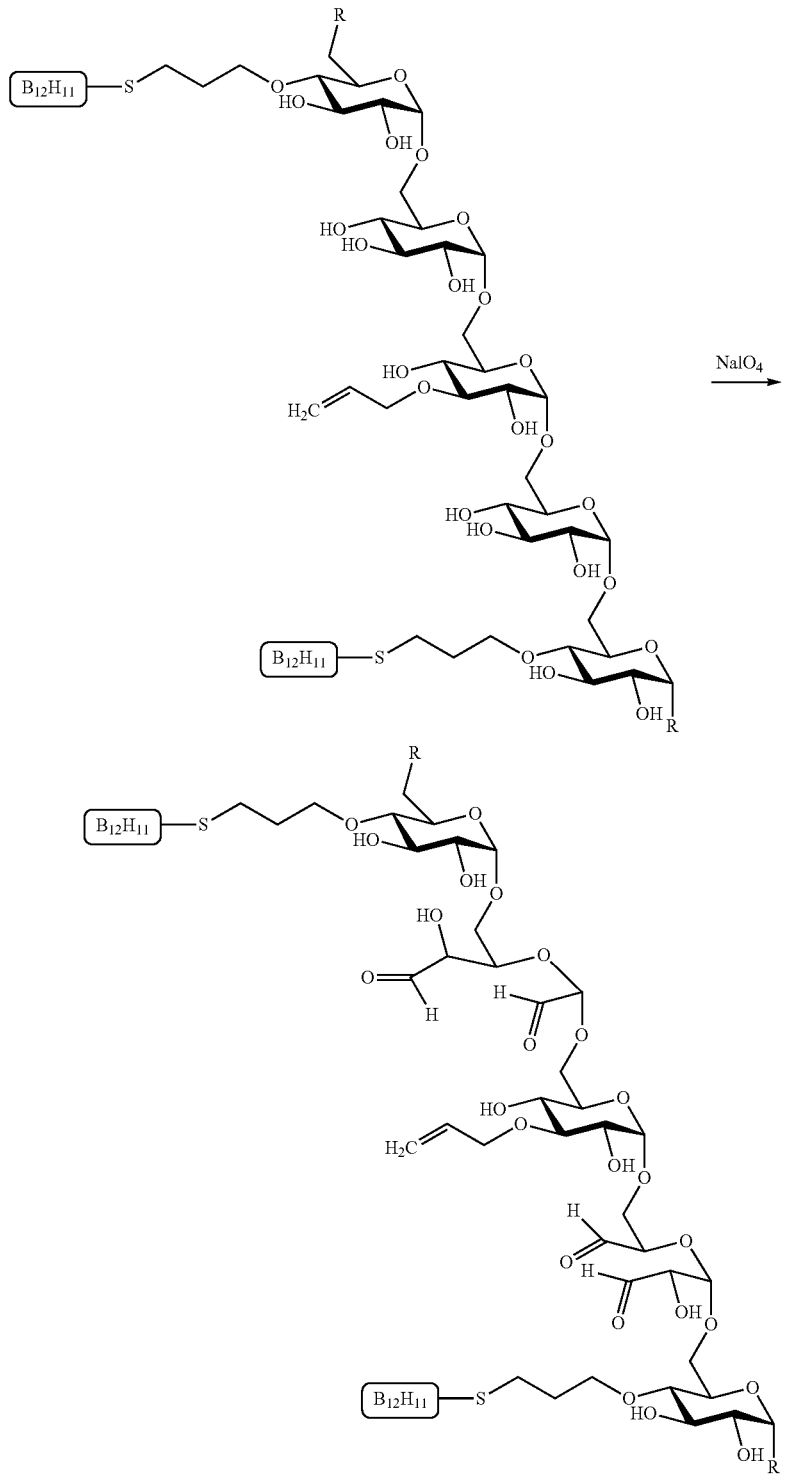

Example 4. Conjugation of Oxidized BSH-Dextran to Anti-EGFR1 Fab/F(ab')2

2 mg (40 nmol) of anti-EGFR1 Fab in 2 ml of phosphate buffered saline (PBS) was mixed with 5.1 mg (60 nmol) of oxidized BSH-dextran (Example 3) in 1.6 ml of PBS. Reaction was allowed to proceed overnight at RT. 400 µl of 0.5 M NaCNBH$_3$ was added to the reaction to stabilize the aldehyde-lysine linkages and the reaction was incubated for 2 hours at RT. 800 µl of 0.2 M ethanolamine-HCl pH 8 was added and the reaction was incubated for 1 hour at RT. 400 µl of 0.5 M NaCNBH$_3$ was added to stabilize ethanolamine capping and the reaction was incubated for 2 hours at RT. Low molecular weight reagents were removed by a Amicon centrifugal filter unit (MWCO 30K) according to the manufacturer's instructions using PBS as the washing eluent.

2 mg (40 nmol) of anti-EGFR1 F(ab')2 in 2 ml of phosphate buffered saline (PBS) was mixed with 2.56 mg (30 nmol) of oxidized BSH-dextran (Example 3) in 1.6 ml of PBS. Conjugate was stabilized, capped and purified by ultrafiltration as above.

Both conjugates were analyzed by Äkta purifier (GE Healthcare) with a Yarra 3 µm SEC-3000 gel filtration column (300×7.8 mm; Phenomenex) using 10% acetonitrile (ACN)-50 mM Tris-HCl, pH 7.5 as the elution buffer (FIG. 2).

Example 5. Generation of Anti-EGFR1-Fab and -F(Ab')2, and Control-Fab and -F(Ab')2 Fragments Fab and F(ab')2 fragments were generated either from commercial cetuximab (Erbitux, Roche) or cetuximab produced in CHO cells (Freedom CHO-S kit, Invitrogen). Freedom CHO-S Kit (Life Technologies) was used for the development of stable cell lines producing cetuximab. The work was done according to manufacturer's instructions. Optimized nucleotide sequences encoding the heavy and light chain sequences were purchased from GeneArt (Life Technologies) and cloned separately into pCEP4 expression vectors (Life Technologies). For stable expression, the FreeStyle™ CHO-S cells were transfected with linearized 1:1 light chain and heavy chain vectors. Transfectants were selected with puromycin and methotrexate after which clone isolation was done by limited dilution cloning. Cloned cell lines were scaled up and assessed for productivity.

Control-Fab and -F(ab')2 fragments were generated from commercial omalizumab (anti-IgE) (Xolair, Novartis).

Anti-EGFR1 Fab fragments were prepared by digesting antibody with immobilized papain (Pierce) according to manufacturer's instructions with minor modifications. The used ratio of enzyme to substrate was 1:60 (w/w) and incubation time was 7 h. Fab fragments were separated from undigested IgG and Fc fragments with a column of immobilized protein A (Thermo Scientific) according to the manufacturer's instructions.

Anti-EGFR1 F(ab')2 fragments were prepared by digesting the antibody with either FragIT MaxiSpin (Genovis) according to manufacturer's instructions or with Fabricator enzyme (Genovis) according to the manufacturer's instructions with minor modifications. Fabricator enzyme digestion was performed with 120 Units of enzyme per mg of antibody in 50 mM sodium phosphate buffer pH 6.6 and incubation time was 1 h at +37° C. F(ab')2 fragments were purified with an immobilized HiTrap protein L column (GE Healthcare) according to the manufacturer's instructions. Reaction buffer was changed to PBS with Amicon Ultra concentrator (Millipore) (10 kDa cutoff).

The generated fragments were identified with SDS-PAGE and the protein concentration of each fragment was determined by measuring UV absorbance at 280 nm.

Example 6. SDS-PAGE Analysis of Boron Conjugates

Figure 3:
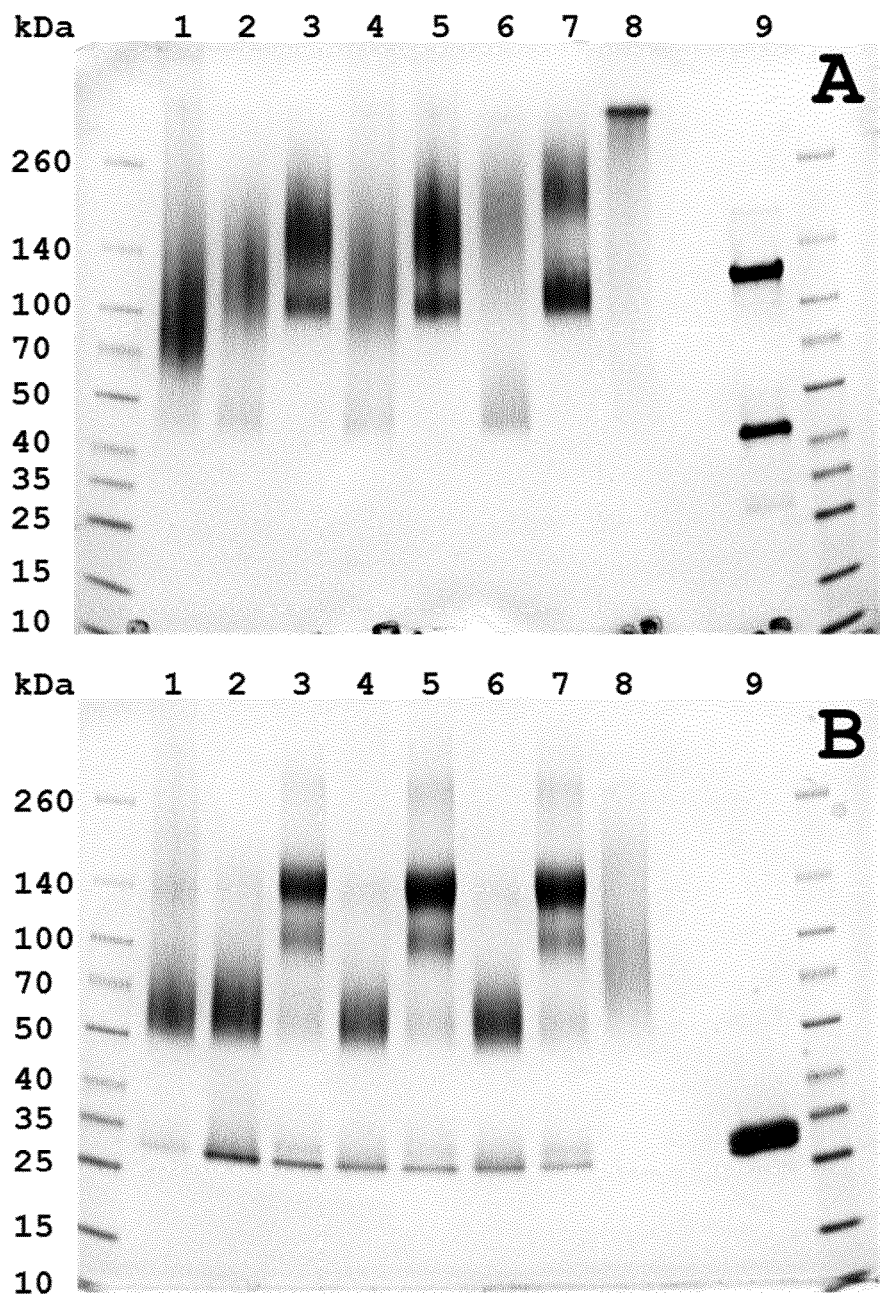
FIG. 3. SDS-PAGE analysis of fluorescently labeled anti-EGFR1 Fab/F(ab')2 boron conjugates with different amounts of boron in nonreducing (panel A) and reducing (panel B) conditions. Anti-EGFR1-Fab-BSH-Dex conjugates: Lane 1 (900B), lane 2 (700B), lane 4 (560B), lane 6 (360B). Anti-EGFR1-F(ab')2-BSH-Dex conjugates: Lane 3 (700B), lane 5 (560B), lane 7 (360B). Lane 8 is Anti-EGFR1-Fab-Dex and lane 9 is a control containing a mixture of anti-EGFR1-F(ab')2 and Fc fragments (Fab fragments migrate like Fc fragments on the gel). Gel staining with Coomassie Blue.

Boron conjugates of anti-EGFR1 Fab and F(ab')2 fragments were analyzed using SDS-PAGE in order to verify that the conjugations have been successful and that unconjugated Fab or F(ab')2 fragments are not present after conjugation. Figure shows an SDS-PAGE analysis of anti-EGFR1 Fab/F(ab')2 boron conjugates with different amounts of boron in a gradient gel (Bio-Rad, 4-15%) under nonreducing (panel A) and reducing (panel B) conditions. The results of panel A show that conjugation has been complete (or near complete) because unconjugated Fab or F(ab')2 fragments were not visible. BSH is a negatively charged molecule and when conjugated to a protein the migration velocity of a conjugate is faster on a gel than expected based on its theoretical molecular weight. The example of FIG. 3 (Panel A) indicates that conjugates with high amount of boron migrate faster on a nonreducing gel than conjugates with lower amount of boron (e.g. compare lanes 1, 2, 4 and 6). The results of FIG. 3 (Panel A) also indicate that most of the conjugates are separated into two bands on a nonreducing gel implying that the samples contain a mixture of two different kinds of conjugates. SDS-PAGE analysis of boron conjugates in reducing conditions (FIG. 3, panel B) show that all Fab conjugates with different amounts of boron migrate similarly on the gel under reducing conditions (Lanes 1, 2, 4, 6). Likewise, reduced F(ab')2 conjugates with different amounts of boron migrate identically (Lanes 3, 5, 7). In general, reduced boron conjugates migrate faster on the gel than nonreduced conjugates.

Example 7. In Vitro Internalization Assays of Boron Conjugates

AlexaFluor488 Labeling of Boron Conjugates

5 µg AlexaFluor488 carboxylic acid, succinimidyl ester label (Invitrogen) was incubated with 100 µg of boron conjugates (anti-EGFR1-Fab, anti-EGFR1-F(ab')2, anti-EGFR1-mAb, control-Fab, control-F(ab')2, control-mAb) or corresponding nonconjugated compounds for 15 min at room temperature in a buffer containing 10 µl 1 M NaHCO$_3$, pH 9 in 100 µl PBS. After incubation excess label was removed by changing the buffer to PBS with Amicon Ultra concentrator (Millipore) (10 kDa cutoff). Protein concentration of each compound was determined by measuring UV absorbance at 280 nm and the degree of labeling was calculated according to the manufacturer's instructions (Invitrogen).

Tritium Labeling of Boron Conjugates

After removal of toluene solvent by evaporation, 100 µCi tritium labeled N-succinimidyl propionate (Perkin Elmer) was incubated with 100 µg of anti-EGFR1-Fab-BSH(800B)-Dex, anti-EGFR1-F(ab')2-BSH(800B)-Dex, anti-EGFR1-mAb and control-mAb in a buffer containing 20 µl 1 M Na-borate buffer, pH 8.8 in 100 µl PBS. Reaction was allowed to proceed overnight at room temperature and then excess label was removed by changing the buffer to PBS with an Amicon Ultra concentrator (10 kDa cutoff). The amount of radioactivity was measured with a scintillation counter in the presence of a scintillation fluid cocktail (Ultima Gold, Perkin Elmer). The amount of tritium label in compounds was calculated as cpm/μg protein.

Cell Culture

HSC-2 cells (human squamous cell carcinoma of mouth, JCRP Cellbank, Japan) and FaDu cells (human squamous cell carcinoma of pharynx, ATCC) were cultured in T75 flasks in Eagle's minimal essential medium with 2% glutamine, 10% fetal bovine serum and 1% penicillin/streptomycin. HEK (Human Embryonic Kidney, ATCC) cells were cultured in T75 flasks in Dulbecco's Modified Eagle Medium with 2% glutamine, 10% fetal bovine serum and 1% penicillin/streptomycin.

Internalization Assay Visualized in Fluorescence Microscopy

HSC-2 cells ($5\times10^4$) were seeded on a chamber slide and allowed to grow for 24 h. Then the cells were incubated for 3 h at +37° C. or at +4° C. in 100 μl media containing 10 μg/ml AlexaFluor488 labeled BSH-conjugates. After incubation cells were washed two times with PBS and fixed with 4% paraformaldehyde for 20 min. Mounting media (Prolong Gold antifade reagent with DAPI) was added and the cells were covered with microscopy cover slips. Cells were photographed with fluorescence microscopy (Zeiss Axio Scope A1; ProgRes C5, JENOPTIK AG).

Figure 4:
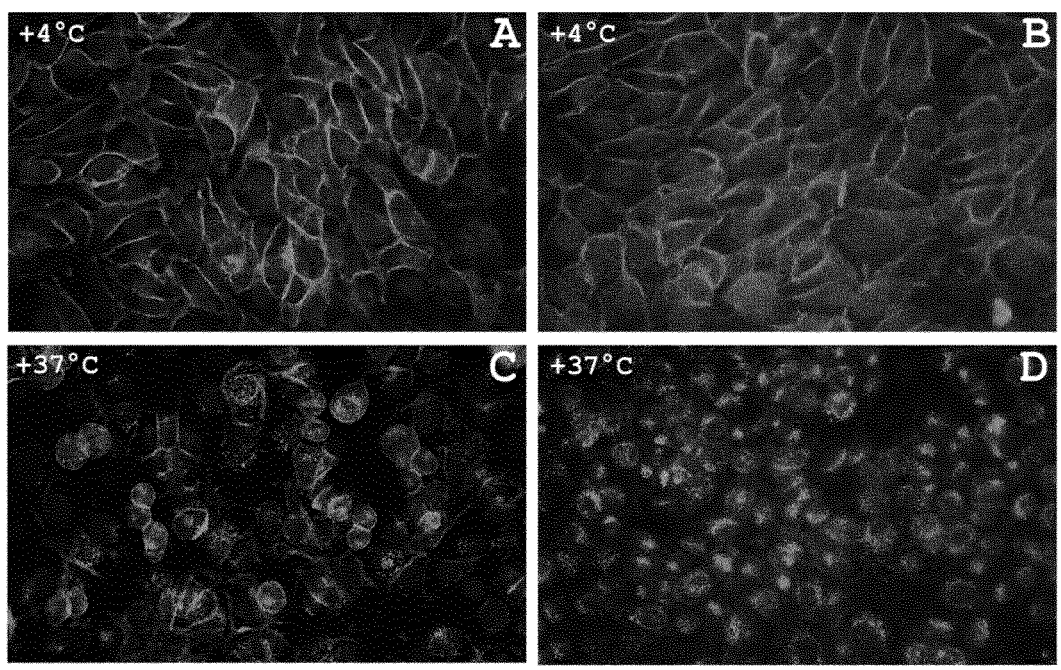
FIG. 4. Cell surface binding and internalization of fluorescently labeled anti-EGFR1-F(ab')2 (Panels A and C) and anti-EGFR1-F(ab')2-BSH(900B)-Dex (Panels B and D) by HSC-2 cells. Incubations have been performed at +4° C. (binding to the cell surface) and at +37° C. (binding to cell surface and internalization). Analysis has been carried out by fluorescence microscopy.

Internalization of anti-EGFR1-F(ab')2-BSH(900B)-Dex and nonconjugated anti-EGFR1-F(ab')2 by HSC-2 tumor cell line was analyzed by fluorescence microscopy (FIG. 4). The experiment was carried out at +4° C. (compounds bind to the cell surface but cannot be internalized) and at +37° C. (cells are able to internalize the surface-bound compounds). Both nonconjugated anti-EGFR1-F(ab')2 and boron conjugate bound to the cell surface at +4° C. (Panels A and B) and were internalized at +37° C. (Panels C and D). In fact, boron conjugate was internalized more efficiently than nonconjugated anti-EGFR1-F(ab')2. Internalization assay with anti-EGFR1-Fab-BSH(900B)-Dex and EGFR1-mAb-BSH (900B)-Dex and corresponding nonconjugated anti-EGFR1-Fab and anti-EGFR1-mAb gave very similar results to the data presented in FIG. 4 (not shown). The effect of boron load for internalization was examined using boron conjugates (anti-EGFR1-Fab-BSH-Dex and anti-EGFR1-F(ab')2-BSH-Dex) with different amounts of boron. The results indicated that conjugates with more boron were internalized more efficiently by HSC-2 cells than conjugates with low boron load at +37° C. (not shown). Control-F(ab')2-BSH (900B)-Dex was internalized only very weakly (not shown).

Internalization Assay (FACS)

HSC-2, FaDu and HEK cells ($2\times10^5$) were seeded on a 24 well plate and allowed to grow for 24 h. Then the cells were incubated for 3 h at +37° C. in 300 μl media containing 5 μg/ml AlexaFluor488 labeled compounds. After incubation the cells were washed two times with PBS and detached by incubating with 100 μl Trypsin-EDTA for 10 min at +37° C. Cells were neutralized by adding 300 μl of media and resuspended in PBS and analyzed using a flow cytometer (FACS LRS II). The mean fluorescence intensity of each sample was calculated using FACS Diva software. The data presented in Tables 1-3 is expressed as "Normalized mean fluorescence intensity" where the fluorescence intensity has been normalized to the degree of labeling for each compound.

Assays with FACS

Internalization of fluorescently labeled boron conjugates (900 boron atoms) and nonconjugated Ab fragments by human HNC cancer cell line HSC-2 was evaluated using FACS. The results represent internalized plus cell surface bound compounds that occurs when cells have been incubated at +37° C. (Table 1). Anti-EGFR1-Fab-BSH-Dex was internalized more efficiently than other boron conjugates or nonconjugated anti-EGFR1-Fab. Other anti-EGFR1 boron conjugates (anti-EGFR1-F(ab')2-BSH-Dex and anti-EGFR1-mAb-BSH-Dex) were internalized equally well to nonconjugated anti-EGFR1-Fab and anti-EGFR1-F(ab')2. Boron conjugates of control-F(ab')2 and -mAb were internalized very weakly.

TABLE 1

Cell surface binding and internalization of fluorescently labeled boron conjugates and nonconjugated compounds by HSC-2 cells. Analysis has been carried out by FACS and fluorescence intensity has been normalized to the degree of labeling for each compound.

| Sample | HSC-2 Normalized mean fluorescence intensity |
|---|---|
| Anti-EGFR1-Fab-BSH(900B)-Dex | 158700 |
| Anti-EGFR1-F(ab')2-BSH(900B)-Dex | 81100 |
| Control-F(ab')2-BSH(900B)-Dex | 2200 |
| Anti-EGFR1-mAb-BSH(900B)-Dex | 92700 |
| Control-mAb-BSH(900B)-Dex | 8200 |
| Anti-EGFR1-Fab | 99500 |
| Anti-EGFR1-F(ab')2 | 93100 |
| Anti-EGFR1-mAb | 21300 |
| Control-mAb | 700 |

Boron conjugates with different amounts of boron (360-900 boron atoms) were synthesized from anti-EGFR1 F(ab')2 and -Fab to study the effect of boron load in the internalization process. Example shows internalization assay with fluorescently labeled conjugates using human HNC cancer cell line HSC-2 and a control human cell line HEK. The results from flow cytometric analysis represent internalized plus cell surface bound compounds that occurs when cells have been incubated at +37° C. (Table 2). Internalization of all boron conjugates of anti-EGFR1 Ab fragments was very similar as analyzed by flow cytometry. However, experiments with microscopy revealed that conjugates with more boron were internalized more efficiently than conjugates with low boron load (not shown).

TABLE 2

Cell surface binding and internalization of fluorescently labeled boron conjugates with different amounts of boron by HSC-2 and HEK cells. Analysis has been carried out by flow cytometry and fluorescence intensity has been normalized to the degree of labeling for each compound.

| Sample | HSC-2 Normalized mean fluorescence intensity | HEK |
|---|---|---|
| Anti-EGFR1-Fab-BSH(900B)-Dex | 33900 | |
| Anti-EGFR1-Fab-BSH(700B)-Dex | 48300 | 590 |
| Anti-EGFR1-Fab-BSH(560B)-Dex | 48000 | 860 |
| Anti-EGFR1-Fab-BSH(360B)-Dex | 37000 | 470 |
| Anti-EGFR1-F(ab')2 -BSH(700B)-Dex | 41900 | 600 |
| Anti-EGFR1-F(ab')2 -BSH(560B)-Dex | 48400 | 530 |
| Anti-EGFR1-F(ab')2 -BSH(360B)-Dex | 43100 | 470 |
| Anti-EGFR1-mAb | 10700 | 110 |

Internalization of fluorescently labeled boron conjugates (1200 or 800 boron atoms) and nonconjugated Ab fragments by human HNC cancer cell lines (HSC-2 and FaDu) and a control cell line HEK was evaluated using flow cytometry. The results represent internalized plus cell surface bound compounds that occurs when cells have been incubated at +37° C. (Table 3). Anti-EGFR1-Fab-BSH(1200B)-Dex and nonconjugated anti-EGFR1-Fab showed strongest internalization by HSC-2 and FaDu cells. Internalization by FaDu cells has been consistently weaker than by HSC-2 cells, likely due to the smaller amount of EGFR1 receptors at the cell surface. Control boron conjugates (control-Fab-BSH (800B)-Dex and control-F(ab')2-BSH(800B)-Dex) and corresponding nonconjugated compounds were internalized very weakly. Control cell line HEK internalized the boron conjugates and nonconjugated compounds only very weakly.

TABLE 3

Cell surface binding and internalization of fluorescently labeled boron conjugates (1200B or 800B) and nonconjugated compounds by HSC-2, FaDu and HEK cells. Analysis has been carried out by flow cytometry and fluorescence intensity has been normalized to the degree of labeling for each compound.

| Sample | HSC-2 | FaDu | HEK |
|---|---|---|---|
| | Normalized mean fluorescence intensity | | |
| Anti-EGFR1-Fab | 43006 | 6820 | 274 |
| Anti-EGFR1-F(ab')2 | 18432 | 3461 | 168 |
| Control-Fab | 1165 | 970 | 555 |
| Control-F(ab')2 | 823 | 443 | 337 |
| Anti-EGFR1-Fab-BSH(1200)-Dex | 45270 | 8060 | 615 |
| Anti-EGFR1-F(ab')2-BSH(1200)-Dex | 10043 | 2813 | 198 |
| Control-Fab-BSH(800)-Dex | 1233 | 428 | 158 |
| Control-F(ab')2 -BSH(800)-Dex | 236 | 169 | 61 |

Internalization Assay with Radiolabeled Samples

HSC-2, FaDu and HEK cells ($2 \times 10^5$) were seeded on a 24 well plate and allowed to grow for 24 h. Then the cells were incubated for 3 h at +37° C. in 300 µl media containing 5 µg/ml tritium labeled compounds. After incubation media was removed and cells were washed three times with PBS and lysed by adding 300 µl 1 M NaOH. The amount of radioactivity in media and cell lysates was measured with scintillation counter in the presence of scintillation fluid cocktail (Ultima Gold). The amount of internalized compounds was calculated from the total amount of radioactivity per well and normalized to 100 000 cells.

Boron conjugates (800 boron atoms) of anti-EGFR1-Fab and -F(ab')2 as well as nonconjugated anti-EGFR1-mAb were labeled with tritium to the lysine residues of a protein part. Internalization assay with radiolabeled compounds was carried out using human HNC cancer cell lines, HSC-2 and FaDu, as well as a control cell line HEK. The results represent internalized plus cell surface bound compounds that occur when cells have been incubated at +37° C. The results (Table 4) indicate that boron conjugates of anti-EGFR1-Fab and -F(ab')2 were internalized as efficiently as nonconjugated anti-EGFR1-mAb by HSC-2 and FaDu cells. Internalization by HSC-2 cells was 100 times stronger than by FaDu cells likely due to the higher amount of EGFR1 receptors at the cell surface in HSC-2 cells. Control cell line HEK showed only very weak internalization.

TABLE 4

Internalization of radiolabeled boron conjugates by HSC-2, FaDu and HEK cells. The amount of internalized compounds has been calculated from the total amount of radioactivity per well and normalized to 100 000 cells. The results are an average of three determinations +/− S.D.

| Samples | HSC-2 | FaDu | HER |
|---|---|---|---|
| | % internalized/100000 cells | | |
| Anti-EGFR1-Fab-BSH(800B)-Dex | 4.0 ± 0.3 | 0.04 ± 0.02 | 0.004 ± 0.001 |
| Anti-EGFR1-F(ab')2-BSH(800B)-Dex | 5.4 ± 1.0 | 0.06 ± 0.02 | 0.006 ± 0.001 |
| Anti-EGFR1-mAb | 5.0 ± 0.5 | 0.04 ± 0.02 | 0.007 ± 0.001 |
| Control-mAb | 0.1 ± 0.1 | 0.01 ± 0.01 | 0.002 ± 0.002 |

Example 8. In Vivo Experiments with Tritium Labeled Conjugates

Preparation of Mouse Tissues and Blood Samples for Liquid Scintillation Counting Weighted mouse organs were dissolved to 1 ml of tissue solubilizer (Solvable™, Perkin Elmer) per 0.2 g tissue. Samples were incubated overnight at +60° C. Then 150 µl of $H_2O_2$ was added per 300 µl of dissolved organ and samples were incubated for one hour at +60° C. Bones were treated first with 1 M HCl overnight at +60° C. and then with Solvable and $H_2O_2$. The amount of radioactivity in the organs was measured with scintillation counter in a presence of scintillation fluid cocktail (Ultima Gold™, Perkin Elmer). Data is presented as percent of total injected dose in g of tissue. The results are an average of three mice+/−SEM. Since each of the mice had two tumors, the results in tumors are an average of six determinations+/−SEM.

Blood samples in clearance tests were collected in Eppendorf tubes and the volumes were measured after adding 100 µl of Solvable and overnight incubation at +60° C. Then 100 µl of $H_2O_2$ was added and samples were incubated for one hour at +60° C. The amount of radioactivity in the blood samples was measured with scintillation counter in the presence of scintillation fluid cocktail (Ultima Gold, Perkin Elmer). Data is presented as a percent of total injected dose. The results are an average of two mice.

Blood Clearance of Boron Conjugates in Non-Tumor Mice

Female adult mice of the same age (Harlan HSD:Athymic nude Foxn1nu) were used. Radiolabeled (3H) boron conjugates of anti-EGFR1-Fab and -F(ab')2 with 800B and 300B boron load were injected i.v. via tail vein in 100 µl PBS. Injected dose was 30 µg=1.3-2×106 cpm per mouse and two mice per sample were used. Blood samples of approximately 10 µl were collected before and after injection at different time points and counted for radioactivity. At the end of the experiment (48 h) mice were sacrificed and organs were collected and counted for radioactivity for determination of tissue biodistribution of the conjugates.

Blood clearance study in non-tumor mice was carried out using 3H-labeled boron conjugates of anti-EGFR1-Fab and -F(ab')2 with 800B and 300B boron load. Two different boron loads were used to see whether the boron load has an effect on the clearance rate of the conjugate from blood circulation. The results indicate that blood clearance of boron conjugates was rapid and independent on the boron load (Table 5). Clearance rate was comparable to the clearance of corresponding non-conjugated F(ab')2 and Fab fragments (not shown). Tissue distribution study indicated that the boron conjugates were not accumulated into any organs at 48 h (not shown).

TABLE 5

Blood clearance of boron conjugates in non-tumor mice. The results are an average of two determinations. Time is time after administration (min) and values % of total injected dose.

| Time | Anti-EGFR-Fab-BSH(300)-Dex | Anti-EGFR-Fab-BSH(800)-Dex | Anti-EGFR-Fab2-BSH(300)-Dex | Anti-EGFR-Fab2-BSH(800)-Dex |
|---|---|---|---|---|
| 0 | 100.0 | 100.0 | 100.0 | 100.0 |
| 5 | 35.4 | 31.3 | 42.9 | 40.8 |
| 15 | 31.8 | 19.9 | 34.3 | 20.2 |
| 30 | 26.7 | 10.5 | 29.3 | 16.3 |
| 60 | 13.6 | 10.7 | 22.6 | 9.7 |
| 120 | 6.8 | 5.2 | 16.1 | 6.3 |
| 240 | 4.6 | 2.5 | 9.4 | 4.3 |
| 460 | 2.4 | 2.0 | 4.1 | 1.7 |
| 1440 | 0.9 | 0.8 | 1.7 | 1.1 |
| 2880 | 0.4 | 0.4 | 0.6 |  |

Biodistribution of Boron Conjugates in HSC-2 Tumor Mice

Female adult mice of the same age (Harlan HSD:Athymic nude Foxn1nu) were used. Two and half to three million HSC-2 cells (JCRP Cellbank, Japan) in 150 µl in EME-media and 50% Matrigel were inoculated to both flanks of nude mice. The dosing was given when at least one tumor per mouse has grown to at least 6 mm diameter in size (6-10 mm) corresponding roughly to tumor volume of 100-500 mm$^3$. Radiolabeled (3H) boron conjugates (800B) of anti-EGFR1-Fab/F(ab')2 and control-Fab/F(ab')2 were injected i.v. via tail vein in 100 µl PBS. Injected dose was 50 µg=1.3-2.6×106 cpm per mouse and three mice per sample were used. Mice were sacrificed at different time points (24 h, 48 h and 72 h) and organs were collected and counted for radioactivity for determination of tissue biodistribution of the conjugates.

Tissue distribution of boron conjugates (Table 6) show that boron conjugates of anti-EGFR1-Fab and -F(ab')2 accumulated into tumors but not in any other organs, whereas control boron conjugates did not significantly accumulate into tumors. Tumor accumulation of boron conjugates of anti-EGFR1-Fab and -F(ab')2 was highest at 24 h and slowly decreased at later time points (48 h and 72 h).

TABLE 6

Biodistribution of boron conjugates in HSC-2 tumor mice. The results represent an average of three determinations +/− SEM except for tumors that are an average of six determinations +/− SEM. Values are % of total injected dose/g organ.

| Organ | Anti-EGFR-Fab-BSH(800)-Dex | Anti-EGFR-Fab2-BSH(800)-Dex | Control-Fab-BSH(800)-Dex | Control-Fab2-BSH(800)-Dex |
|---|---|---|---|---|
| 24 h | | | | |
| blood | 0.23 ± 0.02 | 0.34 ± 0.07 | 0.23 ± 0.05 | 0.47 ± 0.23 |
| urine | 0.16 ± 0.07 | 2.22 ± 0.9 | 0.94 ± 0.05 | 3.03 ± 1.16 |
| liver | 0.34 ± 0.03 | 0.28 ± 0.03 | 0.26 ± 0.07 | 0.29 ± 0.14 |
| kidney | 0.28 ± 0.01 | 0.31 ± 0.04 | 0.24 ± 0.05 | 0.32 ± 0.15 |
| lung | 0.19 ± 0.02 | 0.44 ± 0.14 | 0.19 ± 0.04 | 0.45 ± 0.30 |
| muscle | 0.19 ± 0.01 | 0.21 ± 0.05 | 0.17 ± 0.06 | 0.20 ± 0.09 |
| skin | 0.23 ± 0.02 | 0.31 ± 0.03 | 0.22 ± 0.04 | 0.29 ± 0.15 |
| tumor | 1.00 ± 0.08 | 0.75 ± 0.15 | 0.32 ± 0.60 | 0.57 ± 0.27 |
| 48 h | | | | |
| blood | 0.10 ± 0.02 | 0.10 ± 0.01 | 0.10 ± 0.01 | 0.20 ± 0.02 |
| urine | 0.36 ± 0.11 | 0.46 ± 0.04 | 0.28 ± 0.17 | 1.00 ± 0.32 |
| liver | 0.23 ± 0.04 | 0.18 ± 0.03 | 0.15 ± 0.01 | 0.14 ± 0.03 |
| kidney | 0.17 ± 0.02 | 0.14 ± 0.01 | 0.15 ± 0.02 | 0.17 ± 0.01 |
| lung | 0.10 ± 0.02 | 0.10 ± 0.01 | 0.09 ± 0.02 | 0.12 ± 0.01 |
| muscle | 0.11 ± 0.01 | 0.12 ± 0.01 | 0.11 ± 0.01 | 0.15 ± 0.01 |
| skin | 0.12 ± 0.01 | 0.14 ± 0.01 | 0.11 ± 0.04 | 0.18 ± 0.02 |
| tumor | 0.41 ± 0.06 | 0.58 ± 0.06 | 0.21 ± 0.03 | 0.29 ± 0.02 |
| 72 h | | | | |
| blood | 0.06 ± 0.01 | 0.08 ± 0.01 | 0.08 ± 0.01 | 0.10 ± 0.01 |
| urine | 0.23 ± 0.07 | 0.24 ± 0.10 | 0.23 ± 0.02 | 0.30 ± 0.05 |
| liver | 0.11 ± 0.01 | 0.15 ± 0.02 | 0.12 ± 0.01 | 0.09 ± 0.01 |
| kidney | 0.11 ± 0.02 | 0.12 ± 0.01 | 0.12 ± 0.01 | 0.12 ± 0.01 |
| lung | 0.05 ± 0.01 | 0.06 ± 0.01 | 0.05 ± 0.01 | 0.08 ± 0.01 |
| muscle | 0.07 ± 0.01 | 0.10 ± 0.02 | 0.09 ± 0.01 | 0.08 ± 0.02 |
| skin | 0.08 ± 0.01 | 0.11 ± 0.01 | 0.08 ± 0.01 | 0.09 ± 0.01 |
| tumor | 0.25 ± 0.04 | 0.30 ± 0.05 | 0.11 ± 0.01 | 0.18 ± 0.02 |

Tumor vs. blood distribution of boron conjugates in HSC-2 xenograft mice was calculated at different time points (24 h, 48 h and 72 h) (Table 7). Tumor/blood ratio was 4-5 for anti-EGFR1-Fab conjugate and 2-6 for anti-EGFR1-F(ab')2 conjugate. Anti-EGFR1-Fab-BSH-Dex reached the maximum ratio earlier (24 h) than anti-EGFR1-F(ab')2-BSH-Dex (48 h). Tumor/blood ratio of control conjugates remained at a constant level throughout the study (approximately 1-2).

TABLE 7

Tumor/blood distribution of boron conjugates in HSC-2 tumor mice. The results are based on an average of three determinations for blood samples and an average of six determinations for tumors (2 tumors per mouse) +/− S.D.

| Boron conjugate | 24 h | 48 h | 72 h |
|---|---|---|---|
| Anti-EGFR-Fab-BSH(800B) | 4.2 ± 0.3 | 4.2 ± 1.1 | 4.0 ± 0.9 |
| Anti-EGFR-Fab2-BSH(800B)-dex | 2.2 ± 0.3 | 6.1 ± 1.4 | 3.8 ± 1.0 |
| Control-Fab-BSH(800B)-dex | 1.5 ± 0.3 | 2.2 ± 0.5 | 1.5 ± 0.3 |
| Control-Fab2-BSH(800B)-dex | 1.5 ± 0.5 | 1.8 ± 0.2 | 1.9 ± 0.5 |

Biodistribution of Boron Conjugates in FaDu Tumor Mice

Female adult mice of the same age (Charles River Crl: Athymic nude Foxn1nu) were used. Three million FaDu cells (ATCC) in 150 µl in EME-media and 50% Matrigel were inoculated to both flanks of nude mice. The dosing was given when at least one tumor per mouse has grown to at least 6 mm diameter in size (6-10 mm) corresponding roughly to tumor volume of 100-500 mm$^3$. Radiolabeled (3H) boron conjugates (800B or 1200B) of anti-EGFR1-Fab/F(ab')2 and control-Fab/F(ab')2 were injected i.v. via tail vein in 100 µl PBS. Injected dose was 50 µg=2.3-2.7×10$^6$ cpm per mouse and three mice per sample were used. Mice were sacrificed at two different time points (24 h and 48 h) and organs were collected and counted for radioactivity for determination of tissue biodistribution of the conjugates.

Biodistribution study in FaDu xenograft tumor mice was carried out using anti-EGFR1-F(ab')2-BSH(800B)-Dex and anti-EGFR1-Fab(800B or 1200B)-BSH-Dex and boron conjugates (800B) of control-F(ab')2 and -Fab. The conjugates were radiolabeled (3H) to lysine residues of a protein. Radioactivity in tissue samples, including tumors and blood, were counted at two different time points (24 h and 48 h). Tissue distribution of boron conjugates (Table 8) show that boron conjugates of anti-EGFR1-Fab and -F(ab')2 accumulated into tumors but not significantly in any other organs, whereas control boron conjugates did not significantly accumulate into tumors. Control-F(ab')2-BSH(800B)-Dex can be still be found in blood circulation and in all organs at 24 h, but is cleared from circulation at 48 h. Tumor accumulation of boron conjugates of anti-EGFR1-Fab and -F(ab')2 was highest at 24 h and decreased at 48 h.

TABLE 8

Biodistribution of boron conjugates in FaDu tumor mice. The results represent an average of three determinations +/− SEM except for tumors that are an average of six determinations +/− SEM. values are % of total injected dose/g organ.

| Organ | Anti-EGFR-Fab-BSH(800)-Dex | Anti-EGFR-Fab-BSH(1200)-Dex | Anti-EGFR-Fab2-BSH(1200)-Dex | Control-Fab-BSH(800)-Dex | Control-Fab2-BSH(800)-Dex |
|---|---|---|---|---|---|
| 24 h | | | | | |
| blood | 0.34 ± 0.03 | 0.13 ± 0.01 | 0.10 ± 0.01 | 0.20 ± 0.02 | 0.52 ± 0.05 |
| urine | 2.45 ± 0.58 | 0.94 ± 0.06 | 0.59 ± 0.25 | 1.95 ± 0.38 | 3.48 ± 0.42 |
| liver | 0.30 ± 0.02 | 0.35 ± 0.01 | 0.29 ± 0.04 | 0.30 ± 0.04 | 0.38 ± 0.05 |
| kidney | 0.29 ± 0.01 | 0.21 ± 0.02 | 0.15 ± 0.02 | 0.29 ± 0.02 | 0.44 ± 0.05 |
| lung | 0.15 ± 0.01 | 0.11 ± 0.01 | 0.09 ± 0.02 | 0.18 ± 0.01 | 0.32 ± 0.04 |
| muscle | 0.15 ± 0.01 | 0.16 ± 0.02 | 0.11 ± 0.01 | 0.19 ± 0.01 | 0.24 ± 0.03 |
| skin | 0.20 ± 0.02 | 0.21 ± 0.04 | 0.16 ± 0.01 | 0.23 ± 0.04 | 0.53 ± 0.09 |
| tumor | 1.44 ± 0.34 | 0.93 ± 0.23 | 0.73 ± 0.10 | 0.41 ± 0.06 | 0.86 ± 0.13 |
| 48 h | | | | | |
| blood | 0.14 ± 0.04 | 0.12 ± 0.01 | 0.08 ± 0.01 | 0.13 ± 0.01 | 0.22 ± 0.04 |
| urine | 0.77 ± 0.07 | 0.33 ± 0.05 | 0.42 ± 0.08 | 0.66 ± 0.09 | 1.05 ± 0.15 |
| liver | 0.17 ± 0.03 | 0.14 ± 0.03 | 0.18 ± 0.04 | 0.16 ± 0.01 | 0.15 ± 0.03 |
| kidney | 0.14 ± 0.01 | 0.12 ± 0.02 | 0.12 ± 0.02 | 0.17 ± 0.01 | 0.17 ± 0.02 |
| lung | 0.09 ± 0.01 | 0.08 ± 0.02 | 0.07 ± 0.01 | 0.11 ± 0.01 | 0.13 ± 0.01 |
| muscle | 0.12 ± 0.01 | 0.11 ± 0.03 | 0.10 ± 0.01 | 0.13 ± 0.01 | 0.13 ± 0.02 |
| skin | 0.11 ± 0.01 | 0.08 ± 0.02 | 0.09 ± 0.01 | 0.13 ± 0.01 | 0.16 ± 0.01 |
| tumor | 0.70 ± 0.11 | 0.39 ± 0.13 | 0.31 ± 0.04 | 0.19 ± 0.02 | 0.24 ± 0.04 |

Tumor Vs. Blood Distribution of Boron Conjugates in FaDu xenograft mice was calculated at 24 h and 48 h (Table 9). Tumor/blood ratio was approximately 7 for anti-EGFR1-Fab and -F(ab')2 conjugates with 1200 borons at 24 h, and the ratio decreased to 3-4 at 48 h suggesting that the labeled protein is degraded and is secreted out of the cells. Tumor/blood ratio of anti-EGFR1-Fab conjugate with 800 borons was approximately 4-5 at both time points. The ratio of control conjugates remained at a constant level (approximately 1-2).

TABLE 9

Tumor/blood distribution of boron conjugates in FaDu tumor mice. The results are based on an average of three determinations for blood samples and an average of six determinations for tumors (2 tumors per mouse) +/− S.D.

| Boron conjugate | 24 h | 48 h |
|---|---|---|
| anti-EGFR-Fab-BSH(800)-dex | 4.4 ± 2.2 | 5.5 ± 1.5 |
| anti-EGFR-Fab-BSH(1200)-dex | 6.9 ± 2.8 | 3.4 ± 2.0 |
| anti-EGFR-Fab2-BSH(1200)-dex | 7.6 ± 1.7 | 4.2 ± 1.1 |
| control-Fab-BSH(800)-dex | 1.8 ± 0.5 | 1.5 ± 0.2 |
| control-Fab2-BSH(800)-dex | 1.7 ± 0.4 | 1.2 ± 0.4 |

Example 9. Quantitation of Boron in BSH-Dextran by Inductively Coupled Plasma Mass Spectrometry (ICP-MS) (Mol Boron Per Mol BSH-Dextran)

The boron load of BSH-dextran was estimated from proton-NMR spectrum of BSH-dextran (FIG. 1) and ICP-MS was used to quantitate the amount of boron in the samples. The BSH-Dextran sample analyzed in this example was estimated to contain about 1200 borons based on NMR analysis. Approximately 2.1 µg (0.0228 nmol) of BSH-Dextran (average MW 92 kDa) was liquefied with microwave-assisted wet asking and analyzed by ICP-MS essentially as described in Laakso et al., 2001, Clinical Chemistry 47, 1796-1803. Different dilutions of the sample were analyzed by ICP-MS and the background boron was subtracted from the samples. The results representing an average of 7 determinations indicate that the sample contains approximately 0.341 µg (31.5 nmol) of boron atoms, or one mole of the BSH-Dextran contain 1381 moles of boron atoms.

Example 10. In Vivo Experiments and Boron Quantitation

Female adult mice of the same age (Charles River Crl: Athymic nude Foxn1nu) were used. 2.3 million HSC-2 or 5 million FaDu cells in 150 µl in EME-media and 50% Matrigel were inoculated to the right flank of nude mice. The dosing was given when the tumor was grown to at least 6 mm diameter in size (6-mm) corresponding roughly to tumor volume of 100-500 mm$^3$. Anti-EGFR-Fab-BSH (1200)-dex or anti-EGFR-F(ab')2-BSH(1200)-dex (both non-labeled) conjugates were injected i.v. via tail vein in 100 µl PBS. Injected dose was 50 µg or 250 µg per mouse and three mice per sample were used. Mice were sacrificed at 24 h and 48 h and organs were collected for boron determination.

Tissue samples (including blood) were digested in closed teflon vessels in a microwave oven (Milestone, ETHOS 1200). The digestion temperature was 200 C and duration of the digestion was 50 min. Acid used in the digestions was $HNO_3$ (6.0 ml, E. Merck, Suprapur). After cooling the resultant solution was diluted to 25 ml with Milli-Q water. The digested samples were diluted further (1:10 or 1:50) with 1% $HNO_3$ for ICP-MS analysis. The internal standard beryllium was added to the sample to gain the final concentration, 10 ppb of Be, in the samples. Standard solutions with concentrations of 1, 5, 10 and µg/L for analyses were diluted from Spectrascan's single element standard solution (1000 ug/ml boron as $H_3BO_3$ in $H_2O$). Control sample for analysis was prepared from multielemental standard solution by SPEX (CLMS-4). Analyses were performed with the high resolution sector field inductively coupled plasma mass spectrometer (HR-ICP-MS, Element2, Thermo Scientific). The concentration of boron in diluted samples was defined from the peaks of 10B and 11B with both low resolution (R≈300) and medium resolution (R≈4000) mode. Between the samples the samples introduction system was washed first with 5% $HNO_3$ and then with 1% $HNO_3$ to exclude the memory effect typical for boron.

Initial boron analysis of two HSC-2 tumor mice at 24 h indicated that boron tumor per muscle ratios were 5.3 and 6.3.

The muscle was used as a control tissue instead of blood because initial boron measurements from blood were inconclusive or beyond detection limit.

Example 11. In Vivo Experiments with $^{14}C$ Labelled Anti-EGFR1 Fab BSH-Dextran Preparation of Anti-EGFR1 Fab BSH-Dextran BSH-dextran was prepared as described in Examples 1 and 2, respectively. According to NMR analysis the BSH-dextran contained approximately 650 borons. The oxidation was made as described in Example 3 but in two batches; one with 50 mg and the other with 100 mg BSH-dextran.

Anti-EGFR1 Fab fragments were prepared by papain digestion as described in Example 5. Conjugation reactions were carried out as in Example 4 but in four batches: 1) 29 mg oxidized BSH-dextran and 10.4 mg anti-EGFR1 Fab, 2) 16.5 mg oxidized BSH-dextran and 5.9 mg anti-EGFR1 Fab, 3) 50 mg oxidized BSH-dextran and 19.8 mg anti-EGFR1 Fab, 4) 50 mg oxidized BSH-dextran and 19.7 mg anti-EGFR1 Fab yielding together 55.8 mg of anti-EGFR1 Fab. All were analyzed in SDS-PAGE as in Example 6 and samples of each were labeled with Alexa Fluor 488-NHS. Internalization assay with Alexa Fluor 488 labeled molecules was performed with HSC-2 cells as described in Example 7.

Unlabeled Fab-BSH-dextran batches were combined to yield 39 mg of Anti-EGFR1 Fab BSH-dextran. The sample buffer was changed to 5% Mannitol-0.1% Tween80 in PBS prior to combining unlabeled and $^{14}C$ labelled anti-EGFR1 Fab BSH-dextran and subsequent sterile filtration.

Preparation of $^{14}C$ Labelled Anti-EGFR1 Fab BSH-Dextran 3 mg Fab-BSH-dextran (before ethanolamine capping) was $^{14}C$ labelled by incubation with 66 µCi $^{14}C$-ethanolamine (American Radiolabeled Chemicals Inc.) in PBS containing $NaCNBH_3$ (as in Example 4) o/n after which the capping was finished with non-radioactive ethanolamine for 2 hours, and the low molecular weight reagents were removed as described in Example 4. This reaction resulted in $^{14}C$ labelled anti-EGFR1 Fab BSH-dextran containing 9.21 µCi radioactivity.

For the animal study $^{14}C$ labeled anti-EGFR1 Fab BSH dextran was mixed with unlabeled "cold" anti-EGFR1 Fab BSH dextran in portions shown in Table 10.

TABLE 10

Preparation of test materials.

| Group | Amount of $^{14}C$ labelled anti-EGFR1 Fab BSH-dextran (µg of Fab) | Amount of "cold" anti-EGFR1 Fab BSH-dextran (µg of Fab) |
|---|---|---|
| I | 250 | 750 |
| II | 250 | 1750 |
| III | 250 | 3750 |
| IV | 250 | 5750 |
| V | 250 | 7750 |
| X | 250 | 750 |
| VIII | 250 + 250 | 1500 |
| IX | 250 + 250 | 1500 |

In Vivo Experiment with $^{14}C$ Labelled Anti-EGFR1 Fab BSH-Dextran

Xenograft mice were generated as described in Example 8 except that HSC-2 cells were inoculated in right flank and the dosing was given the tumor had grown to at least 8 mm diameter in size (8-12 mm) corresponding roughly to tumor volume of 200-800 $mm^3$. Radiolabeled ($^{14}C$) anti-EGFR1-Fab boron conjugates were injected either i.v. via tail vein or by intratumoral injection (Group X) in 100 µl PBS containing 5% mannitol and 0.1% polysorbate (study groups are listed in Table 10). Three mice per sample were used. Each mouse were administered about 400000 cpm of the conjugate (see above the preparation of the anti-EGFR1 Fab BSH dextran conjugates for the animal study; Table 10). Mice were sacrificed at 24 h or 48 h (Group IX) and organs were collected and counted for radioactivity for determination of tissue biodistribution of the conjugates. Blood samples were also collected at 30 min, 2 h, and 8 h after administration of boron conjugates.

Tissues were prepared for $^{14}C$ quantitation as described in Example 8. Blood samples in clearance tests were prepared as in Example 8 with the exception that 200 µl of Solvable and 90 µl of $H_2O_2$ were used. The results are an average of three mice.

Table 11 shows tumor to blood ratios for the mice administered with $^{14}C$ labelled anti-EGFR1 Fab dextran conjugate.

TABLE 11

Tumor/blood ratio of $^{14}C$ boron conjugate in HSC-2 tumor mice. The value for G IX is tumor/brain ratio as radioactivity in blood was determined to be 0% (all blood samples were negative after deduction of background levels). Group I: 250 µg; Group II: 500 µg; Group III 1000 µg; Group IV: 1500 µg; Group V: 2000 µg; Group X: 250 µg; Group VIII: 250 µg + 250 µg after 2 h; and Group IX: 250 µg + 250 µg after 24 h. All Groups i.v. except Group X intratumoral administration. Organs collected at 24 h except Group IX at 48 h. Tumor/blood ratio of Group VIII from one mouse (due to presence of one blood cpm value in the group).

| G I | G II | G III | G IV | G V | G X | G VIII | G IX |
|---|---|---|---|---|---|---|---|
| 11.2 | 12.8 | 9.7 | 23.8 | 28.8 | 4394.3 | 9.3 | 6.2 |

TABLE 12

Blood clearance of $^{14}C$ boron conjugates in the three groups. Left column shows time after administration (min/h) and values are % of total injected dose/g blood.

|  | G I | G III | G V |
|---|---|---|---|
| 30 min | 6.546 ± 0.991% | 9.809 ± 0.876% | 7.486 ± 0.235% |
| 2 h | 1.461 ± 0.256% | 2.802 ± 0.416% | 1.854 ± 0.608% |
| 8 h | 0.489 ± 0.034% | 0.74 ± 0.055% | 1.76 ± 1.109% |
| 24 h | 0.089 ± 0.016% | 0.122 ± 0.014% | 0.086 ± 0.051% |

Example 12. In Vivo Experiments with Anti-EGFR1 Fab BSH-Dextran by Direct Boron Quantitation Preparation of Anti-EGFR1 Fab BSH-Dextran Anti-EGFR1 Fab BSH-dextran was prepared as described in Examples 1 and 2, respectively. The oxidation was made as described in Example 3 but in two batches; one with 80 mg, the other with 96 mg BSH-dextran. According to NMR analyses the BSH-dextran samples contained approximately 880 and 500 borons, respectively.

Anti-EGFR1 Fab fragments were prepared by papain digestion as described in Example 5. Conjugation reactions were carried out as in Example 4 but in four batches: two with 15.7 mg Anti-EGFR1 Fab and 40 mg ox-BSH-dextran, other two with 18.8 mg Anti-EGFR1 Fab and 48 mg ox-BSH-dextran.

All boron conjugates were analyzed in SDS-PAGE as in Example 6 and were labeled with Alexa Fluor® 488-NHS. Internalization assay with HSC-2 cells was performed with the Alexa Fluor labelled molecules as described in Example 7.

The sample buffer was changed to 5% Mannitol-0.1% Tween80 in PBS prior to mouse trial sample preparation and sterile filtration.

In Vivo Experiment with Anti-EGFR Fab BSH-Dextran

Xenograft mice were generated as in Example 11. Anti-EGFR Fab BSH-dextran was administered in 100 µl of mannitol/Tween/PBS solution i.v. or in 40 µl of mannitol/Tween/PBS solution intratumorally (i.t.). In i.t. administration the needle was passed into the tumor through a single injection site and moved in a fanning technique to distribute the test substance throughout the tumor. Depending on tumor size and shape, a total of three or four passes was used.

Organs were collected at 24 h and blood samples were collected at 30 min, 2 h, and 8 h (study groups II and V).

Quantitation of Boron

Tissues were prepared for direct boron quantitation by ICP-MS as described above. Three control samples containing ~150 mg NIST reference standard 1573 tomato leaves were also digested. The digested samples were diluted to 1:10 or 1:100.

Table 13 illustrates boron in selected organs and Table 14 shows tumor to blood ratios. Intratumoral administration shows considerably higher tumor boron concentration compared to i.v. administration.

TABLE 13

Biodistribution of anti-EGFR1 Fab BSH-dextran conjugates in HSC-2 tumor mice by boron quantitation. The results represent an average of four determinations +/− SEM. Study groups were: Group I: buffer only (mannitol/Tween/PBS) i.v.; Group II: 2 mg i.v.; Group III: 2 mg + dextran i.v.; Group IV: 250 µg i.t.; Group V: 2 mg i.t. Values are µg boron in g of organ. Students t-test was performed (using Statistica 12 software [StatSoft]) for tumor boron values of Groups II vs III and for Groups IV vs V. Groups IV and V showed significant difference between boron quantities (p-value = 0.009).

|  | Group II | Group III | Group IV | Group V | Group I |
|---|---|---|---|---|---|
| Blood | 0.56 ± 0.18 | 0.87 ± 0.14 | 0.1 ± 0.05 | 0.22 ± 0.01 | 0.32 ± 0.21 |
| Liver | 18.3 ± 1.25 | 17.54 ± 1.15 | 1.02 ± 0.33 | 6.97 ± 0.86 | 0.27 ± 0.09 |
| Kidney | 6.57 ± 0.57 | 6.44 ± 0.41 | 0.87 ± 0.27 | 3.78 ± 0.24 | 0.76 ± 0.31 |
| Muscle | 1.87 ± 0.34 | 1.51 ± 0.9 | 0.56 ± 0.25 | 0.7 ± 0.31 | 0.87 ± 0.51 |
| Skin | 2.11 ± 0.16 | 1.46 ± 0.14 | 0.43 ± 0.13 | 1.27 ± 0.85 | 0.17 ± 0.09 |
| Tumor | 2.19 ± 1.01 | 9.54 ± 8.59 | 9.22 ± 2.3 | 53.09 ± 11.45 | 0.62 ± 0.53 |
| Spleen | 4.95 ± 0.9 | 5.91 ± 0.88 | 2.01 ± 0.5 | 1.88 ± 0.59 | 1.34 ± 0.53 |

TABLE 14

Tumor to blood ratios +/− SEM.

| Group II | Group III | Group IV | Group V | Group I |
|---|---|---|---|---|
| 10.8 ± 7.1 | 13.6 ± 12.5 | 131.3 ± 40.7 | 240.8 ± 49.4 | 4.6 ± 3.6 |

Example 13. Production of Anti-EGFR1 Fab in *E. coli*

Optimization of the Signal Peptide for Periplasmic Secretion of Anti-EGFR1 Fab

Expression strategy for anti-EGFR1 Fab was targeting to periplasm, where stable disulfide bridges can be formed.

Commercial vector set pDD441-SSKT (T5 promoter, kanamycin selection) was used for optimization of the signal peptide. Following signal peptides were used: i) MalE (maltose binding protein), ii) pelB (pectate lyase), iii) ompA (outer membrane protein A), iv) phoA (bacterial alkaline phosphatase) and v) gIII (PRV envelope glycoprotein). Vectors pGF115-pGF119 were constructed by using synthetic DNA sequences, PCR amplification with high fidelity polymerase and seamless Gibson assembly as routine tools. In addition, vector pGF150 with signal peptide stII (heat stabile enterotoxin II) for both heavy- and light chain was constructed according to Carter et al 1992: High level *E. coli* expression and production of bivalent humanized antibody fragment, Biotechnology (N Y), 10(2) 163-7. Vector pGF150 was dicistronic and had T7 promoter for expression. Expression cassette for anti-EGFR1 Fab was dicistronic with internal ribosome binding site between the heavy and light chain. General expression vector setup for signal peptide optimization is exemplified in FIG. 5. Signal peptide combinations in vectors pGF115-pGF119 are listed in Table 15.

with peroxidase conjugate (Sigma Aldrich; cat no A0293) and Luminata Forte Western HRP substrate (Millipore; cat no WBLUF0500). Chemiluminescense reaction was detected with Fujifilm Luminescent Image Analyzer LAS4000.

According to Western blot analyses from several expression cultures, vectors pGF119 and pGF115 seemed to be

TABLE 15

Signal peptide combinations in vectors pGF115-pGF119.

| Vector | Heavy chain signal peptide | Light chain signal peptide |
| --- | --- | --- |
| pGF115 | >gIII<br>MKKLLFAIPLVVPFYSHS (SEQ ID NO: 16) | >ompA<br>MKKTAIAIAVALAGFATVAQA<br>(SEQ ID NO: 17) |
| pGF116 | >malE<br>MKIKTGARILALSALTTMMFSASALA (SEQ ID NO: 18) | >ompA<br>MKKTAIAIAVALAGFATVAQA<br>(SEQ ID NO: 17) |
| pGF117 | >phoA<br>MKQSTIALALLPLLFTPVTKA (SEQ ID NO: 19) | >ompA<br>MKKTAIAIAVALAGFATVAQA<br>(SEQ ID NO: 17) |
| pGF118 | >pelB<br>MKYLLPTAAAGLLLLAAQPAMA (SEQ ID NO: 20) | >ompA<br>MKKTAIAIAVALAGFATVAQA<br>(SEQ ID NO: 17) |
| pGF119 | >ompA<br>MKKTAIAIAVALAGFATVAQA (SEQ ID NO: 17) | >pelB<br>MKYLLPTAAAGLLLLAAQPAMA<br>(SEQ ID NO: 20) |
| pGF150 | >stII<br>MKKNIAFLLASMFVFSIATNAYA (SEQ ID NO: 21) | >stII<br>MKKNIAFLLASMFVFSIATNAYA<br>(SEQ ID NO: 21) |

Vectors pGF115-pGF119 were transformed to electrocompetent E. coli W3110 (ATCC microbiology collection) cells with Biorad GenePulser, pulsed with program Ec2 according to manufacturer's instructions. Transformations were plated to LB+agar+kanamycin 25 mg/L and cultivated o/n at +37° C.

Single colonies were subjected to expression screening according to standard protocol. On day 1, o/n precultures were inoculated to 5 ml of liquid LB supplemented with kanamycin with final concentration 20 mg/L, cultivated with shaking 220 rpm, +37°. On day 2, 200 µL of o/n preculture was re-inoculated to 10 mL of liquid LB+kanamycin 10 mg/L. Culture was continued with shaking 220 rpm, +37°, until $OD_{600}$ reached the level 0.6-0.9. Fab production was induced with IPTG, final concentration 500 µM. Culture was continued with shaking 220 rpm, +20° C., o/n. 1 mL samples were collected from post-induction time points 4 h and o/n. Cells were harvested by centrifugation 8000×G 10 min, supernatant was discarded, pellet was resuspended to 100 µl of 10×TE pH 7.5 (100 mM Tris-HCl, 10 mM EDTA). Samples were vortexed vigorously 1 h at r/t, pelleted 16 000×G 10 min and sup was collected to fresh Eppendorf tube as a periplasmic extract.

Periplasmic extracts were further analyzed with Western blot. 100 µl of extract was mixed with 20 µl of either reducing- or non-reducing loading buffer. 20 µl of mix was loaded into 4-20% Precise Tris-Glycine SDS-Page gel (Thermo Scientific). Gel was run in 1× Laemmli running buffer 200 V~45 min and blotted to nitrocellulose membrane in Tris-Glycine blotting buffer, 350 mA~45 min. BioRad Mini-protean system was used for SDS-Page and blotting. Blotted membrane was blocked with 1% BSA in PBS. Detection was made with anti-human IgG (Fab specific)

better than the others. The amount of Fab produced to the periplasm remained, however, at the level of 0.3-0.8 mg/L in these initial experiments. Combination used in vector pGF119 (ompA signal peptide for HC and pelB signal peptide for LC) was selected for continuation.

Vector pGF150 with T7 promoter and signal sequence stII for periplasmic targeting of both heavy chain and light chain of the anti-EGFR1 Fab was transformed to strain BL21 (De3). In comparison to others, it looked at least as good as pelB for light chain and ompA for heavy chain, as used in vector pGF119.

Optimization of the Promoter for Fab Expression

Three different promoters were used in preliminary screenings; IPTG-inducible T5, IPTG-inducible T7 and rhamnose inducible Rham. Promoter sequences originated from commercial vectors pET-15b, pD441 and pD881. Signal peptides ompA for HC and pelB for LC were used. Expression cassettes were constructed in dicistronic manner, internal ribosome binding site taaGGATCCGAATTCAAGGAGATAAAAAatg (SEQ ID NO: 22) between the heavy and the light chain in each vector. Vector codes and promoters are presented in Table 16.

TABLE 16

Optimization of the promoter system for Fab expression; vector codes and promoters used.

| Vector | promoter |
| --- | --- |
| pGF119 | T5 |
| pGF121 | T7 |
| pGF132 | Rham | pGF119 and pGF132 were electroporated to *E. coli* strain W3110 as described above. T7 promoter vector pGF121 was transformed to chemically competent *E. coli* BL21(De3) cells (New England Biolabs) according to heat shock protocol provided by the supplier. Expression cultures, sample preparation and analysis of periplasmic extracts were made as described in above. First comparison was made between the strains W3110 pGF119 and BL21(De3) pGF121. Periplasmic extracts were made in parallel with 10×TE buffer and with 0.05% deoxycholate buffer.

Figure 6:
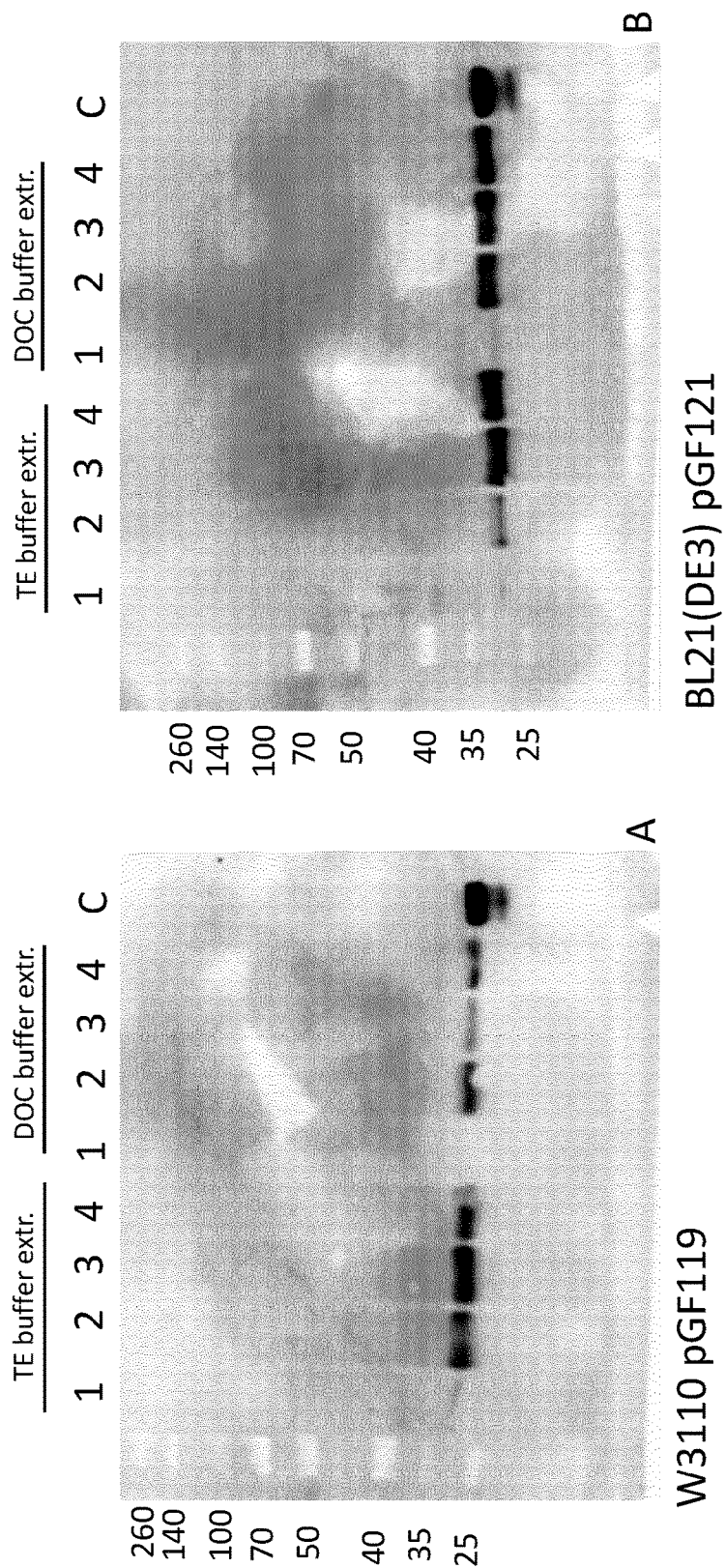
FIG. 6. Results of promoter optimization for Fab expression. 10 ml expression cultures in liquid LB media were made with either W3110 pGF119 (A) or BL21 (De3) pGF121 (B). Post-induction cultures were grown o/n at +20° C., 1 ml samples were harvested and periplasmic extractions followed by western blot detection. 1) background strain w/o the expression vector; 2) W3110 pGF119 clone #1; 3) W3110 pGF119 clone #2 4) W3110 pGF119 clone #3; C) 250 ng of control Fab.

As exemplified in FIG. 6, T7 promoter was slightly better than T5 promoter, although difference was not very notable. Repeated experiments with strains W3110 pGF119 and BL21(De3) pGF121 revealed anyhow that expression cultures with BL21(De3) pGF121 were more stable and repeatable than with W3110 pGF119. Faster growth rates and higher cell densities were achieved with BL21(De3) pGF121 than with W3110 pGF119 (data not shown).

The second step in promoter screening was to analyze the preliminary expression levels from small scale cultures with W3110 pGF132 (rhamnose inducible promoter). One the advantages of rhamnose induced promoter is that the expression level can be fine-tuned by varying the rhamnose concentration. With some proteins of interest, the lower expression level has actually led to higher overall titers because of correct folding and assembly of target protein and higher cell density of production strain. Thereof the induction was made with increasing concentrations of rhamnose in parallel 10 ml liquid LB cultures (0, 0.25 mM, 1 mM, 4 mM and 8 mM). Three different post-induction temperatures were used; +20° C., +28° C. and +37° C. 1 ml samples were harvested at the time point of 4 h post-induction. Sampling, periplasmic extraction and analysis were made as described in example 1.

Figure 7:
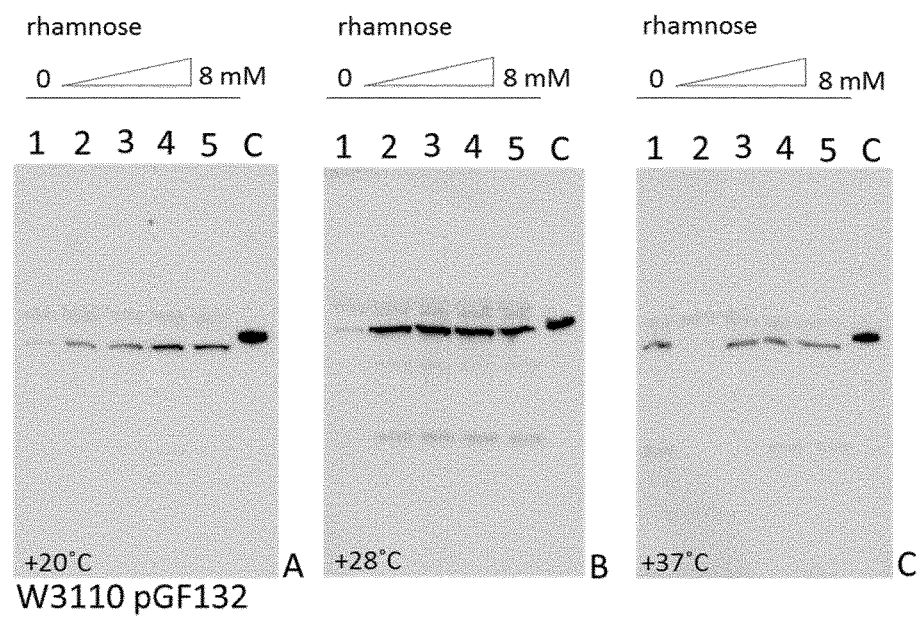
FIG. 7. Results of promoter optimization for Fab expression. 10 ml expression cultures in liquid LB media were made with W3110 pGF132 in three different post-induction temperatures; A)+20° C.; B)+28° C. and C)+37° C. Different rhamnose concentrations were used for induction: 1) rha 0; 2) rha 0.25 mM; 3) rha 1 mM; 4) rha 4 mM; 5) rha 8 mM. C=100 ng of control fab. Post-induction cultures were grown 4 h at indicated temperatures, 1 ml samples were harvested and periplasmic extractions followed by western blot detection were.

As shown in FIG. 7, expression level with rhamnose inducible promoter remained below the level achieved with BL21(De3) pGF121 (T7 promoter). Promoter regulation with increasing concentrations of rhamnose was most functional at +20° C. Anyhow, highest titers with the rhamnose system were achieved at +28° C.

Based on the repeated experiments described above, BL21(De3) and T7 promoter system were selected as a basic platform for production of anti-EGFR1 Fab in *E. coli*.

Codon Optimization of Anti-EGFR1 Fab for Expression in *E. coli* Cells

Three HC/LC sequences with different codon optimization pattern for *E. coli* and one HC/LC sequence originally optimized for CHO cells were tested. Vectors were constructed as described for pGF119, dicistronic manner and T5 promoter driving the expression. Expression host was *E. coli* W3110. Small scale cultures, sampling and analysis of the periplasmic extracts were made as described above. Sequence in vector pGF119 was selected as a baseline level. Codon optimization pattern had a drastic effect on expression level (Table 17). *E. coli* version 2 (pGF128) and CHO cell optimized (pGF126) sequences did not work in W3110 host strain, only traces of Fab was detected from the expression cultures by Western blot. Expression level achieved with *E. coli* version 3 (pGF129) was significantly better, but still similar to baseline levels. Because most of the vectors were already made with *E. coli* version 1 (pGF119) and because no improvements in comparison the baseline were made by changing the codon optimization pattern, the *E. coli* version 1 sequences from vector pGF119 were selected for use (SEQ ID NO: 10 and SEQ ID NO: 11).

TABLE 17

Testing the anti-EGFR1 Fab coding sequences with different codon optimization pattern. Vector coding and results.

| Vector | Codon optimization pattern | Expression level |
| --- | --- | --- |
| pGF119 | *E. coli*, version 1 | baseline |
| pGF128 | *E. coli*, version 2 | low or no expression |
| pGF129 | *E. coli*, version 3 | similar to baseline |
| pGF126 | CHO cell | low or no expression |

Comparing the Discistronic to Dual Promoter Vector Setup

In dicistronic vector setup, the spacer sequence between the heavy and the light chain, including the ribosome binding site, is relatively short, only 25 nucleotides in pGF119. To expand this space between the heavy and the light chain, the vectors pGF120 and pGF131 were constructed, in which both of the chains were expressed under the control of separate T5 or T7 promoters, respectively. Vectors were constructed by utilizing the existing sequences on dicistronic vector pGF121. Once completed, pGF120 was electroporated to strain W3110 and pGF131 transformed to chemically competent BL21(De3) and Lemo21(De3) *E. coli* cells. Small scale expression tests were made as above and comparison was made between dicistronic and dual promoter vectors (pGF119 vs. pGF120; pGF121 vs. pGF131).

Figure 8:
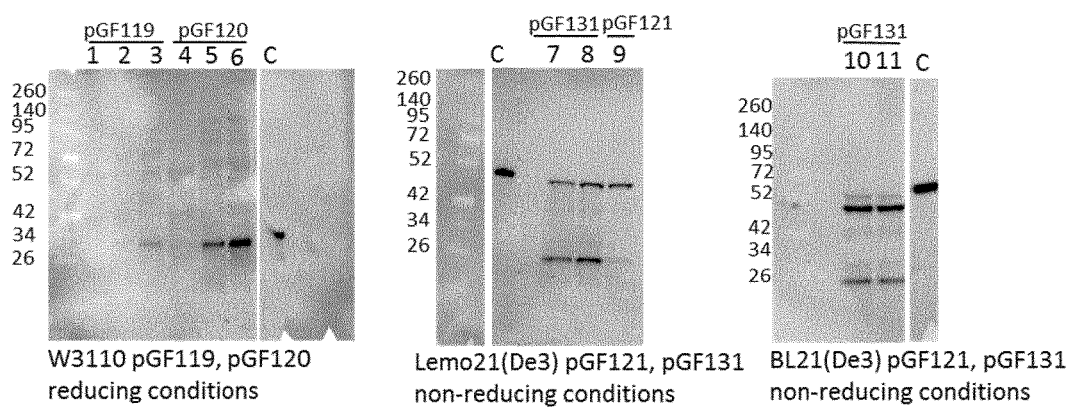
FIG. 8. Comparing the dicistronic to dual promoter setup. pGF119 and pGF121 are dicistronic, pGF120 and pGF131 are dual promoter vectors. 1) non-induced control 2) W3110 pGF119#1 3) W3110 pGF119#2 4) W3110 pGF120 non-induced 5) W3110 pGF120#1 6) W3110 pGF120#2 7) Lemo21(De3) pGF131#1 8) Lemo21(De3) pGF131#2 9) Lemo21(De3) pGF121#1 10) BL21(De3) pGF131#1 11) BL21(De3) pGF131#2 C) 100 ng of control fab.

As demonstrated in FIG. 8, dual T5 promoter was clearly more efficient for anti-EGFR1 Fab production than the dicistronic setup. With T7 promoter, the difference was not as clear, but it was noticed that there was a larger amount of non-assembled Fab chain presented with dual promoter system than with dicistronic setup. The next optimization step planned was to apply chaperon helper plasmids to the expression strain to promote the correct folding and assembly. Dual promoter setup with T7 promoter (vector pGF131) was selected for continuation.

Construction of Chaperon Helper Plasmids

To enhance Fab expression, periplasmic and cytoplasmic chaperones for coexpression with vector pGF131 were selected. As a backbone vector for chaperone helper plasmids, pCDF-1b (Novagen) was selected. pCDF-1b has T7 promoter, lac operator, replication of origin derived from CloDF13 and streptomycin/spectinomycin antibiotic resistance. It is compatible for coexpression with pET vectors, and thereof suitable to be expressed together with pGF133 having pET-15b backbone.

Chaperone sequences were PCR amplified from *E. coli* genomic DNA with PCR and high-fidelity phusion polymerase (Thermo Scientific). Amplified fragments were cloned to pCDF-1b backbone utilizing traditional digestion/ligation cloning and seamless Gibson assembly. Setup of the chaperon helper plasmids is described with more details in tables 18-20. 5-7.

TABLE 18

Cloning strategy of chaperon helper plasmids pGF134, pGF135, pGF137, pGF138.

| vector | description | primers | vector | insert | cloning |
| --- | --- | --- | --- | --- | --- |
| pGF134 | *E. coli* periplasmic chaperone SKP | GP1113 GP1114 | pCDF-1b cut with NcoI/NotI | PCR product cut with NcoI/NotI | Restriction and ligation |

TABLE 18-continued

Cloning strategy of chaperon helper plasmids pGF134, pGF135, pGF137, pGF138.

| vector | description | primers | vector | insert | cloning |
|---|---|---|---|---|---|
| pGF135 | E. coli periplasmic chaperones SKP and FkpA | GP1115 GP1116 | pGF134 cut with XhoI/NotI | PCR product cut with XhoI/NotI | Restriction and ligation |
| pGF137 | E. coli cytoplasmic chaperones DnaK/DnaJ | GP1119 GP1120 | pCDF-1b cut with NcoI/NotI | Uncut PCR product | Gibson assembly |
| pGF138 | E. coli cytoplasmic chaperones DnaK/DnaJ GrpE | GP1147 GP1148 | pGF137 cut with XhoI | Uncut PCR product | Gibson assembly |

TABLE 19

Primer sequences used for construction of chaperone helper plasmids.

| GP1113 | CGGGATCCAAGAAGGAGATATACCATGGCAAAAAAGTGGTT ATTAGCTGC (SEQ ID NO: 23) |
|---|---|
| GP1114 | ATAATGCGGCCGCATTATTTAACCTGTTTCAGTAC (SEQ ID NO: 24) |
| GP1115 | ATAATGCGGCCGCAAGAAAGGAGATATACCATGGCAAAATC ACTGTTTAAAGTAACG (SEQ ID NO: 25) |
| GP1116 | ATAATCTCGAGATTATTTTTTAGCAGAATCTGC (SEQ ID NO: 26) |
| GP1147 | TGACCCGCTAATGCGGCCGCACTGAGTGCTTCCCTTGAAAC CCTGAAACTGATC (SEQ ID NO: 27) |
| GP1148 | GGTTTCTTTACCAGACTCAAACGGCCCGGCATTCGCATGCA GGGCCGTGAATTATTACG (SEQ ID NO: 28) |

TABLE 20

Chaperones used.

| chaperon | uniprot accession number |
|---|---|
| SKP | B7MBF9 |
| FkpA | H9UXM6 |
| DnaK | B7M9S6 |
| DnaJ | C6EB39 |
| GrpE | C8U980 |

Anti-EGFR1 Fab Coexpression with Helper Plasmids

Vector pGF131 was transformed to chemically competent BL21(De3) and Lemo21(De3) cells according to manufacturers instructions. Few clones were picked and expression of anti-EGFR1 Fab was verified by preliminary expression cultures, as described above. The best clones were selected as a background for the coexpression with chaperone helper plasmids.

Electrocompetent BL21(De3) pGF131 and Lemo21(De3) pGF131 cells were constructed as follows. 5 ml preculture was grown o/n in liquid LB supplemented with kanamycin 20 mg/L. On day 2, 1 ml of preculture was re-inoculated to 50 ml of liquid LB with kanamycin 20 mg/L. Culture was continued at +37° C. 220 rpm~3 h, until the $OD_{600}$ reached the level 0.5. Cells were harvested by centrifugation, 10 min 8000×g and resuspended to 10 ml of 10% ice-cold glycerol. Harvesting by centrifugation was repeated, followed by resuspension to 5 ml of 10% ice-cold glycerol. Cells were aliquoted to 10×500 ul aliquotes and stored at −80° C.

Chaperon helper plasmids pGF134 and pGF135 were electroporated to BL21(De3) and Lemo21(De3) strains with BioRad Gene Pulser, program Ec2. Mixture was plated to LB+km+stre after short preculture in +37° C. and plates were cultivated in +37° C. o/n. Preliminary expression cultures were made as above.

Figure 9:
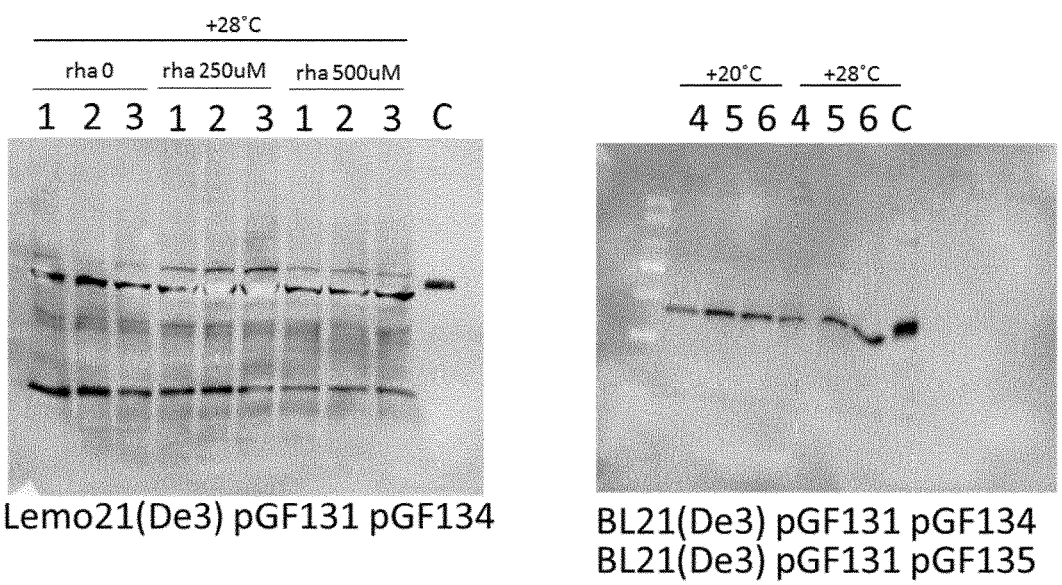
FIG. 9. Anti-EGFR1 Fab expression in *E. coli* Lemo21 (De3) and BL21(De3) with periplasmic chaperones SKP (pGF134) and SKP/FkpA (pGF135). Lemo21(De3) cultures were made utilizing the build-in feature of the strain enabling the fine-tuning with rhamnose. Lane 1) Lemo21 (De3) pGF131 2) Lemo21(De3) pGF131 pGF134 3) Lemo21(De3) pGF131 pGF135 4) BL21(De3) pGF131 5) BL21(De3) pGF131 pGF134 6) BL21(De3) pGF131 pGF135 C) control Fab 100 ng. At +28° C. with 250 uM rhamnose, Lemo21(De3) pGF131 pGF134 and—pGF135 (lanes 2 and 3) produced a clearly increased amount of anti-EGFR1 Fab in comparison to Lemo21(De3) pGF131 (lane 1). On +20° C., BL21(De3) pGF131 pGF134 and—pGF135 (lanes 5 and 6) produced a clearly increased amount of anti-EGFR1 Fab in comparison to BL21(De3) pGF131 (lane 4).

As exemplified in FIG. 9, SKP chaperon has clearly beneficial effect on production, but difference to background strain harboring only the expression plasmid pGF131 was not remarkable. Anyhow, the clones with chaperon helper plasmid tended to grow faster and achieve higher cell densities. Cultures with chaperon helper plasmid pGF134 were also more repeatable and stable. There were no differences between the periplasmic chaperon helper plasmids pGF4134 (SKP chaperon) and pGF135 (SKP and FkpA chaperons). The expression of cytoplasmic chaperons DnaK/J GrpE from helper plasmid pGF138 did not improve further the expression level. Thereof strains Lemo21(De3) pGF131 pGF134 and BL21(De3) pGF131 pGF134 were selected for continuation and for the fermentation process development.

Anti-EGFR Single Chain

Expression vector pGF155 for anti-EGFR1 ScFv with signal sequence ompA (SEQ ID NO: 13) was constructed and PCR amplified with high fidelity polymerase and Gibson assembly to pET-15b backbone. In the construct, the polynucleotides encoding the light chain variable region and the heavy chain variable region were separated by the G4S linker/spacer sequence (SEQ ID NO: 29) encoding the 15-mer linker sequence set forth in SEQ ID NO: 30.

Vector pGF155 is transformed to background strain BL21 (De3) either alone or in combination with chaperon helper plasmids, and expression levels are evaluated based on 10 mL preliminary cultures.

Anti-EGFR1 Fab Production in Fermentor Cultivated E. coli Strain (BL21[DE3]pGF131pGF134); Culture Supplemented with Yeast Extract.

Inoculation

Several (5-8 colonies) E. coli colonies (BL21[DE3] pGF131pGF134) were inoculated from LB agar plate in 5 ml of liquid LB medium supplemented with kanamycin (25 mg/L) and streptomycin (30 mg/L). The inoculum (1st inoculum) was incubated at +37° C., 220 rpm, for 5 hours. 1 ml of 1st inoculum was used to inoculate 100 ml of Inoculum culture medium (below) supplemented with kanamycin (25 mg/L) and streptomycin (30 mg/L) in 500 ml shake flask (2nd inoculum). 2nd inoculum was incubated at +37° C., 220 rpm, <16 hours. 10 ml of 2nd inoculum was transferred in 100 ml of Inoculum culture medium (below) supplemented with kanamycin (25 mg/L) and streptomycin (30 mg/L) in 500 ml shake flask (3rd inoculum). 3rd inoculum was incubated at +37° C., 220 rpm, until $OD_{600}$-2.0 was reached and this inoculum was used to inoculate 900 ml of Fermentor Batch culture medium (below) supplemented with kanamycin (25 mg/L) and streptomycin (30 mg/L) in the fermentor culture vessel (2 l) resulting in 1000 ml final volume and $OD_{600}$ value 0.2.

TABLE 21

Inoculum Culture Medium components (Trace Metal Elements [TME] from FeCl₃ × 6 H₂O to MgSO₄ × 7 H₂O).

| Reagent | Mw (g/mol) | mg/l | c (mmol/l) |
|---|---|---|---|
| Na₂HPO₄ × 2 H₂O | 177.99 | 8600 | 48.317 |
| K₂HPO₄ | 174.2 | 3000 | 17.222 |
| NH₄Cl | 53.49 | 1000 | 18.695 |
| NaCl | 58.44 | 500 | 8.556 |
| FeCl₃ × 6 H₂O | 270.33 | 66 | 0.245 |
| H₃BO₃ | 61.83 | 3 | 0.049 |
| MnCl₂ × 2 H₂O | 161.87 | 12 | 0.076 |
| EDTA × 2 H₂O | 372.24 | 8.4 | 0.023 |
| CuCl₂ × 2 H₂O | 170.48 | 1.5 | 0.009 |
| Na₂MoO₄ × 2 H₂O | 429.89 | 2.5 | 0.006 |
| CoCl₂ × 6 H₂O | 237.93 | 2.5 | 0.011 |
| ZnSO₄ × 7 H₂O | 287.54 | 10 | 0.036 |
| Glucose | 180.16 | 10000 | 55.506 |
| MgSO₄ × 7 H₂O | 246.47 | 600 | 2.434 |

TABLE 22

Fermentor Batch Culture Medium (Trace Metal Elements [TME] from FeCl₃ × 6 H₂O to MgSO₄ × 7 H₂O).

| Reagent | Mw (g/mol) | mg/l | c (mmol/l) |
|---|---|---|---|
| K₂HPO₄ | 174.2 | 16600 | 95.293 |
| (NH₄)₂HPO₄ | 132.07 | 4000 | 30.287 |
| Citric acid × 1 H₂O | 210.14 | 2297 | 10.931 |
| FeCl₃ × 6 H₂O | 270.33 | 83 | 0.306 |
| H₃BO₃ | 61.83 | 3.8 | 0.061 |
| MnCl₂ × 2 H₂O | 161.87 | 15 | 0.095 |
| EDTA × 2H₂O | 372.24 | 10.5 | 0.028 |
| CuCl₂ × 2 H₂O | 170.48 | 1.9 | 0.011 |
| Na₂MoO₄ × 2 H₂O | 429.89 | 3.1 | 0.007 |
| CoCl₂ × 6 H₂O | 237.93 | 3.1 | 0.013 |
| ZnSO₄ × 7 H₂O | 287.54 | 13 | 0.046 |
| Glucose | 180.16 | 25000 | 138.766 |
| MgSO₄ × 7 H₂O | 246.47 | 1500 | 6.086 |

Fermentation Batch Phase

After inoculating the fermentor culture vessel, the following parameters were set using Biostat®B Plus Digital Control Unit:
temperature+37° C.
pH 6.8 (12.5% NH3, 15% H3PO4)
pO2 (cascade mode)>25%
 Stirring rate 15%-75% (=300 rpm-1500 rpm)
 Gas flow (air) 13%-50% (=0.4 L-1.5 L)

At time point ~8.5 h of fermentation batch phase, DOT (Dissolved Oxygen Tension) value peaked sharply resulting in decreased stirring speed and gas flow. This indicated exhaustion of glucose present in batch culture medium (25 g/l) and the end of fermentation batch phase. $OD_{600}$ value 31 was reached during fermentation batch phase.

Fermentation Fed-Batch Phase

FS (Feed Solution) 1.1 (67% Glc, 2% MgSO₄) was pumped into the fermentor culture vessel for 6 h 20 min, 0.24 mL/min. During this FS 1.1 fed-batch phase OD600 value 70 was reached.

FS 1.2 (50% Glc, 1.5% MgSO₄, 7.4 g/100 mL Yeast Extract, 15-fold TME [Trace Metal Elements] concentration compared to Fermentor Batch culture medium, 0.32 g/L Thiamine) was pumped into the fermentor culture vessel for 7 h, 0.24 mL/min. $OD_{600}$ value 134 was reached. At this point the pumping speed was reduced to 0.13 mL/min for 11 h 40 min. $OD_{600}$ value did not increase from 134. Also another fermentor run was performed without supplemented yeast extract and this fermentor run resulted about 20 mg/L of anti-EGFR1 Fab as estimated with Western blotting analysis as below.

During the fed-batch phase glucose concentration in the culture suspension was followed using Keto-diabur-test 5000 sticks (Roche, Cat #: 10647705187) according to manufacturer's instructions.

Induction of Protein Synthesis

Prior to IPTG induction of protein synthesis, cultivation temperature was decreased from +37° C. to +20° C. IPTG induction of protein synthesis (final IPTG concentration 1 mM) was carried out at OD600 value 86. Induction on protein synthesis was carried out for 16 hours.

Collecting the Samples During the Fermentation Round

Samples for Western blot analysis (2×1 mL pellet sample and 2×1 mL supernatant sample) were collected at different time points. Pre-induction samples were taken just before IPTG induction of protein synthesis. Another set of samples was collected at 4 hours' induction time point. The last set of samples was collected at 16 hours' induction time point prior to culture harvest. Cells were pelleted in the samples (+4° C., 5000×g, 15 min) and supernatants were transferred in new tubes. Samples were stored at −20° C. until analyzed using Western Blot method.

Cell Harvest

The fermentation culture suspension was collected in SLA 3000 centrifuge tubes (Sorvall RC6) using Watson Marlow 504U 056.3762.00 pump, and the centrifuge tubes were balanced. Cells were pelleted (+4° C., 5000×g, 60 min) and the supernatant was discarded. Cell pellets were stored at −20° C.

Western Blot Analysis of Periplasmically Expressed Anti-EGFR1 Fab

Pellet samples representing 1 mL of fermentation culture suspension were resuspended in 1 mL of 10×TE pH 7.5 (100 mM Tris-HCl, 10 mM EDTA). Samples were vortexed vigorously for 2 h at r/t, pelleted at +4° C., 12 000×g, 60 min and supernatants were collected as periplasmic extracts.

Periplasmic extracts were further analyzed with Western blotting. 100 µL of extract was mixed with 25 µL of non-reducing loading buffer. 12.5 µL of mix was loaded into 4-20% Precise Tris-Glycine SDS-Page gel (Thermo Scientific). Gel was run in 1× Laemmli running buffer 200 V~45 min and blotted to nitrocellulose membrane in Tris-Glycine blotting buffer, 350 mA~1.5 hours. BioRad Mini-protean system was used for SDS-Page and blotting. Blotted membrane was blocked with 1% BSA in PBS. Detection was made with anti-human IgG (Fab specific) with peroxidase conjugate (Sigma Aldrich; cat no A0293) and Luminata Forte Western HRP substrate (Millipore; cat no WBLUF0500). Chemiluminescense reaction was detected with Fujifilm Luminescent Image Analyzer LAS4000.

Figure 10:
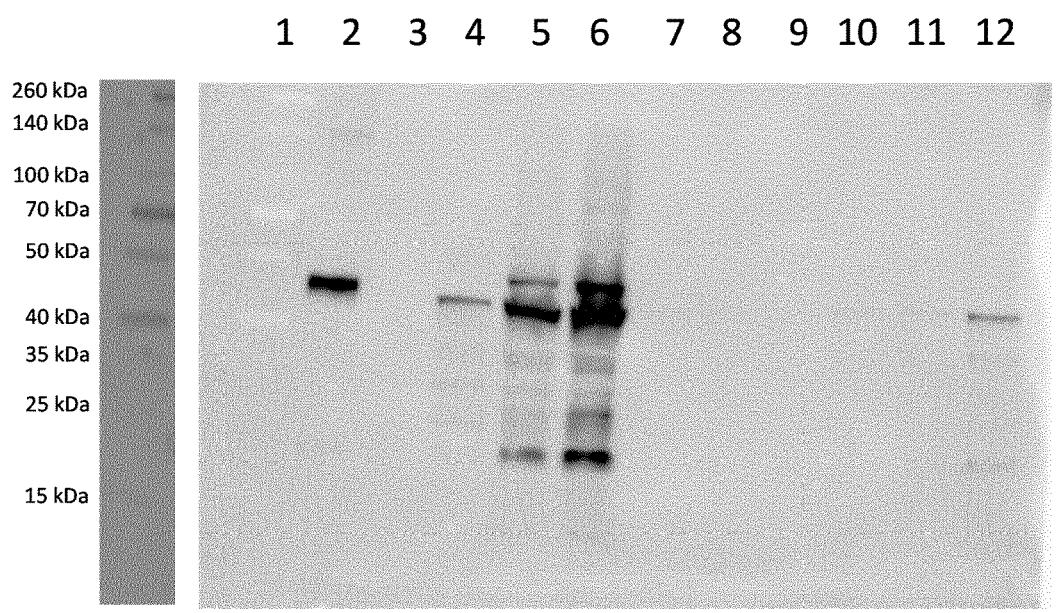
FIG. 10. Western Blot analysis of periplasmically expressed anti-EGFR1 Fab. Lane 1) Molecular Weight Marker; Lane 2) anti-EGFR1 Fab control protein, 100 ng; Lane 3) Empty; Lane 4) Pre-induction cell pellet sample; Lane 5) 4 hours post-induction cell pellet sample; Lane 6) 16 hours post-induction cell pellet sample; Lanes 7-9) Empty; Lane 10) Pre-induction culture supernatant sample; Lane 11) 4 hours post-induction culture supernatant sample; Lane 12) 16 hours post-induction culture supernatant sample. All samples represented 10 μl of fermentor culture suspension. Anti-EGFR1 Fab concentration in periplasmic extract of fermentor cultivated *E. coli* cells was estimated comparing band intensities in 16 hours post-induction cell pellet sample (Lane 6) to band intensity of control anti-EGR1 Fab in lane 2 (100 ng). Lane 6 was estimated to contain 300 ng of anti-EGR1 Fab: 300 ng/10 μl=30 mg/L.

10 µL of each culture supernatant sample was mixed with 2.5 µL of non-reducing loading buffer and these samples were run in SDS-PAGE gel and blotted on nitrocellulose membrane as described above for periplasmic extract samples. The results are shown in FIG. 10.

Fab Purification

Figure 11:
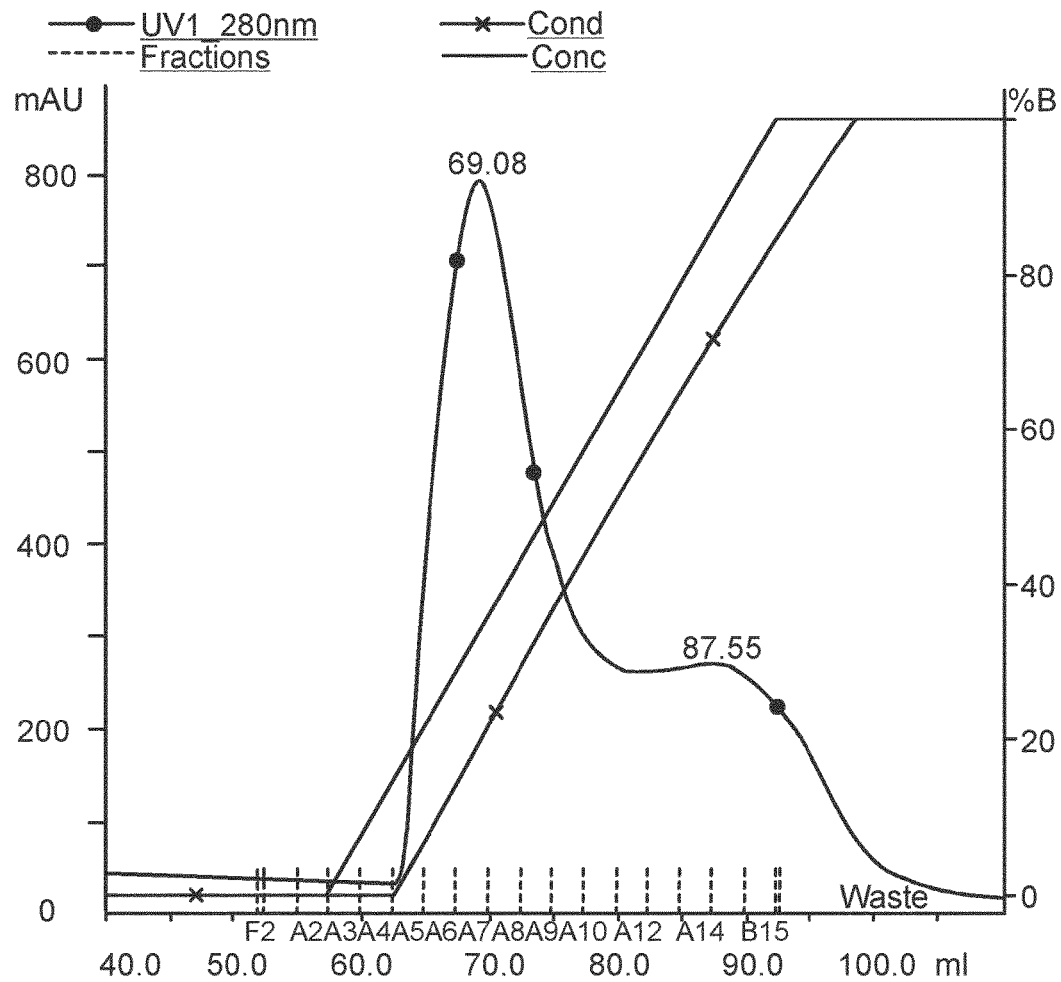
FIG. 11. Chromatogram of HiTrap SP FF purified periplasmic extract. Fractions A5-A10 were pooled for further purification steps.

The buffer of filtered periplasmic extract was exchanged to 50 mM MES pH 6 using Amicon Ultra 10K centrifugal filter prior to first purification step by 5 ml cation exchange column (HiTrap SP FF, GE Healthcare). Mobile phase A was 50 mM MES pH 6 and mobile phase B was 50 mM MES pH 6+500 mM NaCl. The sample was filtered through 1.2 µm membrane prior the run. First, 10% sample was injected to the column at a flow-rate of 2.5 ml/min for 5 mins, after which flow-rate was changed to 5 ml/min. The column was run with 57.5 ml of phase A, and then a linear gradient from 0% B to 100% B over 35 ml was applied. 2.5 mL fractions were collected and fractions A5-A9 were pooled. The rest of the sample was run in two separate runs as described above and fractions A5-A10 were pooled (FIG. 11). Papain digested anti-EGFR1 Fab was used as a control.

Figure 12:
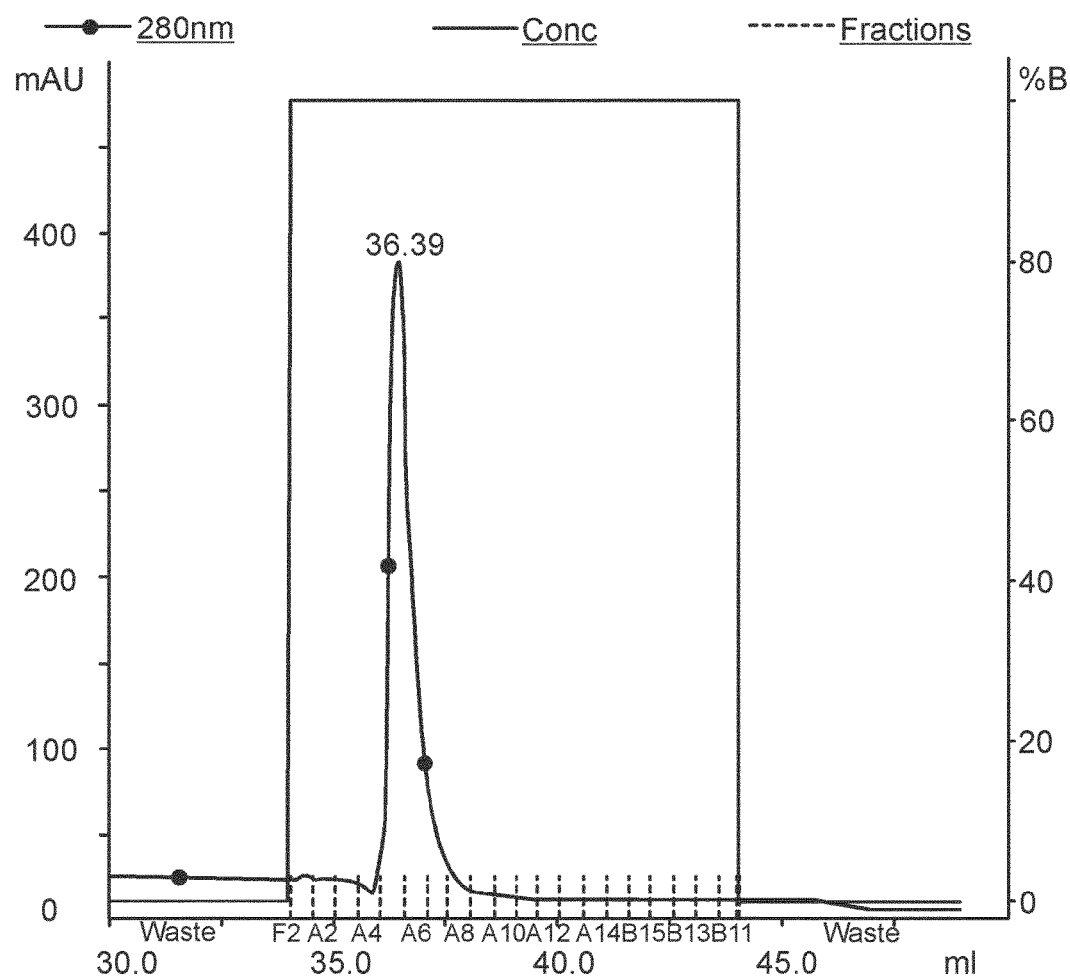
FIG. 12. Chromatogram of Protein L purified sample. Fractions A5-A7 were pooled.

The pooled fractions (A5-A10) were injected on Protein L column (1 ml) without changing the buffer. Protein L was run at flow-rate of 0.2 ml/min during sample injection and 1 mL/min during wash and elution. Mobile phase A was PBS and B 0.1 M Na-citrate pH 3. The sample was eluted with 100% B. The protein eluted with a sharp peak (FIG. 12) and fractions A5-A7 were pooled and neutralized with 2 M Tris-HCl pH 9. After the two purification steps the yield of the Fab was estimated to be about 44 mg/L. Another batch was subjected for Protein L purification only and this yielded about 72 mg/L of the Fab fraction. Papain digested anti-EGFR1 Fab was used as a control.

Figure 13:
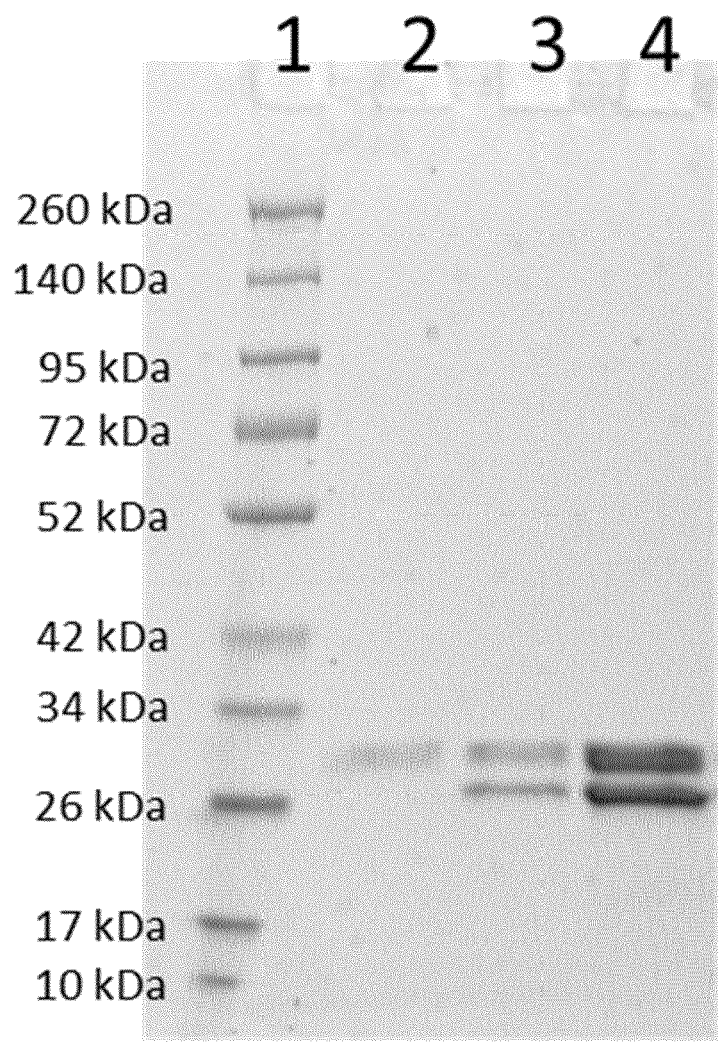
FIG. 13. SDS-PAGE analysis of purified anti-EGFR1 Fab. The samples were loaded in equal amounts (24 μL). Lane 1) Molecular Weight Marker; Lane 2) papain digestion derived anti-EGFR1 Fab; Lane 3) 10% sample of *E. coli* produced Fab; Lane 4) 40% sample of *E. coli* produced Fab. In lanes 3 and 4 LC (upper) and HC (lower) bands have been separated. In lane 2 the Fab is glycosylated and LC and HC cannot be separated.

The pooled fractions were analyzed in SDS-PAGE. 24 μL of each of these three pooled samples from chromatographic runs with Protein L column were mixed with 6 μL reducing loading buffer and run in SDS-PAGE gel. The gel was stained with a Coomassie based stain (FIG. 13).

Example 14. Binding of Anti-EGFR1 Fab and Anti-EGFR1 Fab BSH-Dextran to EGFR1

Protein A purified CHO cell produced anti-EGFR1 was papain digested, purified with NAb Protein A Plus Spin columns and treated with recombinant Endo F2 (*Elizabethkingia meningosepticum* (produced in *E. coli*, Calbiochem) which cleaves biantennary oligosaccharides and high mannoses leaving one GlcNAc unit to asparagine so that non-glycosylated Fab fragments were obtained. 100 mU of the enzyme was added to approx. 1 mg of anti-EGFR1 Fab and incubated o/n at +37° C. in 50 mM NaAc pH 4.5.

100 μg of anti-EGFR1 Fab and 100 μg of anti-EGFR1 Fab BSH-dextran were Cy3-labeled using Amersham Cy3 mono-reactive according to manufacturer instructions and 0.5 mg/ml solutions were prepared in citrate/phosphate buffer pH 7 to be used for microarray printing.

Array of six different molecules (HER2, human EGFR1, CD64, CD16a, HSA and anti-Dextran IgG) was printed on amine reactive N-hydroxysuccinimide (NHS)-activated microarray slides (four parallel spots for each molecule). Cy3-labeled anti-EGFR1 Fab BSH-dextran conjugate and anti-EGFR1 Fab were incubated on separate wells of the slide in eight concentrations ranging from 0.4 nM to ~900 nM. Non-specific binding was removed using 10× non-conjugated BSH dextran. After washing of the slide fluorescence signal was detected using a laser scanner. Average intensities and standard deviations for each concentration point were calculated from four parallel datapoints. $K_d$ values were determined by fitting the data to Langmuir isotherm:

$$F=(F_{max}[p])/([p]+K_d)$$

where F=fluorescence intensity, $F_{max}$=maximum intensity at saturation, [p]=concentration of Cy3 labeled molecule and $K_d$=dissociation constant.

Figure 14:
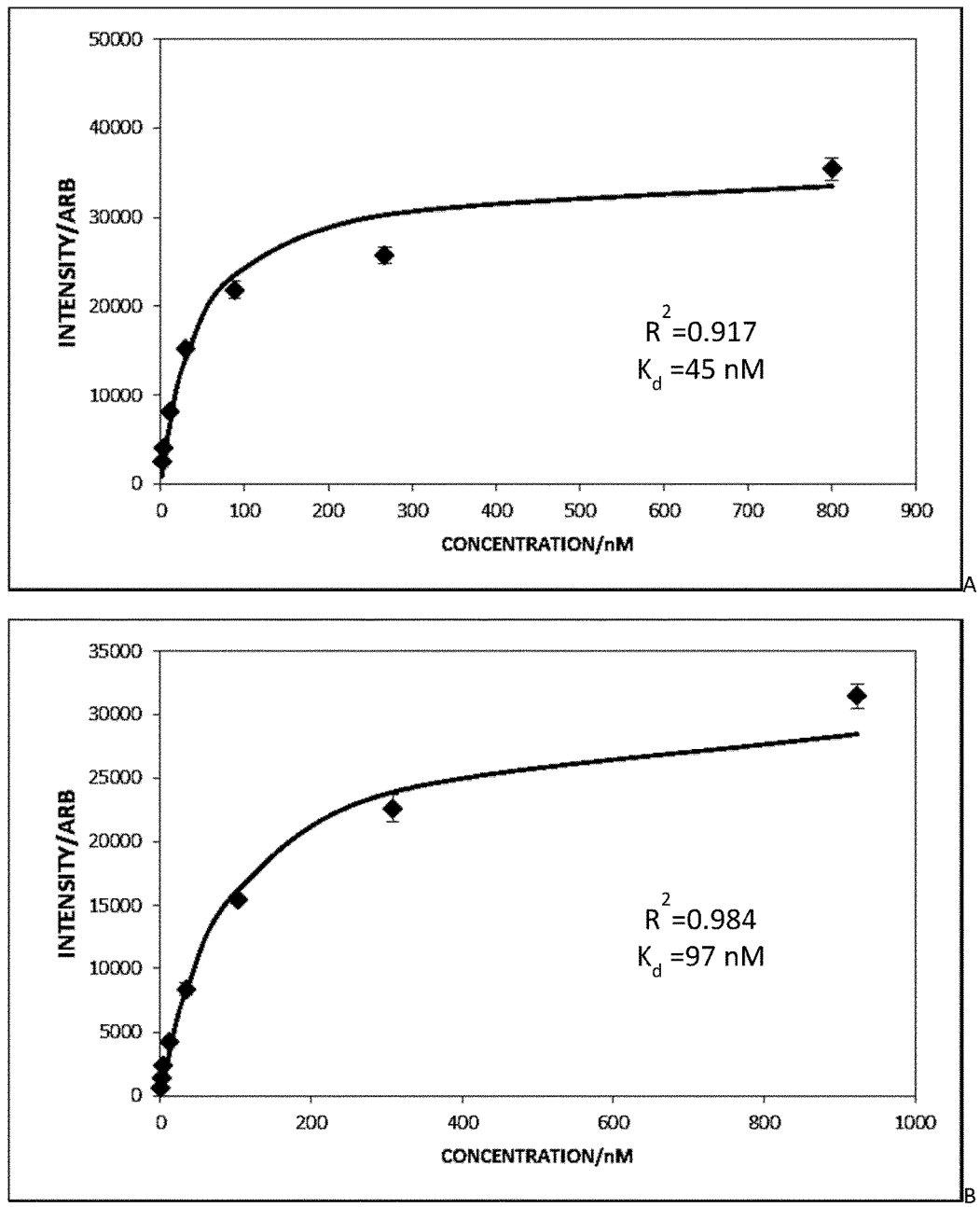
FIG. 14. Binding of anti-EGFR1 Fab (upper panel) or Fab BSH-dextran (lower panel) to EGFR1 on microarray slide.

Anti-EGFR1 Fab BSH-dextran conjugate bound to EGFR1 with a dissociation constant about $K_d$=97 nM. The unconjugated Fab has about 2 fold higher affinity compared with the anti-EGFR1 Fab BSH dextran to EGFR1 (FIG. 14). Anti-EGFR1 Fab BSH-dextran or unconjugated Fab binding to HER2, CD64, CD16a, HSA or anti-dextran IgG were below detection limits.

It is obvious to a person skilled in the art that with the advancement of technology, the basic idea of the invention may be implemented in various ways. The invention and its embodiments are thus not limited to the examples described above, instead they may vary within the scope of the claims.

The invention claimed is:

1. A conjugate comprising an anti-EGFR1 antibody, or a Fab or F(ab')$_2$ fragment thereof, and at least one dextran derivative, wherein the dextran derivative comprises at least one D-glucopyranosyl unit comprising at least one carbon selected from carbon 2, 3 or 4 thereof comprising:

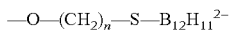

$$-O-(CH_2)_n-S-B_{12}H_{11}{}^{2-}$$

wherein n is in the range of 3 to 10;

the dextran derivative is bound to the anti-EGFR1 antibody or a Fab or F(ab')$_2$ fragment thereof via a bond formed by a reaction between at least one aldehyde group of a D-glucopyranosyl unit of the dextran derivative and a lysine of the anti-EGFR1 antibody or Fab or F(ab')$_2$ fragment thereof;

the anti-EGFR1 antibody or Fab or F(ab')$_2$ fragment thereof binds EGFR1, is internalized by a cell expressing EGFR1; and, the anti-EGFR1 antibody or Fab or F(ab')$_2$ fragment comprises:

the amino acid sequence of SEQ ID NO: 2 and SEQ ID NO:3;

the amino acid sequence of SEQ ID NO: 3 and SEQ ID NO: 6;

the amino acid sequence of SEQ ID NO: 3 and SEQ ID NO: 7;

the amino acid sequence of SEQ ID NOS: 4 and SEQ ID NO: 5;

the amino acid sequence of SEQ ID NO: 14;

the amino acid sequence of SEQ ID NO: 15;

a light chain variable region encoded by polynucleotide at least 90% identical to SEQ ID NO: 8 and a heavy chain variable region encoded by polynucleotide at least 90% identical to SEQ ID NO: 9;

a light chain encoded by polynucleotide at least 90% identical to SEQ ID NO: 10 and a heavy chain encoded by polynucleotide at least 90% identical to SEQ ID NO: 11;

an amino acid sequence encoded by a polynucleotide at least 90% identical to SEQ ID NO:12; or, an amino acid sequence encoded a polynucleotide at least 90% identical to SEQ ID NO:13;

wherein said conjugate is produced by:

a) combining X—(CH$_2$)$_m$CH=CH$_2$ wherein m is in the range from 1 to 8, and X is Br, Cl, or I, and dextran comprising multiple D-glucopyranosyl units, to produce allylated dextran comprising —OCH$_2$CH=CH$_2$ at C2, C3 or C4 of at least one of said D-glucopyranosyl units, said allylated dextran further comprising unmodified D-glucopyranosyl units;

b) reacting B$_{12}$H$_{11}$SH, and said allylated dextran in the presence of a radical initiator selected from the group consisting of ammonium persulfate, potassium persulfate, or UV light to produce borocaptate dextran (BSH-dextran) comprising —O(CH$_2$)$_n$—S—B$_{12}$H$_{11}$ at said C2, C3 or C4 of said at least one D-glucopyranosyl unit;

c) oxidizing said BSH-dextran using an oxidizing agent selected from the group consisting of sodium periodate, periodic acid, and lead(IV) acetate to produce oxidatively cleaved BSH-dextran comprising free aldehydes on at least one of said unmodified D-glucopyranosyl units; and, d) producing a conjugate of said oxidatively cleaved BSH-dextran and said anti-EGFR1 antibody Fab or F(ab')$_2$ fragment by reacting at least one of said free aldehydes of said oxidatively cleaved BSH-dextran with at least one lysine of the anti-EGFR1 antibody or Fab or F(ab')$_2$ fragment;

and, wherein unreacted aldehyde groups of the oxidatively cleaved BSH-dextran obtained from step c) or a conjugate obtained from step d) are capped using a hydrophilic capping agent.

2. The conjugate according to claim 1, wherein the dextran derivative has a molecular mass in the range of about 3 to about 2000 kDa, or about 30 to about 300 kDa.

3. The conjugate according to claim 1, wherein the conjugate comprises about 10 to about 300 substituents or about 20 to about 150 substituents of the formula —O—(CH$_2$)$_n$—S—B$_{12}$H$_{11}{}^{2-}$.

4. The conjugate according to claim 1, wherein the conjugate further comprises at least one tracking molecule bound to the dextran derivative or to the anti-EGFR1 antibody or the fragment of the anti-EGFR1 antibody.

5. The conjugate according to claim 1, wherein the dextran derivative comprises at least one aldehyde group which is capped.

6. The conjugate according to claim 5, wherein essentially all of the aldehyde groups of one or more D-glucopyranosyl units of the dextran derivative are capped.

7. The conjugate according to claim 1, wherein the method further comprises the step of reacting the oxidatively cleaved BSH-dextran obtained from step c) or the conjugate obtained from step d) with a tracking molecule.

8. The conjugate according to claim 1, wherein the method further comprises capping unreacted aldehyde groups of the oxidatively cleaved BSH-dextran obtained from step c) or the conjugate obtained from step d).

9. The conjugate according to claim 8, wherein the hydrophilic capping agent is selected from the group consisting of ethanolamine, lysine, glycine, and Tris.

10. The conjugate according to claim 1, wherein the oxidatively cleaved BSH-dextran is reacted with the anti-EGFR1 antibody or the Fab or F(ab')$_2$ fragment of the anti-EGFR1 antibody by incubating the oxidatively cleaved BSH-dextran and the anti-EGFR1 antibody or the Fab or F(ab')$_2$ fragment of the anti-EGFR1 antibody at room temperature in an aqueous phosphate buffer having a pH of about 6 to 8 in step d).

11. A pharmaceutical composition comprising the conjugate according to claim 1.

12. A method of treating or modulating the growth of EGFR1 expressing tumor cells in a human, wherein the pharmaceutical composition according to claim 11 is administered to a human in an effective amount.

13. The method of claim 12, wherein the pharmaceutical composition is administered intra-tumorally and/or intravenously.

14. The method according to claim 12, wherein the concentration of boron is analysed in tumor cells and in blood after administering the conjugate or the pharmaceutical composition, and the ratio of the concentration of boron in tumor cells to the concentration of boron in blood is higher than 1:1, 2:1, 3:1, 4:1, 5:1, 6:1, 7:18:1, 10:1, 13:1, 130:1 or 240:1.

* * * * *

SEQUENCE LISTING

```
<160> NUMBER OF SEQ ID NOS: 30

<210> SEQ ID NO 1
<211> LENGTH: 1210
<212> TYPE: PRT
<213> ORGANISM: Homo sapiens
<220> FEATURE:
<223> OTHER INFORMATION: EGF receptor, human NP_005219.2

<400> SEQUENCE: 1

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
```

```
              115                 120                 125
Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
    210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
    290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
        355                 360                 365

Leu His Ile Leu Pro Val Ala Phe Arg Gly Asp Ser Phe Thr His Thr
    370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
        435                 440                 445

Gly Leu Arg Ser Leu Lys Glu Ile Ser Asp Gly Asp Val Ile Ile Ser
    450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
        515                 520                 525

Val Ser Arg Gly Arg Glu Cys Val Asp Lys Cys Asn Leu Leu Glu Gly
    530                 535                 540
```

```
Glu Pro Arg Glu Phe Val Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
        595                 600                 605

Lys Tyr Ala Asp Ala Gly His Val Cys His Leu Cys His Pro Asn Cys
    610                 615                 620

Thr Tyr Gly Cys Thr Gly Pro Gly Leu Glu Gly Cys Pro Thr Asn Gly
625                 630                 635                 640

Pro Lys Ile Pro Ser Ile Ala Thr Gly Met Val Gly Ala Leu Leu Leu
                645                 650                 655

Leu Leu Val Val Ala Leu Gly Ile Gly Leu Phe Met Arg Arg Arg His
            660                 665                 670

Ile Val Arg Lys Arg Thr Leu Arg Arg Leu Leu Gln Glu Arg Glu Leu
        675                 680                 685

Val Glu Pro Leu Thr Pro Ser Gly Glu Ala Pro Asn Gln Ala Leu Leu
    690                 695                 700

Arg Ile Leu Lys Glu Thr Glu Phe Lys Lys Ile Lys Val Leu Gly Ser
705                 710                 715                 720

Gly Ala Phe Gly Thr Val Tyr Lys Gly Leu Trp Ile Pro Glu Gly Glu
                725                 730                 735

Lys Val Lys Ile Pro Val Ala Ile Lys Glu Leu Arg Glu Ala Thr Ser
            740                 745                 750

Pro Lys Ala Asn Lys Glu Ile Leu Asp Glu Ala Tyr Val Met Ala Ser
        755                 760                 765

Val Asp Asn Pro His Val Cys Arg Leu Leu Gly Ile Cys Leu Thr Ser
    770                 775                 780

Thr Val Gln Leu Ile Thr Gln Leu Met Pro Phe Gly Cys Leu Leu Asp
785                 790                 795                 800

Tyr Val Arg Glu His Lys Asp Asn Ile Gly Ser Gln Tyr Leu Leu Asn
                805                 810                 815

Trp Cys Val Gln Ile Ala Lys Gly Met Asn Tyr Leu Glu Asp Arg Arg
            820                 825                 830

Leu Val His Arg Asp Leu Ala Ala Arg Asn Val Leu Val Lys Thr Pro
        835                 840                 845

Gln His Val Lys Ile Thr Asp Phe Gly Leu Ala Lys Leu Leu Gly Ala
    850                 855                 860

Glu Glu Lys Glu Tyr His Ala Glu Gly Gly Lys Val Pro Ile Lys Trp
865                 870                 875                 880

Met Ala Leu Glu Ser Ile Leu His Arg Ile Tyr Thr His Gln Ser Asp
                885                 890                 895

Val Trp Ser Tyr Gly Val Thr Val Trp Glu Leu Met Thr Phe Gly Ser
            900                 905                 910

Lys Pro Tyr Asp Gly Ile Pro Ala Ser Glu Ile Ser Ser Ile Leu Glu
        915                 920                 925

Lys Gly Glu Arg Leu Pro Gln Pro Pro Ile Cys Thr Ile Asp Val Tyr
    930                 935                 940

Met Ile Met Val Lys Cys Trp Met Ile Asp Ala Asp Ser Arg Pro Lys
945                 950                 955                 960
```

Phe Arg Glu Leu Ile Ile Glu Phe Ser Lys Met Ala Arg Asp Pro Gln
965                     970                     975

Arg Tyr Leu Val Ile Gln Gly Asp Glu Arg Met His Leu Pro Ser Pro
        980                     985                     990

Thr Asp Ser Asn Phe Tyr Arg Ala Leu Met Asp Glu Glu Asp Met Asp
        995                     1000                    1005

Asp Val Val Asp Ala Asp Glu Tyr Leu Ile Pro Gln Gln Gly Phe Phe
1010                    1015                    1020

Ser Ser Pro Ser Thr Ser Arg Thr Pro Leu Leu Ser Ser Leu Ser Ala
1025                    1030                    1035                    1040

Thr Ser Asn Asn Ser Thr Val Ala Cys Ile Asp Arg Asn Gly Leu Gln
            1045                    1050                    1055

Ser Cys Pro Ile Lys Glu Asp Ser Phe Leu Gln Arg Tyr Ser Ser Asp
            1060                    1065                    1070

Pro Thr Gly Ala Leu Thr Glu Asp Ser Ile Asp Asp Thr Phe Leu Pro
            1075                    1080                    1085

Val Pro Glu Tyr Ile Asn Gln Ser Val Pro Lys Arg Pro Ala Gly Ser
            1090                    1095                    1100

Val Gln Asn Pro Val Tyr His Asn Gln Pro Leu Asn Pro Ala Pro Ser
1105                    1110                    1115                    1120

Arg Asp Pro His Tyr Gln Asp Pro His Ser Thr Ala Val Gly Asn Pro
            1125                    1130                    1135

Glu Tyr Leu Asn Thr Val Gln Pro Thr Cys Val Asn Ser Thr Phe Asp
            1140                    1145                    1150

Ser Pro Ala His Trp Ala Gln Lys Gly Ser His Gln Ile Ser Leu Asp
            1155                    1160                    1165

Asn Pro Asp Tyr Gln Gln Asp Phe Phe Pro Lys Glu Ala Lys Pro Asn
            1170                    1175                    1180

Gly Ile Phe Lys Gly Ser Thr Ala Glu Asn Ala Glu Tyr Leu Arg Val
1185                    1190                    1195                    1200

Ala Pro Gln Ser Ser Glu Phe Ile Gly Ala
            1205                    1210

<210> SEQ ID NO 2
<211> LENGTH: 449
<212> TYPE: PRT
<213> ORGANISM: Artificial Sequence
<220> FEATURE:
<223> OTHER INFORMATION: heavy chain, cetuximab, INN7906H, from IMGT

<400> SEQUENCE: 2

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

```
Thr Leu Val Thr Val Ser Ala Ala Ser Thr Lys Gly Pro Ser Val Phe
            115                 120                 125

Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Arg Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 3
<211> LENGTH: 214
<212> TYPE: PRT
<213> ORGANISM: Artificial Sequence
<220> FEATURE:
<223> OTHER INFORMATION: Light chain, cetuximab, INN7906L, from IMGT

<400> SEQUENCE: 3

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
```

```
                    20                  25                  30
Ile His Trp Tyr Gln Gln Arg Thr Asn Gly Ser Pro Arg Leu Leu Ile
            35                  40                  45

Lys Tyr Ala Ser Glu Ser Ile Ser Gly Ile Pro Ser Arg Phe Ser Gly
 50                  55                  60

Ser Gly Ser Gly Thr Asp Phe Thr Leu Ser Ile Asn Ser Val Glu Ser
 65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 4
<211> LENGTH: 453
<212> TYPE: PRT
<213> ORGANISM: Artificial Sequence
<220> FEATURE:
<223> OTHER INFORMATION: nimotuzumab_HC

<400> SEQUENCE: 4

Gln Val Gln Leu Gln Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
            20                  25                  30

Tyr Ile Tyr Trp Val Arg Gln Ala Pro Gly Gln Gly Leu Glu Trp Ile
        35                  40                  45

Gly Gly Ile Asn Pro Thr Ser Gly Gly Ser Asn Phe Asn Glu Lys Phe
    50                  55                  60

Lys Thr Arg Val Thr Ile Thr Val Asp Glu Ser Thr Asn Thr Ala Tyr
65                  70                  75                  80

Met Glu Leu Ser Ser Leu Arg Ser Glu Asp Thr Ala Phe Tyr Phe Cys
                85                  90                  95

Ala Arg Gln Gly Leu Trp Phe Asp Ser Asp Gly Arg Gly Phe Asp Phe
            100                 105                 110

Trp Gly Gln Gly Ser Thr Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
```

```
                165                 170                 175
Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 5
<211> LENGTH: 219
<212> TYPE: PRT
<213> ORGANISM: Artificial Sequence
<220> FEATURE:
<223> OTHER INFORMATION: nimotuzumab_LC

<400> SEQUENCE: 5

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Asn Ile Val His Ser
            20                  25                  30

Asn Gly Asn Thr Tyr Leu Asp Trp Tyr Gln Gln Thr Pro Gly Lys Ala
        35                  40                  45

Pro Lys Leu Leu Ile Tyr Lys Val Ser Asn Arg Phe Ser Gly Val Pro
    50                  55                  60

Ser Arg Phe Ser Gly Ser Gly Ser Gly Thr Asp Phe Thr Phe Thr Ile
```

```
                65                  70                  75                  80
Ser Ser Leu Gln Pro Glu Asp Ile Ala Thr Tyr Tyr Cys Phe Gln Tyr
                    85                  90                  95

Ser His Val Pro Trp Thr Phe Gly Gln Gly Thr Lys Leu Gln Ile Thr
                    100                 105                 110

Arg Glu Val Ala Ala Pro Ser Val Phe Ile Phe Pro Pro Ser Asp Glu
                    115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                    165                 170                 175

Thr Tyr Ser Leu Ser Ser Thr Leu Thr Leu Ser Lys Ala Asp Tyr Glu
                    180                 185                 190

Lys His Lys Val Tyr Ala Cys Glu Val Thr His Gln Gly Leu Ser Ser
                    195                 200                 205

Pro Val Thr Lys Ser Phe Asn Arg Gly Glu Cys
        210                 215
```

<210> SEQ ID NO 6
<211> LENGTH: 226
<212> TYPE: PRT
<213> ORGANISM: Artificial Sequence
<220> FEATURE:
<223> OTHER INFORMATION: Heavy chain Fab

<400> SEQUENCE: 6

```
Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
                20                  25                  30

Gly Val His Trp Val Arg Gln Ser Pro Gly Lys Gly Leu Glu Trp Leu
            35                  40                  45

Gly Val Ile Trp Ser Gly Gly Asn Thr Asp Tyr Asn Thr Pro Phe Thr
        50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
                100                 105                 110

Thr Leu Val Thr Val Ser Ala Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Lys Arg Val Glu Pro Lys Ser Cys Asp Lys
```

Thr His
225

<210> SEQ ID NO 7
<211> LENGTH: 238
<212> TYPE: PRT
<213> ORGANISM: Artificial Sequence
<220> FEATURE:
<223> OTHER INFORMATION: Heavy chain F(ab')2

<400> SEQUENCE: 7

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly
225                 230                 235

<210> SEQ ID NO 8
<211> LENGTH: 324
<212> TYPE: DNA
<213> ORGANISM: Artificial Sequence
<220> FEATURE:
<223> OTHER INFORMATION: anti-EGFR1_LC_variable_DNA

<400> SEQUENCE: 8
gatattctgc tgacccagtc accggttatt ctgagcgtta gtccgggtga acgtgttagc      60
tttagctgtc gtgcaagcca gagcattggc accaatattc attggtatca gcagcgtacc     120
aatggtagtc cgcgtctgct gatcaaatat gcaagcgaaa gcattagcgg tattccgagc     180
cgttttagcg gttctggtag cggcaccgat tttacccctg agtattaatag cgttgaaagc    240 gaagatatcg ccgattatta ctgccagcaa aataacaatt ggccgaccac ctttggtgca     300

```
ggtacaaaac tggaactgaa ataa                                          324
```

<210> SEQ ID NO 9
<211> LENGTH: 357
<212> TYPE: DNA
<213> ORGANISM: Artificial Sequence
<220> FEATURE:
<223> OTHER INFORMATION: anti-EGFR1_HC_variable_DNA

<400> SEQUENCE: 9

```
caggtgcagc tgaaacagag cggtccgggt ctggttcagc cgagccagag cctgagcatt    60
acctgtaccg ttagcggttt tagcctgacc aattatggtg ttcattgggt tcgtcagagt   120
ccgggtaaag gtctggaatg gctgggtgtt atttggagcg gtggtaatac cgattataac   180
accccgttta ccagccgtct gagcattaat aaagataata gcaaaagcca ggtgttcttt   240
aaaatgaata gcctgcagag caatgatacc gccatctatt attgtgcacg tgccctgaca   300
tattatgatt atgaatttgc atattgggga cagggcaccc tggttaccgt tagtgcc     357
```

<210> SEQ ID NO 10
<211> LENGTH: 645
<212> TYPE: DNA
<213> ORGANISM: Artificial Sequence
<220> FEATURE:
<223> OTHER INFORMATION: anti-EGFR1 Fab light chain DNA, codon optimized
      for E. coli

<400> SEQUENCE: 10

```
gatattctgc tgacccagag tccggttatt ctgagcgtta gtccgggtga acgtgttagc    60
tttagctgtc gtgcaagcca gagcattggc accaatattc attggtatca gcagcgtacc   120
aatggtagtc cgcgtctgct gatcaaatat gcaagcgaaa gcattagcgg tattccgagc   180
cgttttagcg gtagcggtag tggcaccgat tttaccctga gcattaatag cgttgaaagc   240
gaagatatcg ccgattatta ctgccagcag aacaataatt ggccgaccac ctttggtgca   300
ggtacaaaac tggaactgaa acgtaccgtt gcagcaccga gcgtttttat ctttccgcct   360
agtgatgaac agctgaaaag cggcaccgca agcgttgttt gtctgctgaa taacttttat   420
ccgcgtgaag caaaagttca gtggaaagtt gataatgcac tgcagagcgg taatagccaa   480
gaaagcgtta ccgaacagga tagcaaagat agcacctata gcctgagcag caccctgacc   540
ctgagtaaag cagattatga aaaacacaaa gtgtatgcct gcgaagttac ccatcagggt   600
ctgagcagtc cggtgaccaa aagctttaat cgtggtgaat gttaa                   645
```

<210> SEQ ID NO 11
<211> LENGTH: 678
<212> TYPE: DNA
<213> ORGANISM: Artificial Sequence
<220> FEATURE:
<223> OTHER INFORMATION: anti-EGFR1 Fab heavy chain DNA, codon optimized
      for E. coli

<400> SEQUENCE: 11

```
caggtgcagc tgaagcagtc cggccctggc ctggtgcagc cttcccagtc cctgtccatc    60
acctgtaccg tgtccggctt ctccctgacc aactacggcg tgcactgggt gcgacagtcc   120
ccggcaaggg gcctggaatg gctgggagtg atttggagcg gcggcaacac cgactacaac   180
accccttca cctcccggct gtccatcaac aaggacaact ccaagtccca ggtgttcttc   240
aagatgaact ccctgcagtc caacgacacc gccatctact actgcgccag agccctgacc   300
```

| | |
|---|---|
| tactatgact acgagttcgc ctactggggc cagggcaccc tggtgacagt gtccgccgct | 360 |
| tccaccaagg gcccctccgt gttccctctg gcccccctcca gcaagtccac ctctggcggc | 420 |
| accgctgccc tgggctgtct ggtgaaagac tacttccccg agcccgtgac cgtgtcctgg | 480 |
| aactctggcg ccctgacctc cggcgtgcac accttccctg ccgtgctgca gtcctccggc | 540 |
| ctgtactccc tgtcctccgt ggtgaccgtg ccctccagct ctctgggcac ccagacctac | 600 |
| atctgcaacg tgaaccacaa gcccctccaa ccaaggtgg acaagcgggt ggaacccaag | 660 |
| tcctgcgaca agacccac | 678 |

<210> SEQ ID NO 12
<211> LENGTH: 726
<212> TYPE: DNA
<213> ORGANISM: Artificial Sequence
<220> FEATURE:
<223> OTHER INFORMATION: anti-EGFR1_scFV_DNA

<400> SEQUENCE: 12

| | |
|---|---|
| caggtgcagc tgaaacagag cggtccgggt ctggttcagc cgagccagag cctgagcatt | 60 |
| acctgtaccg ttagcggttt tagcctgacc aattatggtg ttcattgggt cgtcagagt | 120 |
| ccgggtaaag gtctggaatg gctgggtgtt atttggagcg gtggtaatac cgattataac | 180 |
| accccgttta ccagccgtct gagcatcaat aaagataata gcaaaagcca ggtgttcttt | 240 |
| aaaatgaata gcctgcagag caatgatacc gccatctatt attgtgcacg tgccctgaca | 300 |
| tattatgatt atgaatttgc atattgggga cagggcaccc tggttaccgt tagtgccggt | 360 |
| ggtggtggta gcggtggtgg cggttcaggt ggcggtggtt cagatattct gctgacccag | 420 |
| tcaccggtta ttctgagcgt tagtccgggt gaacgtgtta gctttagctg tcgtgcaagc | 480 |
| cagagcattg gcaccaatat tcattggtat cagcagcgta ccaatggtag tccgcgtctg | 540 |
| ctgatcaaat atgcaagcga aagcattagc ggtattccga ccgttttag cggttctggt | 600 |
| agcggcaccg attttaccct gagtattaat agcgttgaaa gcgaagatat cgccgattat | 660 |
| tactgccagc aaaataacaa ttggccgacc accttggtg caggtacaaa actggaactg | 720 |
| aaataa | 726 |

<210> SEQ ID NO 13
<211> LENGTH: 792
<212> TYPE: DNA
<213> ORGANISM: Artificial Sequence
<220> FEATURE:
<223> OTHER INFORMATION: anti-EGFR1_scFV_DNA_with_ompA

<400> SEQUENCE: 13

| | |
|---|---|
| atgaaatacc tgctgccgac cgcagcagcg gtgctgctgc tgctggcagc acagcctgca | 60 |
| atggcacagg tgcagctgaa acagagcggt ccgggtctgg ttcagccgag ccagagcctg | 120 |
| agcattacct gtaccgttag cggttttagc ctgaccaatt atggtgttca ttgggttcgt | 180 |
| cagagtccgg gtaaaggtct ggaatggctg gtgttatttt ggagcggtgg taataccgat | 240 |
| tataacaccc cgtttaccag ccgtctgagc atcaataaag ataatagcaa aagccaggtg | 300 |
| ttctttaaaa tgaatagcct gcagagcaat gataccgcca tctattattg tgcacgtgcc | 360 |
| ctgacatatt atgattatga atttgcatat tggggacagg gcaccctggt taccgttagt | 420 |
| gccggtggtg gtggtagcgg tggtggcggt tcaggtggcg gtggttcaga tattctgctg | 480 |
| acccagtcac cggttattct gagcgttagt ccgggtgaac gtgttagctt tagctgtcgt | 540 |
| gcaagccaga gcattggcac caatattcat tggtatcagc agcgtaccaa tggtagtccg | 600 |

```
cgtctgctga tcaaatatgc aagcgaaagc attagcggta ttccgagccg ttttagcggt    660
tctggtagcg gcaccgattt taccctgagt attaatagcg ttgaaagcga agatatcgcc    720
gattattact gccagcaaaa taacaattgg ccgaccacct ttggtgcagg tacaaaactg    780
gaactgaaat aa                                                       792
```

```
<210> SEQ ID NO 14
<211> LENGTH: 241
<212> TYPE: PRT
<213> ORGANISM: Artificial Sequence
<220> FEATURE:
<223> OTHER INFORMATION: anti-EGFR1_scFV

<400> SEQUENCE: 14
```

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Gly Gly Gly Gly Ser Gly Gly Gly Gly
        115                 120                 125

Ser Gly Gly Gly Gly Ser Asp Ile Leu Leu Thr Gln Ser Pro Val Ile
    130                 135                 140

Leu Ser Val Ser Pro Gly Glu Arg Val Ser Phe Ser Cys Arg Ala Ser
145                 150                 155                 160

Gln Ser Ile Gly Thr Asn Ile His Trp Tyr Gln Gln Arg Thr Asn Gly
                165                 170                 175

Ser Pro Arg Leu Leu Ile Lys Tyr Ala Ser Glu Ser Ile Ser Gly Ile
            180                 185                 190

Pro Ser Arg Phe Ser Gly Ser Gly Ser Gly Thr Asp Phe Thr Leu Ser
        195                 200                 205

Ile Asn Ser Val Glu Ser Glu Asp Ile Ala Asp Tyr Tyr Cys Gln Gln
    210                 215                 220

Asn Asn Asn Trp Pro Thr Thr Phe Gly Ala Gly Thr Lys Leu Glu Leu
225                 230                 235                 240

Lys

```
<210> SEQ ID NO 15
<211> LENGTH: 263
<212> TYPE: PRT
<213> ORGANISM: Artificial Sequence
<220> FEATURE:
<223> OTHER INFORMATION: anti-EGFR1_scFV_with_ompA

<400> SEQUENCE: 15
```

Met Lys Tyr Leu Leu Pro Thr Ala Ala Ala Gly Leu Leu Leu Leu Ala
1               5                   10                  15

Ala Gln Pro Ala Met Ala Gln Val Gln Leu Lys Gln Ser Gly Pro Gly
            20                  25                  30

Leu Val Gln Pro Ser Gln Ser Leu Ser Ile Thr Cys Thr Val Ser Gly
        35                  40                  45

Phe Ser Leu Thr Asn Tyr Gly Val His Trp Val Arg Gln Ser Pro Gly
    50                  55                  60

Lys Gly Leu Glu Trp Leu Gly Val Ile Trp Ser Gly Asn Thr Asp
65              70                  75                  80

Tyr Asn Thr Pro Phe Thr Ser Arg Leu Ser Ile Asn Lys Asp Asn Ser
                85                  90                  95

Lys Ser Gln Val Phe Phe Lys Met Asn Ser Leu Gln Ser Asn Asp Thr
            100                 105                 110

Ala Ile Tyr Tyr Cys Ala Arg Ala Leu Thr Tyr Tyr Asp Tyr Glu Phe
        115                 120                 125

Ala Tyr Trp Gly Gln Gly Thr Leu Val Thr Val Ser Ala Gly Gly Gly
    130                 135                 140

Gly Ser Gly Gly Gly Ser Gly Gly Gly Ser Asp Ile Leu Leu
145                 150                 155                 160

Thr Gln Ser Pro Val Ile Leu Ser Val Ser Pro Gly Glu Arg Val Ser
                165                 170                 175

Phe Ser Cys Arg Ala Ser Gln Ser Ile Gly Thr Asn Ile His Trp Tyr
            180                 185                 190

Gln Gln Arg Thr Asn Gly Ser Pro Arg Leu Leu Ile Lys Tyr Ala Ser
        195                 200                 205

Glu Ser Ile Ser Gly Ile Pro Ser Arg Phe Ser Gly Ser Gly Ser Gly
    210                 215                 220

Thr Asp Phe Thr Leu Ser Ile Asn Ser Val Glu Ser Glu Asp Ile Ala
225                 230                 235                 240

Asp Tyr Tyr Cys Gln Gln Asn Asn Asn Trp Pro Thr Thr Phe Gly Ala
                245                 250                 255

Gly Thr Lys Leu Glu Leu Lys
            260

<210> SEQ ID NO 16
<211> LENGTH: 18
<212> TYPE: PRT
<213> ORGANISM: Artificial Sequence
<220> FEATURE:
<223> OTHER INFORMATION: gIII

<400> SEQUENCE: 16

Met Lys Lys Leu Leu Phe Ala Ile Pro Leu Val Val Pro Phe Tyr Ser
1               5                   10                  15

His Ser

<210> SEQ ID NO 17
<211> LENGTH: 21
<212> TYPE: PRT
<213> ORGANISM: Artificial Sequence
<220> FEATURE:
<223> OTHER INFORMATION: ompA

<400> SEQUENCE: 17

Met Lys Lys Thr Ala Ile Ala Ile Ala Val Ala Leu Ala Gly Phe Ala
1               5                   10                  15

Thr Val Ala Gln Ala
            20

<210> SEQ ID NO 18
<211> LENGTH: 26
<212> TYPE: PRT
<213> ORGANISM: Artificial Sequence
<220> FEATURE:
<223> OTHER INFORMATION: malE

<400> SEQUENCE: 18

Met Lys Ile Lys Thr Gly Ala Arg Ile Leu Ala Leu Ser Ala Leu Thr
1               5                   10                  15

Thr Met Met Phe Ser Ala Ser Ala Leu Ala
            20                  25

<210> SEQ ID NO 19
<211> LENGTH: 21
<212> TYPE: PRT
<213> ORGANISM: Artificial Sequence
<220> FEATURE:
<223> OTHER INFORMATION: phoA

<400> SEQUENCE: 19

Met Lys Gln Ser Thr Ile Ala Leu Ala Leu Leu Pro Leu Leu Phe Thr
1               5                   10                  15

Pro Val Thr Lys Ala
            20

<210> SEQ ID NO 20
<211> LENGTH: 22
<212> TYPE: PRT
<213> ORGANISM: Artificial Sequence
<220> FEATURE:
<223> OTHER INFORMATION: pelB

<400> SEQUENCE: 20

Met Lys Tyr Leu Leu Pro Thr Ala Ala Ala Gly Leu Leu Leu Leu Ala
1               5                   10                  15

Ala Gln Pro Ala Met Ala
            20

<210> SEQ ID NO 21
<211> LENGTH: 23
<212> TYPE: PRT
<213> ORGANISM: Artificial Sequence
<220> FEATURE:
<223> OTHER INFORMATION: stII

<400> SEQUENCE: 21

Met Lys Lys Asn Ile Ala Phe Leu Leu Ala Ser Met Phe Val Phe Ser
1               5                   10                  15

Ile Ala Thr Asn Ala Tyr Ala
            20

<210> SEQ ID NO 22
<211> LENGTH: 31
<212> TYPE: DNA
<213> ORGANISM: Artificial Sequence
<220> FEATURE:
<223> OTHER INFORMATION: internal ribosome binding site

<400> SEQUENCE: 22
taaggatccg aattcaagga gataaaaaat g                              31

<210> SEQ ID NO 23
<211> LENGTH: 50

```
<212> TYPE: DNA
<213> ORGANISM: Artificial Sequence
<220> FEATURE:
<223> OTHER INFORMATION: Primer sequence for construction of GP1113

<400> SEQUENCE: 23
cgggatccaa gaaggagata taccatggca aaaaagtggt tattagctgc            50

<210> SEQ ID NO 24
<211> LENGTH: 35
<212> TYPE: DNA
<213> ORGANISM: Artificial Sequence
<220> FEATURE:
<223> OTHER INFORMATION: Primer sequence for construction of GP1114

<400> SEQUENCE: 24
ataatgcggc cgcattattt aacctgtttc agtac                            35

<210> SEQ ID NO 25
<211> LENGTH: 56
<212> TYPE: DNA
<213> ORGANISM: Artificial Sequence
<220> FEATURE:
<223> OTHER INFORMATION: Primer sequence for construction of GP1115

<400> SEQUENCE: 25
ataatgcggc cgcaagaagg agatatacca tggcaaaatc actgtttaaa gtaacg     56

<210> SEQ ID NO 26
<211> LENGTH: 33
<212> TYPE: DNA
<213> ORGANISM: Artificial Sequence
<220> FEATURE:
<223> OTHER INFORMATION: Primer sequence for construction of GP1116

<400> SEQUENCE: 26
ataatctcga gattattttt tagcagaatc tgc                              33

<210> SEQ ID NO 27
<211> LENGTH: 54
<212> TYPE: DNA
<213> ORGANISM: Artificial Sequence
<220> FEATURE:
<223> OTHER INFORMATION: Primer sequence for construction of GP1147

<400> SEQUENCE: 27
tgacccgcta atgcggccgc actgagtgct tcccttgaaa ccctgaaact gatc       54

<210> SEQ ID NO 28
<211> LENGTH: 59
<212> TYPE: DNA
<213> ORGANISM: Artificial Sequence
<220> FEATURE:
<223> OTHER INFORMATION: Primer sequence for construction of GP1148

<400> SEQUENCE: 28
ggtttcttta ccagactcaa acggcccggc attcgcatgc agggccgtga attattacg  59

<210> SEQ ID NO 29
<211> LENGTH: 45
<212> TYPE: DNA
<213> ORGANISM: Artificial Sequence
<220> FEATURE:
<223> OTHER INFORMATION: G4S_linker/spacer_DNA

<400> SEQUENCE: 29
```

```
ggtggtggtg gtagcggtgg tggcggttca ggtggcggtg gttca                45

<210> SEQ ID NO 30
<211> LENGTH: 15
<212> TYPE: PRT
<213> ORGANISM: Artificial Sequence
<220> FEATURE:
<223> OTHER INFORMATION: G4S_linker/spacer

<400> SEQUENCE: 30

Gly Gly Gly Gly Ser Gly Gly Gly Gly Ser Gly Gly Gly Gly Ser
1               5                   10                  15
```